United States Patent
Roy et al.

(10) Patent No.: US 7,341,866 B2
(45) Date of Patent: Mar. 11, 2008

(54) α-CATENIN EXPRESSED IN HEART AND TESTIS

(75) Inventors: Frans Van Roy, Destelbergen (BE); Steven Goossens, Ghent (BE); Barbara Janssens, Ghent (BE); Griet Vanpoucke, Merelbeke (BE)

(73) Assignee: Vlaams Interuniversitair Instituut voor Biotechnologie VZW, Zwijnaarde (BE)

( * ) Notice: Subject to any disclaimer, the term of this patent is extended or adjusted under 35 U.S.C. 154(b) by 518 days.

(21) Appl. No.: 10/345,092

(22) Filed: Jan. 13, 2003

(65) Prior Publication Data
US 2003/0165506 A1    Sep. 4, 2003

Related U.S. Application Data

(63) Continuation of application No. PCT/EP01/07392, filed on Jun. 28, 2001.

(30) Foreign Application Priority Data
Jul. 12, 2000    (EP) ................. 00202472.7

(51) Int. Cl.
*C12N 15/00* (2006.01)
*C12P 21/06* (2006.01)
*C07H 21/04* (2006.01)

(52) U.S. Cl. .................. 435/320.1; 536/23.1; 435/69.1
(58) Field of Classification Search ................ 530/350; 435/69.1, 252.3, 320.1, 6; 536/23.1
See application file for complete search history.

(56) References Cited

U.S. PATENT DOCUMENTS 5,470,966 A    11/1995    Hirano et al.

FOREIGN PATENT DOCUMENTS

| WO | WO 96/02002 | 1/1996 |
|---|---|---|
| WO | WO 98/45319 | 10/1998 |
| WO | WO 02/04636 A1 | 1/2002 |

OTHER PUBLICATIONS

Abstract, XP-002162171.
Abstract, XP-002162172.
Abstract, XP-002162173.
Abstract, XP002162169.
Abstract, XP-002162170.
Abstract, XP-002183100.
Abstract, XP-002183101.
PCT International Search Report, PCT/EP01/07392, dated Nov. 28, 2001, 3 pages.
PCT International Preliminary Examination Report, PCT/EP01/07392, dated Oct. 14, 2002, 8 pages.

*Primary Examiner*—Maryam Monshipouri
(74) *Attorney, Agent, or Firm*—TraskBritt

(57) ABSTRACT

The present invention relates to a novel α-catenin with a new, specific expression pattern in mainly heart and testis. The invention further relates to the use of this α-catenin in the prediction, diagnosis, and/or treatment of cadherin-catenin related diseases, in particular cardiomyopathies and male infertility.

11 Claims, 33 Drawing Sheets

B

Figure 1:
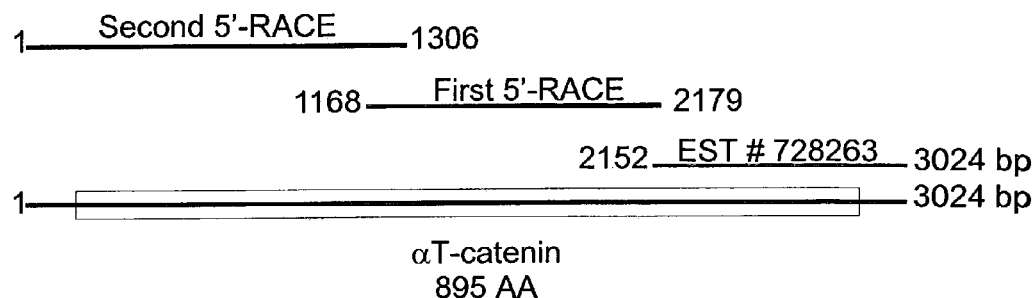

|  | vinculin | α-catulin | αT-catenin | αE-catenin | αN-catenin |
|---|---|---|---|---|---|
| vinculin | 100 % | 11.84 % | 17.62% | 18.38 % | 18.11% |
| α-catulin |  | 100 % | 18.87 % | 20.54% | 21.34% |
| αT-catenin |  |  | 100 % | 58.56% | 56.56% |
| αE-catenin |  |  |  | 100 % | 75.6% |
| αN-catenin |  |  |  |  | 100 % |

C

|  | vinculin | α-catulin | αT-catenin | αE-catenin | αN-catenin |
|---|---|---|---|---|---|
| vinculin | 100 % | 23.69 % | 30.31 % | 31.05 % | 30.02% |
| α-catulin |  | 100 % | 32.10% | 33.87 % | 32.78% |
| αT-catenin |  |  | 100 % | 73.65% | 69.57% |
| αE-catenin |  |  |  | 100 % | 83.14% |
| αN-catenin |  |  |  |  | 100 % |

Figure 2 (cont.)

```
hαT-ctn  476  KNTMEMYKRTWENHIHVLTEAVDDITSIDDFLAVSESHILEDVNKCIIALRDQDADNLDRAAGAIRGRAARVAHIVIGEM
hαE-ctn  481  QENMDLFKEQWEKQVRVLTDAVDDITSIDDFLAVSENHILEDVNKCVIALQEKDVGLDRTAGAIRGRAARVIHVTSEM
hαN2-ctn 479  QDNMDVFKDQWEKQVRVLTEAVDDITSVDDFLSVSENHILEDVNKCVIALQEGDVDTLDRTAGAIRGRAARVIHIINAEM hαT-ctn  556  DSYEPGAYTEGVRRNVNFLISTVIPEFVTQVNVAEALSKSSLNVDDNQFVDISKKYDTIHDIRCSVMIRTPEELED
hαE-ctn  561  DNYEPGVYTEKVLEATKLLSNTVMPRFTEQVEAAVEALSSDPAQPMDENEFIDASRLVYDGIRDIRKAVLMIRTPEEL.D
hαN2-ctn 559  ENYEAGVYTEKVLEATKILLSETVMPRFAEQVEVAEALSANVPQPFEENEFIDASRLVYDGVRDIRKAVLMIRTPEELED hαT-ctn  636  VSDLEEH.EVRSHTSIQTE........GKIDRAKMIQLPEAEEKIAEQVADFKVKSKLDAFIEIWDDLSNDIIVLAKNM
hαE-ctn  640  DSDFETEDFDVRSRTSVQTEDDQLIAGQSARAIMAQLPQEQKAKIAEQVASFQEEKSKLDAEVSKWDDSGNDIIVLAKQM
hαN2-ctn 639  DSDFEQEDVRGTSVQTEDDQLIAGQSARAIMAQLPQEEKAKIAEQVEIFHQEKSKLDAEVAKWDDSGNDIIVLAKQM hαT-ctn  709  CMIMMEMTDFTRGKGPLKHTIDVIIYAAKMISESGSRMDVLARQIANQCPDPSCKQDLLAYLEQIKFYSHQLKICSQVKAE
hαE-ctn  720  CMIMMEMTDFTRGKGPLKNTSDVISAAKKIAEAGSRMDKLGRTIADHCPDSACKQDLLAYLQRIALYCHHLNICSKVKAE
hαN2-ctn 719  CMIMMEMTDFTRGKGPLKNTSDVINAAKKIAEAGSRMDKLARAVADQCPDSACKQDLLAYLQRIALYCHQLNICSKVKAE
                                                                           }amphipathic helices hαT-ctn  789  LQNLGGELIMSA..........................................EDSVTSLIQAAKNLMNAVVQ
hαE-ctn  800  VQNLGGELVVSG..........................................VDSAMSLIQAAKNLMNAVVQ
hαN2-ctn 799  VQNLGGELIVSGTGVQSTFTTFYEVDCDVIDGGRASQLSTHLPTCAEGAPIGSGSSSMDSATSLIQAAKNLMNAVVL
                        }alternatively spliced insert hαT-ctn  821  TVKMSYIASTKIIRIQSPAGPRHPVVMRMKAPAKKPLIUKREKPEETCAAVRRGSAKKEHPLQVMSEFRGRQIY
hαE-ctn  832  TVKASYVASTKYQKSQGMASLNIPAVSWKMKAPEKKPLVKREKPLVKREKQDETQTKIKRASQKKHVNPVQALSEFKAMDSI
hαN2-ctn 879  VKASYVASTKYQKVYGTAAVNSPVVSWKMKAPEKKPLVKREKPEFQTRVRRGSQKKHI......FACTGFK
```

Figure 3
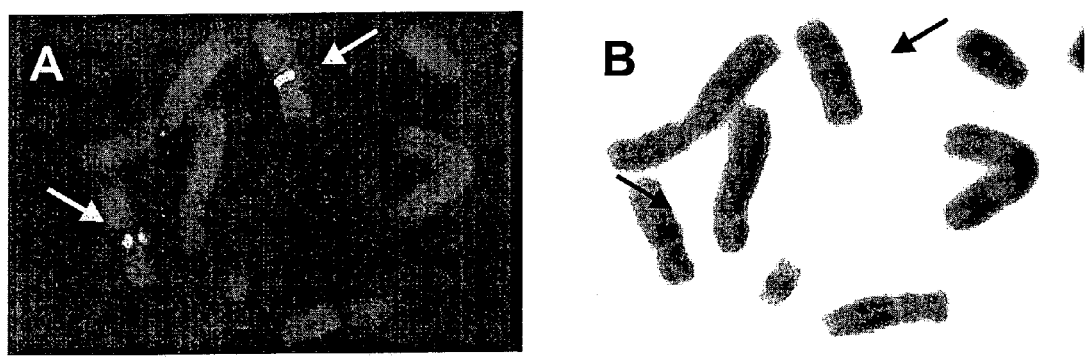
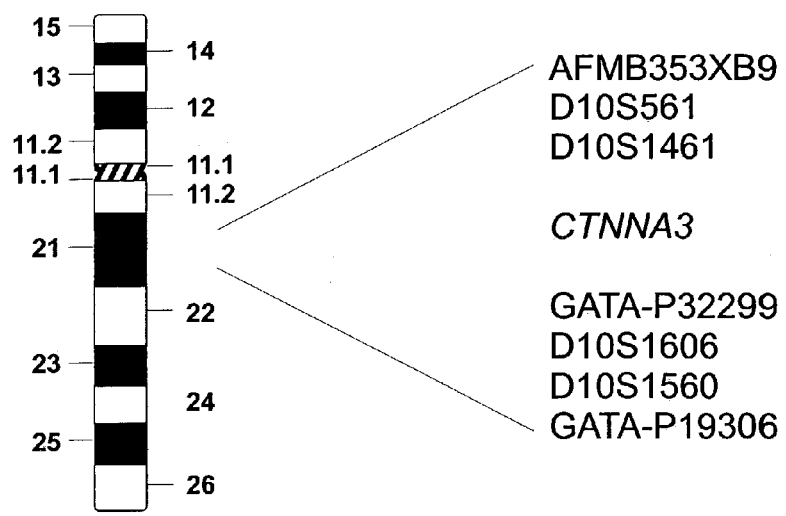

Figure 4

```
                                                   Ex2 ┐┌ Ex3
hαT-ctn   1 MSA..ETPITLNIDPQDLQVQTFTVEKLLEPLIIQVTTLVNC..PQNPSSRKKGRSKRASV
hαE-ctn   1 MTAVHAGNINFKWDPKSLEIRTLAVERLLEPLVTQVTTLVNTNSKGPSNKKRGRSKKAHV
                                                   Ex3 ┐┌ Ex4
hαT-ctn  58 LLASVEEATWNLLDKGEKIAQEATVLKDELTASLEEVRKESEALKVSAERFTDDPCFLPK
hαE-ctn  61 LAASVEQATENFLEKGDKIAKESQFLKEELVAAVEDVRKQGDLMKAAAGEFADDPCSSVK
                                        Ex4 ┐┌ Ex5
hαT-ctn 118 REAVVQAARALLAAVTRLLILADMIDVMCLLQHVSAFQRTFETLKNVANKSDLQKTYQKL
hαE-ctn 121 RGNMVRAARALLSAVTRLLILADMADVYKLLVQLKVVEDGILKLRNAGNEQDLGIQYKAL
                      Ex5 ┐┌ Ex6
hαT-ctn 178 GKELENLDYLAFKRQQDLKSPNQRDEIAGARASLKENSPLLHSICSACLEHSDVASLKAS
hαE-ctn 181 KPEVDKLNIMAAKRQQELKDVGHRDQMAAARGILQKNVPILYTASQACLQHPDVAAYKAN
                                   Ex6 ┐┌ Ex7
hαT-ctn 238 KDTVCEEIQNALNVISNASQGI..QNMTTPPEPQAATLGSALDELENLIVLNPLTVTEEE
hαE-ctn 241 RDLIYKQLQQAVTGISNAAQATASDDASQHQGGGGELAYALNNFDKQIIVDPLSFSEER
                                                 Ex7 ┐┌ Ex8
hαT-ctn 296 IRPSLEKRLEAIISGAALLADSSCTRDLHRERIIAECNAIRQALQDLLSEYMNNAGKKER
hαE-ctn 301 FRPSLEERLESIISGAALMADSSCTRDDRRERIVAECNAVRKALQDLLSEYMGNAGRKER
                                ???
```

Figure 4 (cont.)

```
                      Ex8       Ex8
hαT-ctn  356  SNTLNIALDNMCKKTRDLRRQLRKAIIDHVSDSFLDTTVPLLVLIEAAKNGREKEIKEYA
hαE-ctn  361  SDALNSAIDKMTKKTRDLRRQLRKAVMDHVSDSFLETNVPLLVLIEAAKNGNEKEVKEYA
                                    Ex9         Ex10           Ex11
hαT-ctn  416  AIFHEHTSRLVEVANLACSMSTNEDGIKIVKIAANHLETLCPQIINAALALAARPKSQAV
hαE-ctn  421  QVFREHANKLIEVANLACSISNNEEGVKLVRMSASQLEALCPQVINAALALAAKPQSKLA
                        Ex9        Ex11         Ex12
hαT-ctn  476  KNTMEMYKRTWENHIHVLTEAVDDITSIDDFLAVSESHILEDVNKCIIALRDQDADNLDR
hαE-ctn  481  QENMDLFKEQWEKQVRVLTDAVDDITSIDDFLAVSENHILEDVNKCVIALQEKDVDGLDR
                                        Ex12    Ex13
hαT-ctn  536  AAGAIRGRAARVAHIVTGEMDSYEPGAYTEGVMRNVNFLTSTVIPEFVTQVNVALEALSK
hαE-ctn  541  TAGAIRGRAARVIHVVTSEMDNYEPGVYTEKVLEATKLLSNTVMPRFTEQVEAAVEALSS
                       Ex13        Ex14
hαT-ctn  596  SSLNVLDDNQFVDISKKIYDTIHDIRCSVVMIRTPEELEDVSDLEEEHEVRSHTSIQTE.
hαE-ctn  601  DPAQPMDENEFIDASRLVYDGIRDIRKAVLMIRTPEELDDSDFETEDFDVRSRTSVQTED
```

Figure 4 (cont.)

```
                        Ex14
hαT-ctn  655  ......GKTD RA KMTQLPEAEKEKIAEQVADFKKVKSKLDAEIEIWDDTSNDIIVLAKNMC
hαE-ctn  661  DQLIAGQSARAIMAQLPQEQKAKIAEQVASFQEEKSKLDAEVSKWDDSGNDIIVLAKQMC
                              Ex15
                 Ex15
hαT-ctn  710  MIMMEMTDF TRGKG PLKHTTDVIYAAKMISESGSRMDVLARQIAN QC PDPSCKQDLLAYL
hαE-ctn  721  MIMMEMTDF TRGKG PLKNTSDVISAAKKIAEAGSRMDKLGRTIA DH CPDSACKQDLLAYL
                              Ex17 ⎤⎡ Ex18
hαT-ctn  770  EQIKFYSHQLKICSQVKAEIQNLGGELIMS AL DSVTSLIQAAKNLMNAVVQTVKMSYIAS
hαE-ctn  781  QRIALYCHHLNICSKVKAEVQNLGGELVVS GV DSAMSLIQAAKNLMNAVVQTVKASYVAS hαT-ctn  830  TKIIRIQSPAGPRHPVVMWRMKAPAKKPLIKREKPEETCAAVRRGSAKKKIHPLQVMSEF
hαE-ctn  841  TKYQKSQGMASLNLPAVSWKMKAPEKKPLVKREKQDETQTKIKRASQKKHVNPVQALSEF hαT-ctn  890  RGRQIY
hαE-ctn  901  KAMDSI
```

Figure 6

A

```
GTCCTGGTTT GGAAAACATT CATTATTAAA GCTCTAAAAC AAAACCTGCT ATTTTGCAAG    60
TGTCAAGTGA TTTCTTTATT CAAGAAAAGA TGGATTGAGA GACATAAAAC TTACTCTTTG   120
TTTCACTGTG AAAAGATGCT ATTCCTAGAT TCTCCAGGGG GAAAAAGCTG CTTTAAAAAA   180
ATCTGGGGAG GATAGCATGT TAGCAACTAA GAATCTTTAG ATAAATATAT TGTCAATTAT   240
GCCCATTTTA AAGGTAGCTA CATAAAAATA CAGTTGTTTT GAAGGCTATC CTGAAAATCA   300
TATAAAATGA ACTCCTTTCA TAGTTGATTC TCTGACAGTT CCCAGACCCT GCCTTTCCTC   360
TTGGCTCCCT GAAATTTGTG CTAAGAGTAT CTGGAGAGCC AATAAATAAA TGCTTTCTTT   420
TTATTTTGAA TTCAGCCTTT TAAGAACAGG ACTGCCAAAA CTCAAACAAG TAGTTCATAT   480
TTTAGTTAGC ACCTCTTGTT TTAGAAGCTA TTAGAAGAAA GTCGGAAAAA TGGTAATGTC   540
CAAGGAAATG CCACAGAAGT TCGAGTGGGA TGTCAAGGAA TTGATGAAAT GATAAAGATT   600
                                                      GATA-site
GTTTCAGTGG ATGTGAAGAT ATTGAGGGAG AAGATATCAA AAAAAAGGGA AAAGGAAATG   660
TGAAAAAGAA TAGTCATAGA GAGAAAAAAT AAATTTGGT GGAGAAGACT TTTTTTTTTG   720
GTGGCTTAAA TTTAATAAATG GGTTAACCTA TTGAGTTTTT GGTAAATCTT CAGTTTAGAT   780
TCTTTACTGA TAATGATGTG GTTCCTCATA AATACTGGAA GGAGAGAGTG TGATGCTTGG   840
  GATA-site
TACAAGGGAT GAGACAGGTA ATATTTCAGA AGAAGAAAAA TACGATCTCA GATGTGACAC   900
ATGGCCTTGA TGCCATCATC TCTAGGGTTC TGAAGACATT GAATTTTACA TAATTGATCT   960
                                                      Nkx2.5 site
```

Figure 6 (cont.)

```
TTTGATGTGA GGATTTCCTG GACTCTTGTT TTCCCTGCTT TATCATTTTT CACTTTCAAT 1020
                                            GATA-site
AATTCCAGCC TTTGGCTTTA ATTAGATAGA AGAGGTTCTT CTTTTGGAAA GGAACTAGAG 1080
                     GATA-site
AAATGCAAAT CTAAACTTAT TCAGAGCTAT GTTTGTAGGT CTCTAGGCAA AGTATGTGTC 1140

TGGCCTTTTT CAACGAAGTA TTTTCAGTAA CAAGTTGTCA GTGAGGTCAG TGACTAGCGG 1200
              MEF2C-site
TTCAGGATTA GATACCACCC ACCCTGGCTT GTAACCTCCC CTTTCTTTCT TATCCTGGGT 1260
         GATA-site                                     GATA-site
GAACAACGCT CAGCGAAATT GACTGCCCCA CTGTCATCTG CCCTCTCAATT TGGTACTCTG 1320

TAACTCTGTG ACCACCAAGA AGCCTTTTTC CGTCCCCCAC AAAGCTCTTT TTGGAAAATT 1380

CCCTACGGGA GCTGAATTTT AAGCCCATTT ACTTTATAGG AAGAAACAGA AAGGTAAGAA 1440

TCAAGTTTGT AAAGAGAAGA GCTGAACTTC AGCGAATTCT CATTTCTGCA TTGAATTCCT 1500

GTGTCTTAGT TATAATCATA GGTTTAAAAT TTGGGGTTTT CTTCTGAACT GAGGAAGATC 1560

ACATTATTGT ATGAAATAGG AATGTTTTGA CTAGTTATGA GAAACGTAGG CTTTCACGCT 1620

AATTTTAAAG TTATAAATAA CTTTCGAACT ATTGCCAGGG GAAGCTGGTA GCCAAGGTCG 1680

TGCTTTGCAT TCAGAGAGTT TCTGGCTATA AAAAGCCGAT TGGATACTGT GCAGGAAAAG 1740
```

```
HUMAN-372 CAGAAGAAGAAAAATACGATCTCAGATGTGACACATGCCTTGATGCCATCATCTCTAGG
MOUSE-339 CGCCAGAAAAAA----CGATCTCAGATGTGACCCATGAC-----------------------
```

B

Figure 6 (cont.)

Figure 7 A - B
A
| BAIT | PREY |
|---|---|
| pVA3 | pTD1 |
| αT-catenin | β-catenin |
| α-catulin | β-catenin |
| αE-catenin | β-catenin |
| αN-catenin | β-catenin |
| pVA3 | β-catenin |
| pVA3 | pTD1 |
| αT-catenin | Plakoglobin |
| α-catulin | Plakoglobin |
| αE-catenin | Plakoglobin |
| αN-catenin | Plakoglobin |
| pVA3 | Plakoglobin |
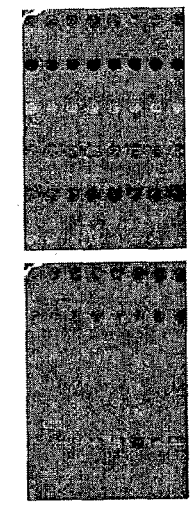
B
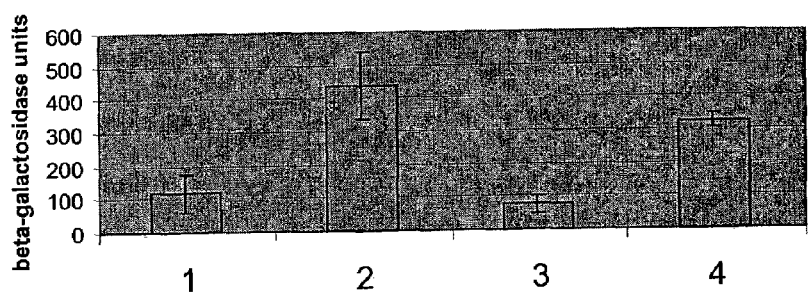
Quantification of interaction between alphaE- or alphaT-catenin and beta-catenin Figure 7 C -D
C
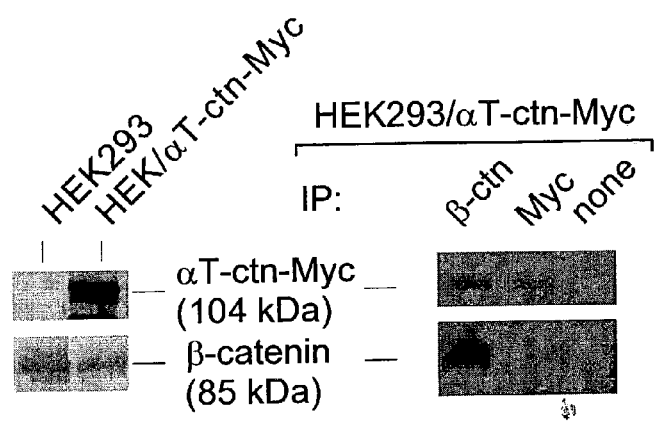
D
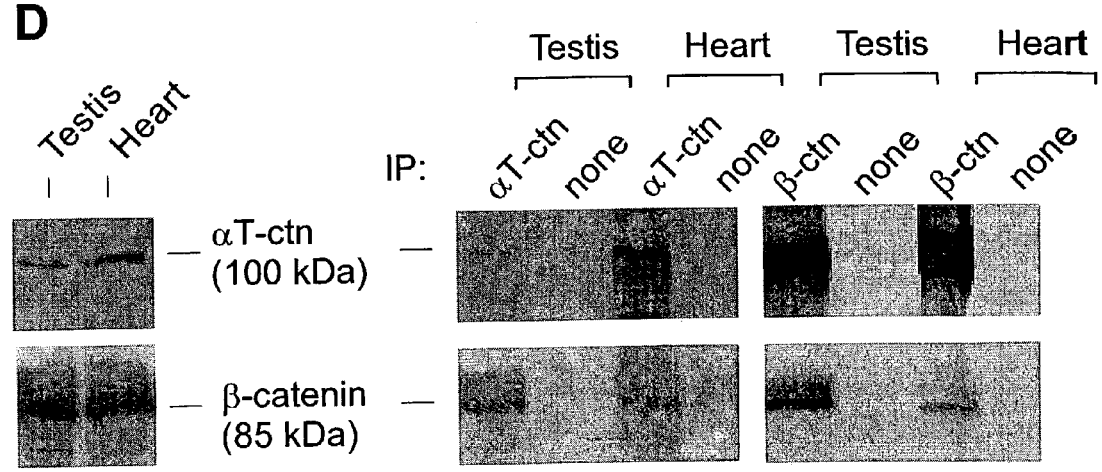

Figure 9
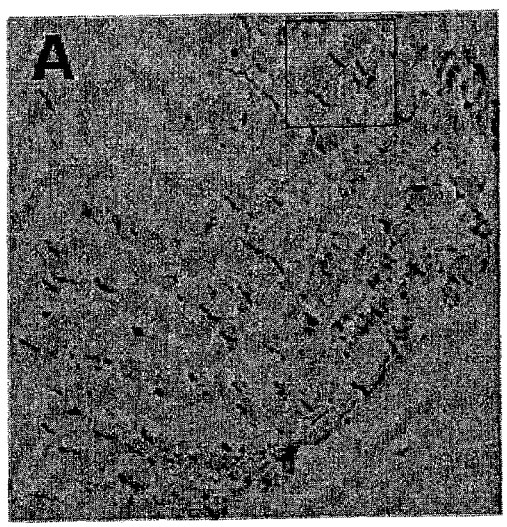
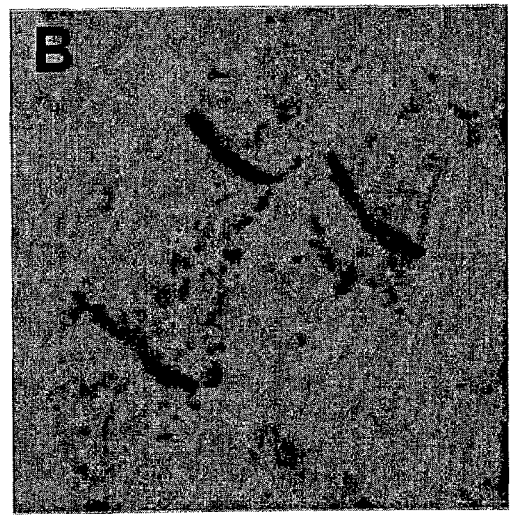
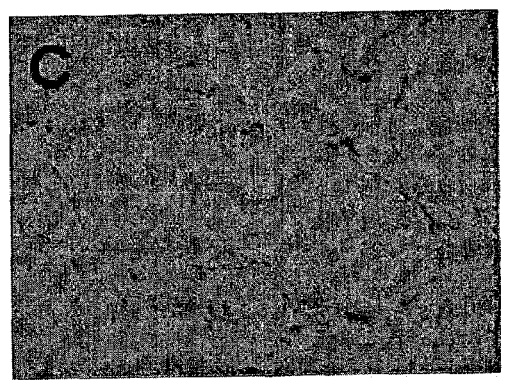
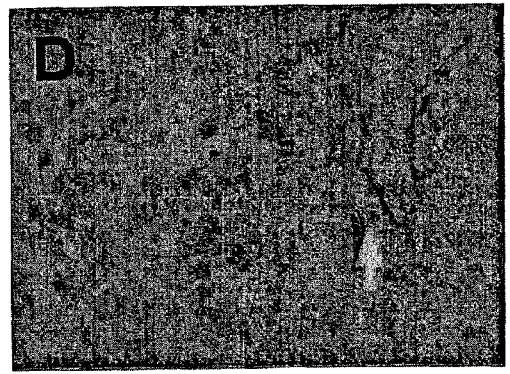

Figure 15
HCT-8/R1
(no α-catenin)
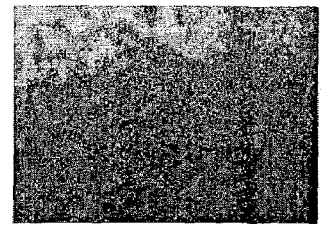
HCT-8/R1/1743
(no α-catenin)
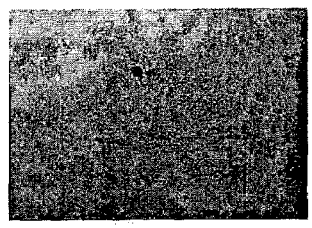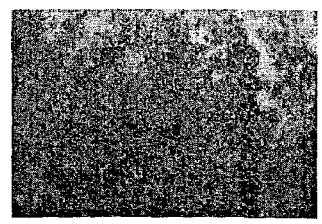
HCT-8/E8
(αE-catenin)
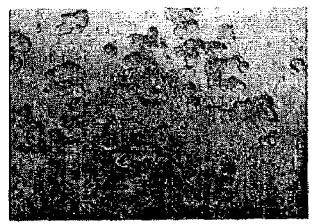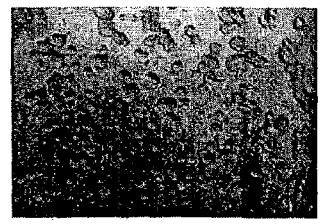
HRpCαN2
(αN-catenin)
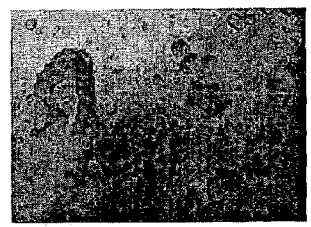
HCT-8/R1/T31
(αT-catenin)
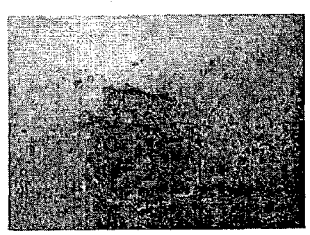

Figure 17
A
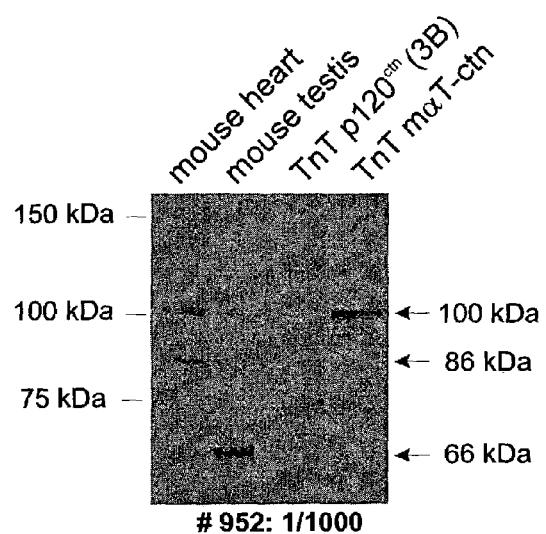
B
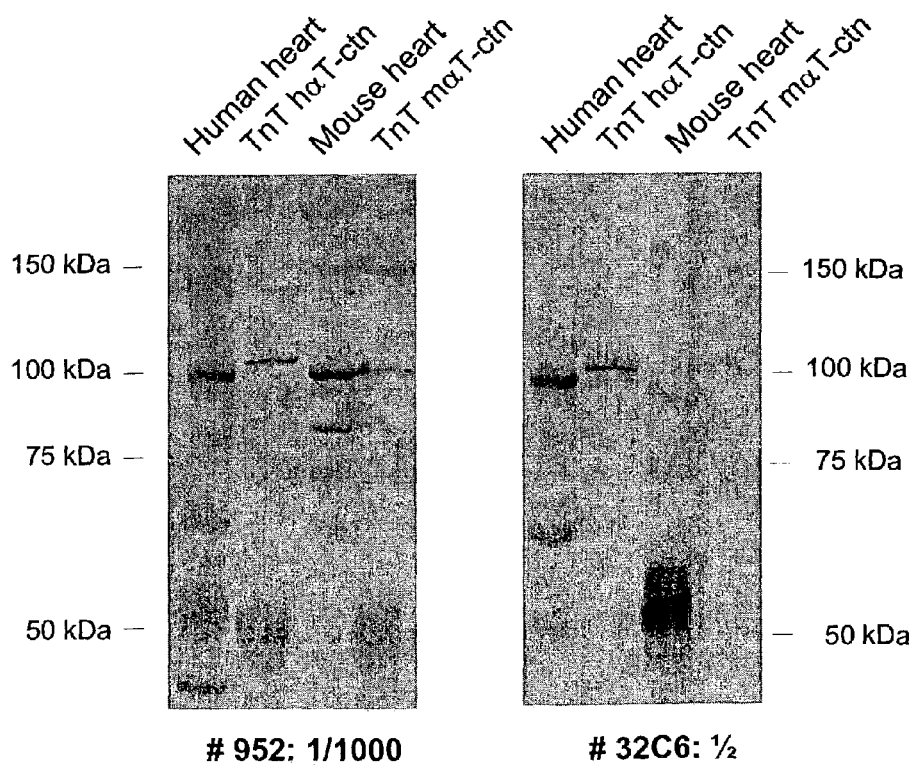

Figure 18

```
maTctn.pro    1  MSAETPITLNMDTQDLQTQTFTVEKLLEPLIIQVTTLVNCPQNPSNRKKGRSKRARVLLA
haTctn.pro    1  MSAETPITLNMDPQDLQVQTFTVEKLLEPLIIQVTTLVNCPQNPSSRKKGRSKRASVLLA
                                              α-helix-0 maTctn.pro   61  SVEEATWNLLDKGEMIAKEATVLKEELAAAIQEVRKESKALKVSAERFTDDPCYLPKREA
haTctn.pro   61  SVEEATWNLLDKGEKIAQEATVLKDELTASLEEVRKESEALKVSAERFTDDPCELPKREA
                                      β-ctn binding                α-helix-1 maTctn.pro  121  VVQAARALLAAVTRILLVLADMIDVMCLLQHVSSFQRTFESLKNVSNKSDLQRTYQKLGKE
haTctn.pro  121  VVQAARALLAAVIRILILADMIDVMCLLQHVSAFQRTFELKNVANKSDLQKTYQKLGKE
                        α-helix-2a              α-helix-2b          α-helix-3
                         β-ctn binding maTctn.pro  181  LESLDYLAFKRQQDLKSPSQRDEIAGARATLKENSPLLHSICSACLEHSDVASLKASKDT
haTctn.pro  181  LENLDYLAFKRQQDLKSPNQRDEIAGARASLKENSPLLHSICSACLEHSDVASLKASKDT
                                           α-helix-4 maTctn.pro  241  VCEEIQNALDVISNASQGIQNAPAPPEPQAATLGSAFDELENLIVLNPLTVTEEDVRPSL
haTctn.pro  241  VCEEIQNAINVISNASQGIQNMTTPPEPQAATLGSALDELENLIVLNPLTVTEEIRPSL
                    α-helix-5
```

Figure 18 (cont.)

```
maTctn.pro  301 EKRLEAIISGAALLADSSCTRDLHRERIIAECNAIRQALQDLISEYMSNTGKTERSNTLN
haTctn.pro  301 EKRLEAIISGAALLADSSCTRDLHRERIIAECNAIRQALQDLISEYMNNAGKKERSNTLN maTctn.pro  361 TAIVNMSKKTRDLRRQLRKAIIDHISDSFLDTTVPLLVLIEAAKNGRVKEIKDYAAIFHE
haTctn.pro  361 IALDNMCKKTRDLRRQLRKAIIDHVSDSFLDTTVPLLVLIEAAKNGREKEIKEYAAIFHE maTctn.pro  421 HTGRLVEVANLACSMSTNEDGIKIVRIAANHLETLCPQINAALALASRPKSQVVKNTME
haTctn.pro  421 HTSRLVEVANLACSMSTNEDGIKIVKIAANHLETLCPQINAALALAARPKSQAVKNTME maTctn.pro  481 MYKRTWEHYIHVLTEAVDDITSIDDFLAVSESHILEDVNKCIIALRDQDADNLDRAAGAI
haTctn.pro  481 MYKRTWENHIHVLTEAVDDITSIDDFLAVSESHILEDVNKCIIALRDQDADNLDRAAGAI maTctn.pro  541 RGRAARVAHIVAGEMDSYEPGAYTEGVMRNVNFLTSTVIPEFVTQVNVALDALSKNSLTA
haTctn.pro  541 RGRAARVAHIVTGEMDSYEPGAYTEGVMRNVNFLTSTVIPEFVTQVNVALEALSKSSINV maTctn.pro  601 LDDNQFVDISKKIYDTIHDIRCSVMMIRTPEELEDVSDLEDDHEVRSHTSIQTEGKTDRA
haTctn.pro  601 LDDNQFVDISKKIYDTIHDIRCSVMMIRTPEELEDVSDLEEEHEVRSHTSIQTEGKTDRA
```

Figure 18 (cont.)

```
maTctn.pro  661 KMTQLPEAEKEKIAEQVADFKKVKSKLDAEIEIWDDTSNDIIVLAKKMCMIMMEMTDFTR
haTctn.pro  661 KMTQLPEAEKEKIAEQVADFKKVKSKLDAEIEIWDDTSNDIIVLAKNMCMIMMEMTDFTR maTctn.pro  721 GKGPLKHTTDVIYAAKMISESGSRMDVLARQIANQCPDPPCKQDLLAYLEQIKFYSHQLK
haTctn.pro  721 GKGPLKHTTDVIYAAKMISESGSRMDVLARQIANQCPDPSCKQDLLAYLEQIKFYSHQLK maTctn.pro  781 ICSQVKAEIQNLGGELIMSALDSVTSLIQAAKNLMNAVVQTVKMSYIASTKIIRIQSSAG
haTctn.pro  781 ICSQVKAEIQNLGGELIMSALDSVTSLIQAAKNLMNAVVQTVKMSYIASTKIIRIQSPAG maTctn.pro  841 PRHPVVMWRMKAPAKKPLIKREKPEETWAAARRGSAKKKIHPVQVMSEFRGRQVY
haTctn.pro  841 PRHPVVMWRMKAPAKKPLIKREKPEETCAAVRRGSAKKKIHPLQVMSEFRGRQLY
```

Figure 19

```
maEctn.pro    1   MTAVHAGNINFKWDPKSLEIRTLAVERLLEPLVTQVTTLVNTNSKGPSNKKRGRSKKAHVLAASVEQATE
maNctn.pro    1   MTSATS-PIILKWDPKSLEIRTLVERLLEPLVTQVTTLVNTNSNKGPSGKKKGRSKKAHVLAASVEQATQ
maTctn.pro    1   MSAETP--ITLNMDTQDLQIQTFTVEKLLEPLIIQVTTLVNCP-QNPSNRKKGRSKRARVLASVEEATW maEctn.pro   71   NFLEKGDKIAKESQFLKEEIVVAVEDVRKQGDIMKSAAGEFADDPCSSVKRGNMVRAARALLSAVTRLLI
maNctn.pro   70   NFLEKGEQIAKESQDLKEEIVAAVEDVRKQGETKPIASSEFADDPCSSVKRGTMVRAARALLSAVTRLLI
maTctn.pro   68   NLIDKGEMLAKEATVLKEELAAAQEVRKESKAEKVSAERFTTDDPCYLPKREAVVQAARALLAAVTRLLV maEctn.pro  141   LADMADVYKLIVQLKVVEDGILKLRNAGNEQDICIQYKALKPEVDKLNIMAAKRQOELKDVGNRDQMAAA
maNctn.pro  140   LADMADVMRLLSHIKIVEEAEEAVMNAINEQDINRFEKGKEMVKLNYVAARROELKDPHCRDEMAAA
maTctn.pro  138   LADMIDVMCLIQMSSFQRTFESLKNVSNKSDIQRTYQKLGKELESLDYLAFKRQODLKSPSQRDETAGA maEctn.pro  211   RGILQKNVPILNYTASQACIQHPDVAAYKANRDLIYKQFQQAVIGISNAAQATASDDAAQHQGGSGELAY
maNctn.pro  210   RGALKNATMLYTASQAFLRHPDVAATRANRDYVEKQVQEAIAGISSAAQATSPTDEAKGHTGIG-ELAA
maTctn.pro  208   RATLKENSPLLHSICSACIEHSDVASLKASKDTVCEELQNAIDVISNASQGIQNAPAPPEPQAAT--LGS maEctn.pro  281   ALNNFDKQIIVDPLSFSEERFRPSLEERLESIISGAALMADSSCTRDDRRERIVAECNAVRQALQDLLSE
maNctn.pro  279   ALNEFDNKIIILDPMTFSEARFRPSLEERLESIISGAALMADSSCTRDDRRERMVAECNAVRQALQDLLSE
maTctn.pro  276   AFDETENLIVLNPLTVEEDVRPSLEKRLEAIISGAALIADSSCTRDIHRERIEAECNAIRQALQDLLTE maEctn.pro  351   YMGNAGRKERSDALNSAIDKMTKKTRDLRRQLRKAVMDHVSDSFLETNVPLLVLIEAAKNGNEKEVKEYA
maNctn.pro  349   DMNNTGRKEKGPPINTAIDKMTKKTRDLRRQLRKAVMDHISDSFLETNVPLLVLIEAAKSGNEKEVKEYA
maTctn.pro  346   YMSSNTGKTERSNTLNTAIVNMSKKTRDLRRQLRKALEDHISDSFLDTIVPLLVLIEAAKNGRVKELKDYA maEctn.pro  421   QVFREHANKLIEVANLACSISNNEEGVKLVRMSASQLEALCPQVINAALALAAKPQSKLAQENMDIFKEQ
maNctn.pro  419   QVFREHANKLVEVANLACSISNNEEGVKLVRMAATQIDSICPQVINAAILAARPQSKVAQDMDVFKDQ
maTctn.pro  416   AIFHEHTGRLVEVANLACSMSTNEDGIKIVREAANHLETLCPQEINAALALASRPKSQVVKNTMEMVKRT
```

Figure 19 (cont.)

```
maEctn.pro  491  WEKQVRVLTDAVDDITSIDDFLAVSENHILEDVNKCVIALQEKDVDGLDRTAGAIRGRAARVIHVVTSEM
maNctn.pro  489  WEKQVRVITEAVDDITSVDDFLSVSENHILEDVNKCVIALQEGDVDTLDRTAGAIRGRAARVIHTTNAEM
maTctn.pro  486  WEFYIHVLTEAVDDITSIDDFLAVSESHILEDVNKCHIAIRDQDADNLDRAAGAIRGRAARVAHIVAGEM maEctn.pro  561  DNYEPGVYTEKVLEATKLLSNTVMPRFLEQVEAAVEALSSDPAQPMDENEFIDASRLVYDGIRDIRKAVL
maNctn.pro  559  ENYEAGVYTEKVLEATKLLSETVMPRFAEQVEVAVEALSANVPQPFFENEFIDASRLVYNGVRDIRKAVI
maTctn.pro  556  DSYEPGAYTEGVMRNVNFLASTVIPEFVTQVNVALDALSKNSLTALDDNQFVDISKKIYDTIHDIRCSVM maEctn.pro  631  MIRTPEELEDD-SDFETEDEDVRSRTSVQTEDDQLIAGQSARAIMAQLPQEQKAKIAEQVASFQEEKSKLD
maNctn.pro  629  MIRTPEELEDDSDFEQEDADVRSRTSVQTEDRQLIAGQSARAIMAQLPQEEKAKIAEQVEIFHQEKSKLD
maTctn.pro  626  MIRTPEELEDVSDLED-DHEVRSHTSIQTEG------KIDRAKMTQLPEAEKEKIAEQVADFKKVKSKLD maEctn.pro  700  AEVSKWDDSGNDIIVLAKQMCMIMMEMTDFTRGKGPLKNTSDVISAAKKIAEAGSRMDKLGRTIADHCPD
maNctn.pro  699  AEVAKWDDSGNDIIVLAKQMCMIMMEMTDFTRGKGPLKNTSDVINAAKKIAEAGSRMDKLARAVADQCPD
maTctn.pro  689  AETEIWDDISNDIIVLAKKMCMIMMEMTDFTRGKGPLKHTTDVIYAAKMISESGSRMDVLARQIANQCPD maEctn.pro  770  SACKQDLLAYLQRIALYCHQLNICSKVKAEVQNLGGELVVSG--------------------------
maNctn.pro  769  SACKQDLLAYLQRIALYCHQLNICSKVKAEVQNLGGELIVSGTGVQSTSTTFYEVDCDVIDGGRASQLST
maTctn.pro  759  PPCKQDLLAYLEQIKFYSHQLRICSQVKAEIQNLGGELIVSA-------------------------- maEctn.pro  812  ------VDSAMSLIQAAKNLMNAVVQTVKASYVASTKYQKSQGMASINLPAVSWKM
maNctn.pro  839  HLPTCAEGAPIGSGSDSSMLDSSTSLIQAAKNLMNAVVTTVKASYVASTKYQKVYGTAAVNSPVVSWKM
maTctn.pro  801  ------LDSVTSLIQAAKNLMNAVVQTVKMSYLASTKIIRIQSSAGPRHPVVMWRM maEctn.pro  862  KAPEKKPLVKREKQDETQTKIKPASQKKHVNPVQALSEFKAMDSI
maNctn.pro  909  KAPEKKPLVKREKPEFQTRVRRGSQKKHISPVQALSEFKAMDSF
maTctn.pro  851  KAPAKKPLIKREKPEETWAAARRGSAKKKIHPVQVMSEFRGRQVY
```

Figure 21
A
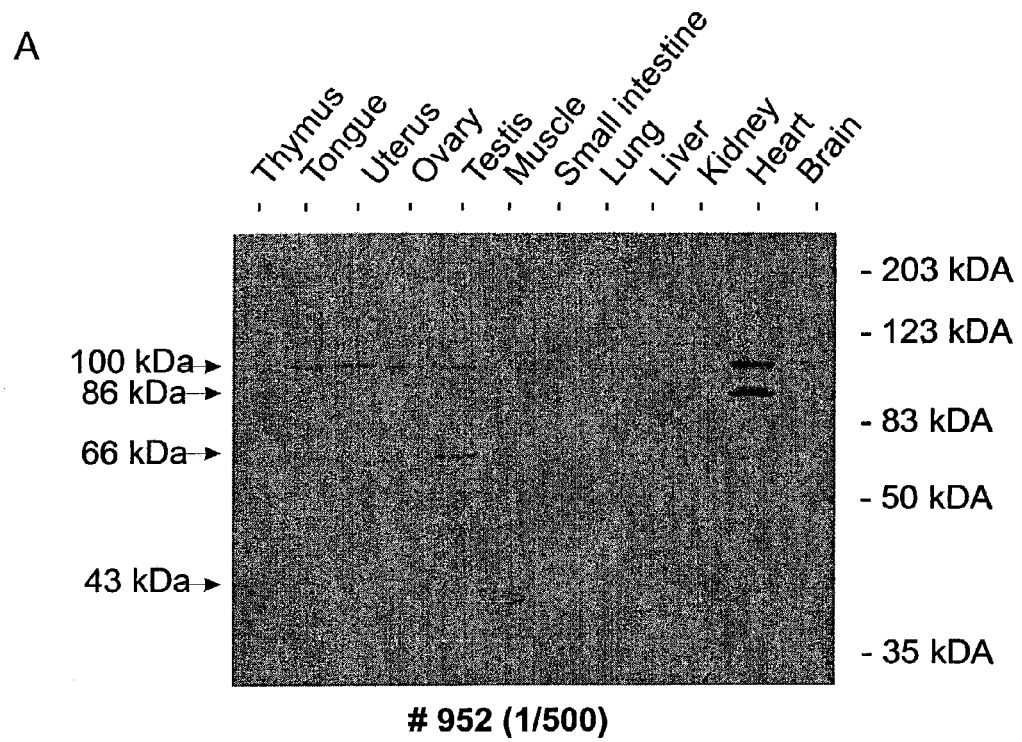
B
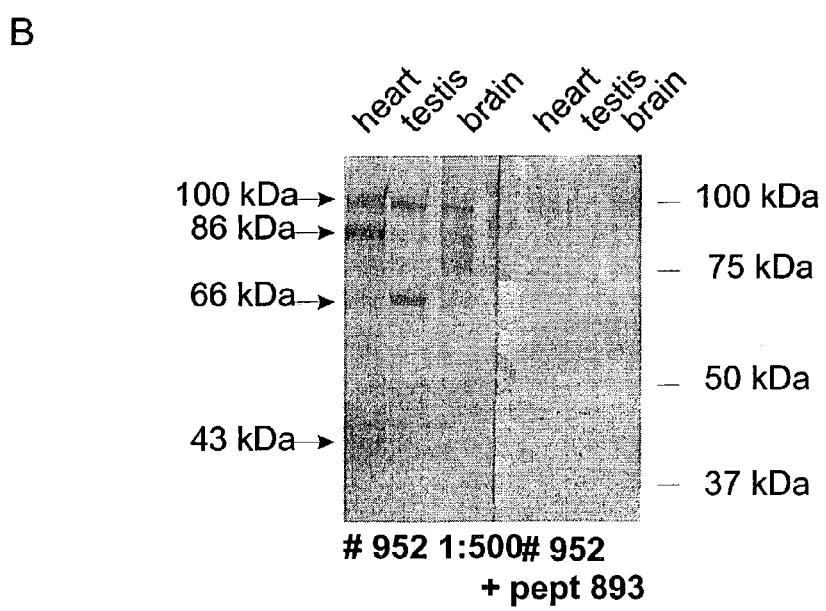

α-CATENIN EXPRESSED IN HEART AND TESTIS

CROSS-REFERENCE TO RELATED APPLICATION(S)

This application is a continuation of PCT International Application Number PCT/EP01/07392 filed Jun. 28, 2001, designating the United States of America (which itself claimed priority, inter alia, from U.S. Provisional Patent Application 60/218,309 filed Jul. 14, 2000), and published, in English, as PCT International Publication Number WO 02/04636 A1 on Jan. 17, 2002, the contents of the entirety of which is incorporated by this reference.

TECHNICAL FIELD

The present invention relates generally to the field of biotechnology, and specifically to a novel α-catenin with a new, specific expression pattern in mainly heart and testis. The invention further relates to the use of the α-catenin in prediction, diagnosis or treatment of cadherin-catenin related diseases, such as cardiomyopathies and male infertility.

BACKGROUND

The αE-catenin protein, a component of the epithelial cadherin-catenin adhesion complex, is a well-known invasion suppressor. To reach full functionality of the cadherin-catenin cell-cell adhesion complex, it is necessary to link the complex to the actin cytoskeleton. AlphaE-catenin provides this link by binding to β-catenin or plakoglobin through its amino terminal side, and by binding actin or the actin-binding molecule α-actinin through its carboxy-terminus (reviewed in Rudiger, 1998). It has been shown that loss of αE-catenin affects cell-cell adhesion and promotes tumorigenicity (Ewing et al., 1995). In many cases of invasive cells, αE-catenin defects are seen, and introduction of exogenous α-catenin can restore cell-cell aggregation and counteract invasiveness (Hirano et al., 1992; van Hengel et al., 1997; Watabe et al., 1994).

The family of α-catenins contains so far four known members. The αE-catenin protein is ubiquitously expressed, mainly in epithelial tissues. AlphaN-catenin protein has about 75% identity to αE-catenin, but is restricted in its expression to neural tissues (Hirano et al., 1992). In analogy with αE-catenin, it can also bind to β-catenin and plakoglobin and is supposed to bind α-actinin and actin. Although the vinculin protein shows much less identity (20%) to αE- and αN-catenin, it shares some similar characteristics. This protein is mainly found in focal adhesions where it forms the link to the actin cytoskeleton and binds the integrin-binding molecule talin. Vinculin is sometimes found in cell-cell contacts as well, and it may even be able to take over the function of αE-catenin, by binding to β-catenin (Hazan et al., 1997). On the other hand, vinculin has been reported to bind to a central region of αE-catenin and to be essential for apical junctional organization (Watabe-Uchida et al., 1998). Moreover, vinculin has a unique proline-rich hinge domain, which is absent in the other family members and which allows the vinculin tail to bind to the head, thus masking some "cryptic" binding sites (Johnson & Craig, 1995). For the recently reported α-catulin (Janssens et al., 1999; Zhang et al., 1998), the identity to other family members is about 25% at the amino acid level, but no functional evidence for adhesive properties was found yet. In addition to their structural role, it is becoming clear that α-catenins and vinculin also have a regulatory function in the coordination of assembly and disassembly of junctions (Rudiger, 1998), and that αN-catenin can locate to the nucleus where it inhibits β-catenin/Tcf signaling (Giannini et al., 2000).

DISCLOSURE OF THE INVENTION

The present invention relates to a novel α-catenin with about 55% identity and 70% similarity to other α-catenins. Surprisingly, the novel catenin shows a specific expression in mainly heart and testis. Moreover, it interacts more strongly with β-catenin than the known α-catenins.

In one aspect, the invention provides an isolated novel α-catenin polypeptide comprising the sequence as presented in SEQ ID NO:2 for the human molecule, or variants thereof, which variants have at least 70% identity, preferably at least 80% identity, more preferably at least 90% identity with such sequences, as measured by a BLAST search (Altschul et al. 1997). A specific embodiment of a variant is the mouse molecule of which the sequence comprises the sequence presented in SEQ ID NO:5. Preferably, the variant consists essentially of SEQ ID NO:5.

In another aspect, the invention provides a nucleic acid sequence encoding the polypeptide. A preferred embodiment is a nucleic acid sequence, comprising the sequence presented in SEQ ID NO:1 for the human molecule and SEQ ID NO:4 for the mouse molecule. Such novel α-catenin polypeptide is expressed selected tissues or organs such as heart and/or testis, possibly combined with expression in brain, kidney, liver, lung, ovary, tongue, uterus and skeletal muscle.

It is another aspect of the invention to provide the genomic organization of the gene, encoding the novel human α-catenin polypeptide. Human exon-intron boundaries have been determined and the exons have been allocated to different bacterial and P1 derived artificial chromosomes (BACs and PACs). The determination of the intronic sequences is a routine technique known to the person skilled in the art.

Still another aspect of the invention is a nucleic acid comprising the promoter region of a gene, encoding a polypeptide according to the invention. A preferred embodiment is the nucleic acid comprising the human sequence presented in SEQ ID NO:3 and the mouse sequence presented in SEQ ID NO:6. The sequences were found to contain several putative binding sites for muscle-specific transcription factors such as Nkx2.5, MEF-2 and MEF-3. By modifying this promoter sequence, or by modulating the correspondingly binding transcription factors the transcription of the novel α-catenin can be influenced.

Another aspect of the invention is the use of the novel α-catenin, or variants thereof, to modulate the cadherin-catenin related pathway. Alpha-catenin-like molecules can interact with the cadherin-catenin adhesion complex and are influencing as such the cell-cell adhesion and the β-catenin mediated signaling that is influencing the transcription of, as a non-limiting example, genes as c-myc, cyclin-D1, matrilysin, and c-jun. As the novel α-catenin of the invention is more strongly interacting with β-catenin than any other of the known α-catenin like molecules, it can be useful to use this molecule, or its β-catenin binding domain, or a polypeptide comprising this β-catenin binding domain either to block the α-catenin/β-catenin interaction, or to restore a deficient interaction. In a preferred embodiment, the cadherin-catenin related pathway is specifically modulated in selected tissues or organs such as heart and/or testis, eventually combined with modulation of the pathway in brain, kidney, liver, skeletal muscle.

Still another aspect of the invention is the use of the novel α-catenin, or variants thereof, to treat cadherin-catenin related diseases. Such diseases include, but are not limited to cancer, cardiomyopathies including dilated cardiomyopathy, and male infertility.

Still another aspect of the invention is the use of the nucleic acid sequence encoding the novel α-catenin, or fragments thereof, or the gene encoding the novel α-catenin or fragments thereof for the diagnosis of cadherin-catenin related diseases, or for predicting the likelihood of developing the cadherin-catenin related diseases. A preferred embodiment is the use of the nucleic acid or the gene for predicting the likelihood and/or diagnosis of cancer. Another preferred embodiment is the use of the nucleic acid or the gene for predicting the likelihood and/or diagnosis of cardiomyopathies including dilated cardiomyopathy, and male infertility. The nucleic acid sequence, gene, or fragments thereof can be used for detecting mutations and/or for quantifying messenger RNA expression levels, by techniques know to the person skilled in the art, such as but not limited to PCR, DNA-DNA hybridization, DNA-RNA hybridization or fluorescent in situ hybridization ("FISH").

Still another aspect of the invention is the use of the nucleic acid sequence encoding the novel α-catenin, or functional fragments thereof, for the treatment of cadherin-catenin related diseases. Indeed, the nucleic acid sequence can be incorporated in a vector suitable for gene therapy. Such vectors are known to the person skilled in the art and do include, but are not limited to retroviral vectors, adenoviral vectors, adenovirus-associated viral vectors and lentiviral vectors.

Another aspect of the invention is antibodies against a novel α-catenin according to the invention. Preferably, the antibodies are monoclonal antibodies. One embodiment is a monoclonal antibody deposited at BCCM under the number LMBP 5537CB. Another embodiment is a monoclonal antibody deposited at BCCM under the number LMBP 5728CB.

Still another aspect of the invention is the use of the antibodies to treat cadherin-catenin related diseases. A preferred embodiment is the use of the antibodies whereby the disease is cancer. Another preferred embodiment is the use of the antibodies whereby the disease is a cardiomyopathy including dilated cardiomyopathy. Still another preferred embodiment is male infertility.

Still another aspect of the invention is the use of the antibody for the diagnosis of cadherin-catenin related diseases, or for predicting the likelihood of developing the cadherin-catenin related diseases. A preferred embodiment is the use of the antibodies for predicting the likelihood and/or diagnosis of cancer. Another preferred embodiment is the use of the antibodies for predicting the likelihood and/or diagnosis of cardiomyopathies including dilated cardiomyopathy, and male infertility. Antibodies can be used in tests such as a Western blot or an ELISA test, known to the person skilled in the art, to compare expression levels of the protein.

Definitions

Fragment of a nucleic acid or gene, as used here means any fragment that can be used as specific probe in hybridization reaction or specific primer in PCR reaction.

Functional fragment of the novel α-catenin means a fragment encoding a polypeptide that comprises a functional β-catenin binding domain.

Promoter region of a gene as used here means a region that is sufficient to obtain transcription of the normally transcribed regions of the gene. Promoter region of a gene, encoding a polypeptide according to the invention means a promoter region that is in a natural, non-recombinant situation linked to a gene encoding a polypeptide comprising the sequence presented in SEQ ID NO:2, or a variant thereof, which variant has at least 70% identity, preferably at least 80% identity, more preferably at least 90% identity with the sequence.

Cadherin-catenin related disease is a disease that is caused by overexpression, underexpression or dysfunction of one or more compounds of the cadherin-catenin cell adhesion complex and the related β-catenin mediated signaling pathway and includes, but is not limited to cancer, cardiomyopathies including dilated cardiomyopathy, and male infertility.

β-catenin mediated signaling pathway as used here means the pathway that is influenced by protein complexes in which β-catenin takes part.

Gene as used here, means the genomic structure of the gene, including the promoter, the terminator and the complete transcribed sequence, which includes both exonic and intronic sequences.

BRIEF DESCRIPTION OF THE TABLES AND FIGURES

Table 1: List of genomic Genbank submissions containing CTNNA3-specific sequences, complemented with proprietary data on BAC 162A20 and PAC 320B7.

Table 2: Sequences of CTNNA3 exon-intron and intron-exon boundaries. Coding sequences are shown in capital letters. The open reading frame is indicated, with translation to amino acids on top of the sequence. Position of exon boundaries in the cDNA sequence is annotated under the sequence. All introns start with gt and end with ag, conform to the rules for exon boundaries (Mount, 1982). Intron sizes are indicated as minimum size, based on the length of intronic sequences obtained so far.

Table 3: Overview of CTNNA3 exon-specific primers. For each exon, primer sequences in flanking intronic sequences are given, with the length of the PCR product (in bp), the optimum $MgCl_2$ concentration and the recommended annealing temperature (A.T.) to be used for genomic PCR.

FIG. 1: Isolation of the novel human αT-catenin cDNA by two consecutive 5'-RACE experiments. (A) On the basis of one single EST sequence (IMAGE clone #728263), primers for 5'-RACE were designed and used to obtain a product of 1,011 bp. As this fragment was still lacking a suitable start codon, a second 5'-RACE was performed, which yielded a product of 1,306 bp containing the start codon. By aligning sequences from these clones, a full-length cDNA sequence of 3,024 bp wa amino acid residues (boxed). Percentage identity (B) and similarity (C) by MegAlign sequence comparison (DNAStar, Madison, Wis.) after alignment of the protein sequences by the CLUSTALW method (Higgins & Sharp, 1989) and distance calculation with GCG software (www.BEN.ac.be). GenBank accession numbers of the used human sequences are M33308 (vinculin), U97067 (α-catulin), AF091606 (αT-catenin), D14705 (αE-catenin) and M94151 (αN2-catenin).

Figure 2:
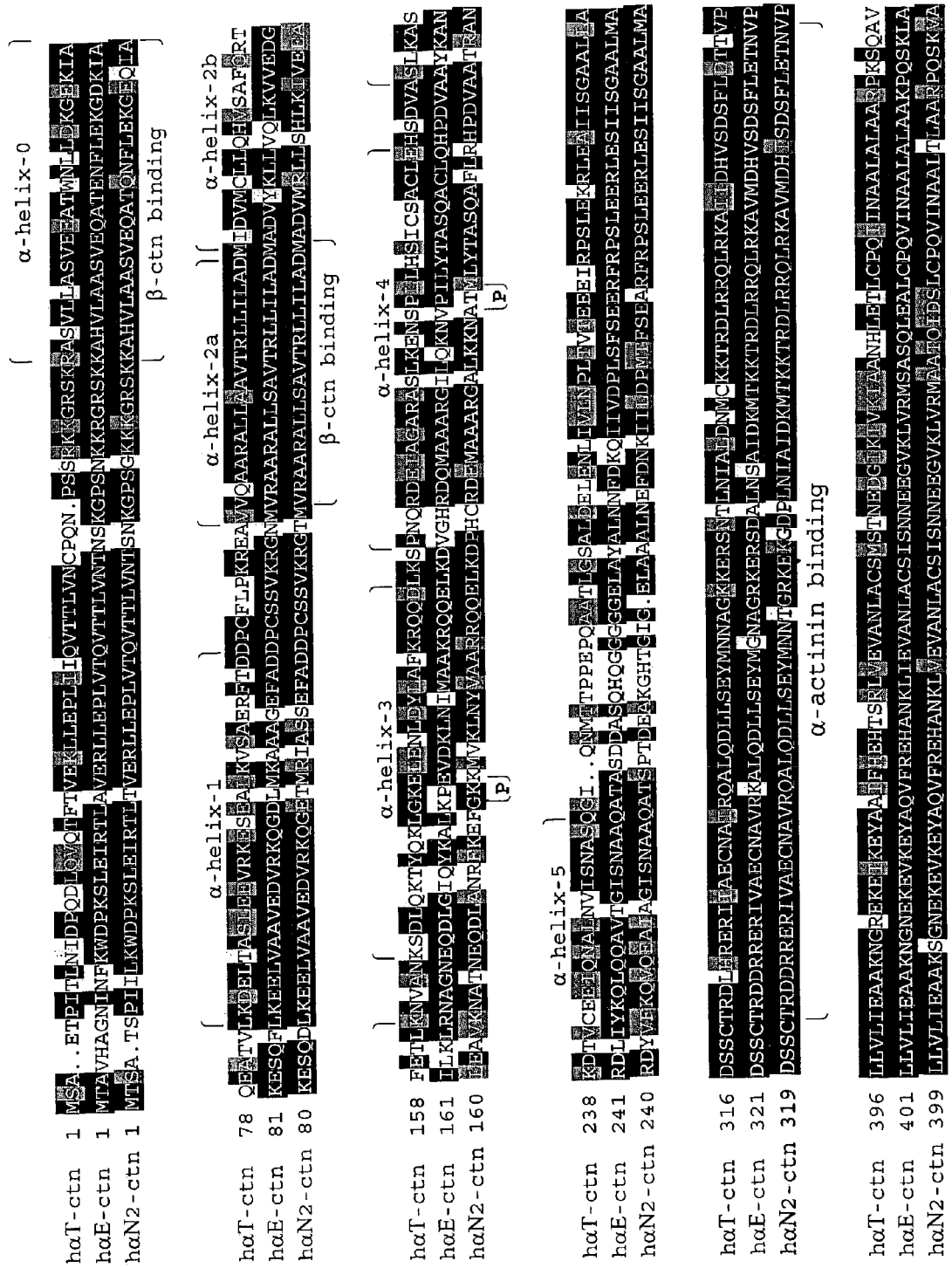

FIG. 2: Amino acid sequence alignment of the human α-catenins. MegAlign sequence comparison (DNAStar, Madison, Wis.) after alignment of the protein sequences by the CLUSTALW method (Higgins & Sharp, 1989), shaded by the Boxshade server (http://ulrec3.unil.ch/softward/BOX_form.html). Partial 3-dimensional structure as, determined for αE-catenin (Pokutta & Weis, 2000) is shown by the location of the respective α-helices. Two characteristic proline residues, inducing a kink in the α-helices, are marked with "P". Annotated domains are: the β-catenin binding domain as determined by Pokutta & Weis (2000) and by Huber et a/. (1997), the α-actinin binding domain (Nieset et al., 1997), the amphiphatic helices possibly responsible for actin binding (Rudiger, 1998) and the position of the alternatively spliced insert (Claverie et al., 1993), which is generally found for αN-catenin, but rarely for αE-catenin. GenBank accession numbers of the used sequences are AF091606 (αT-catenin), D14705 (αE-catenin) and M94151 (αN2-catenin).

FIG. 3: Chromosomal localization of the CTNNA3 gene, encoding human αT-catenin. (A) Fluorescence in situ hybridization with a specific PAC clone; arrows point at the positive signal; (B) G-banding by DAPI staining of the same chromosomes as shown in (A); (C) Fine mapping by Genebridge4 PCR analysis reveals the CTNNA3 location between the markers as shown; the obtained PCR pattern was:
00000000100000000000001012000011001010001100000100000000000000010010001010000 001110000000100, and was used as such for analysis on Webpage http://www.hgmp.mrc.ac.uk/cgi-bin/contig/rhmapper.pl.

FIG. 4: Positioning of exon-exon boundaries (boxed) in the protein sequences of human αT-catenin and αE-catenin. Three boundaries in the αT-catenin sequence that do not coincide with αE-catenin are shown in bold. Indicated numbers refer to exons of αT-catenin (see also Table 1, Table 2 and FIG. 5).

Figure 5:
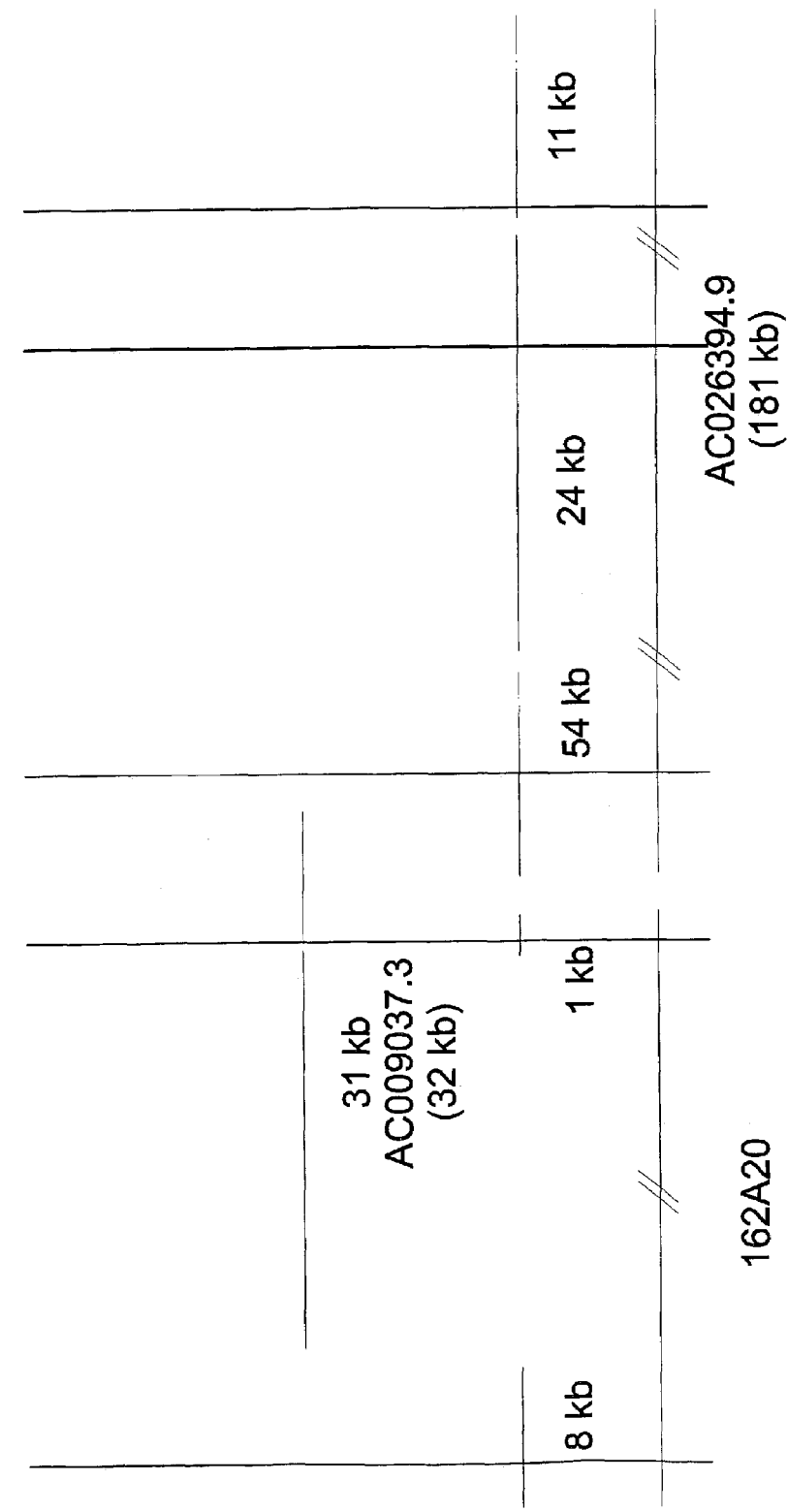
Figure 5:
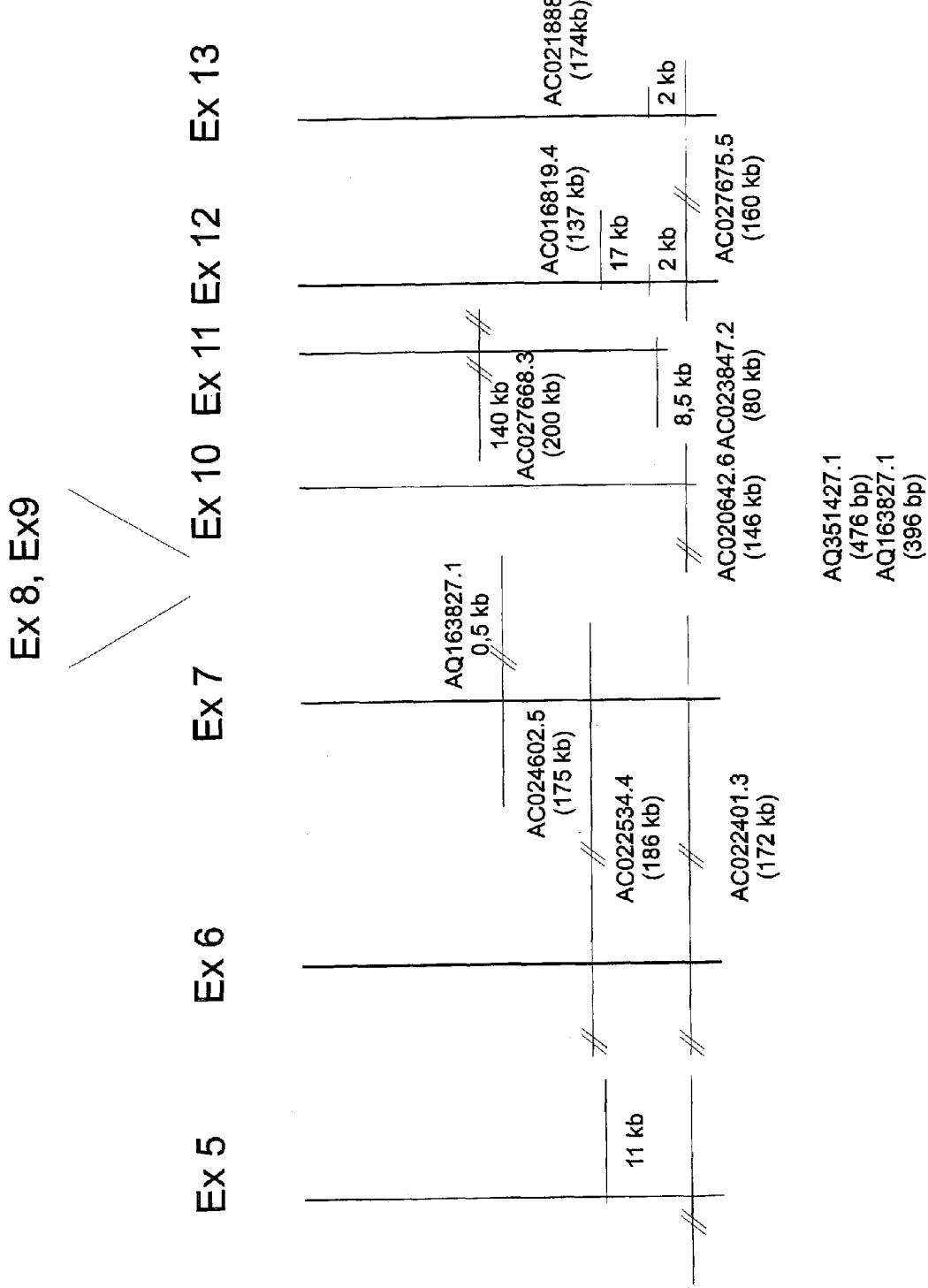
Figure 5:
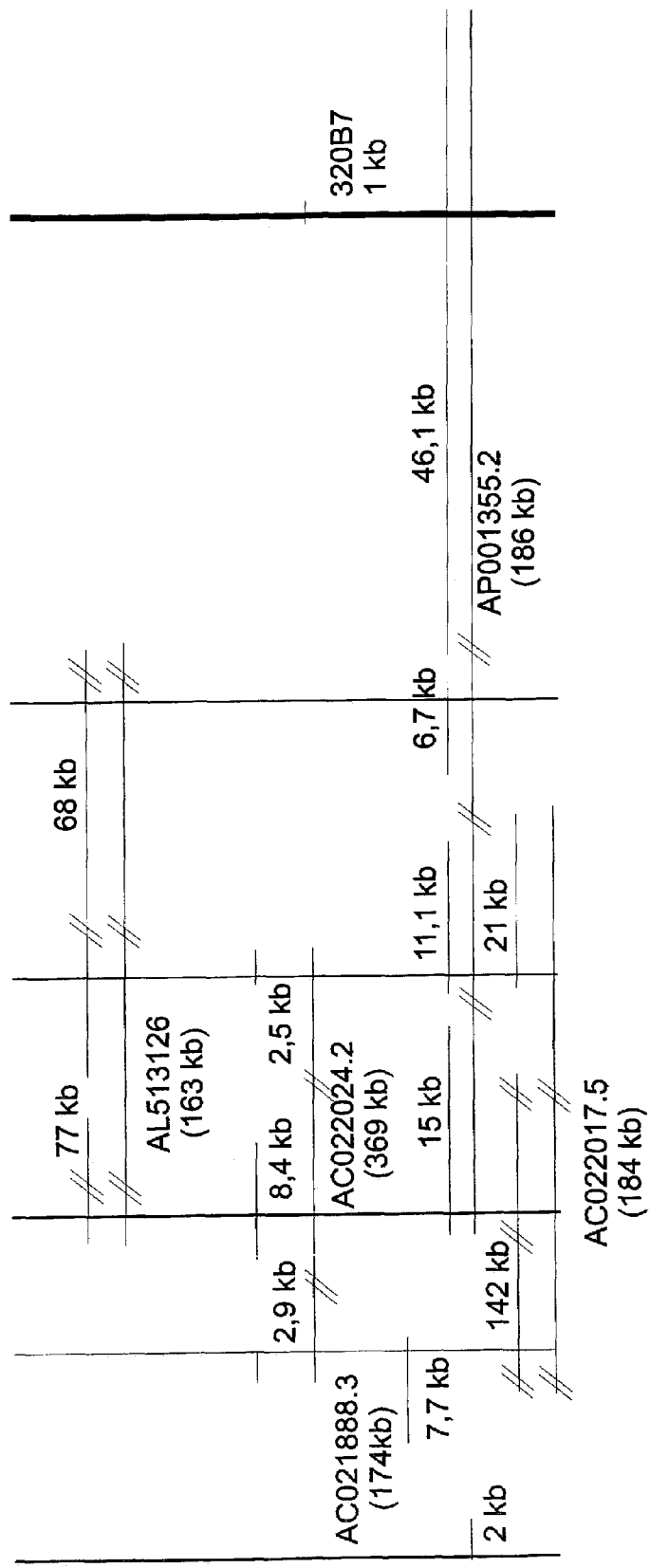

FIG. 5: Overview of BAC and PAC clones covering the human CTNNA3 gene. Clones 162A20 and 320B7 are, respectively, a BAC and PAC clone isolated by us. All other sequences were obtained from GenBank and are annotated with their respective Accession Numbers. Lengths of contig sequences, in which a match is found with one or more CTNNA3 exons (indicated by "Ex" followed by the appropriate exon number), are mentioned in kilobase pairs (kb) or base pairs (bp). BAC or PAC clone lengths are mentioned between brackets and refer to the number of sequenced bp of the respective clones (GenBank including HTGS database, sequence versions as indicated).

Figure 6:
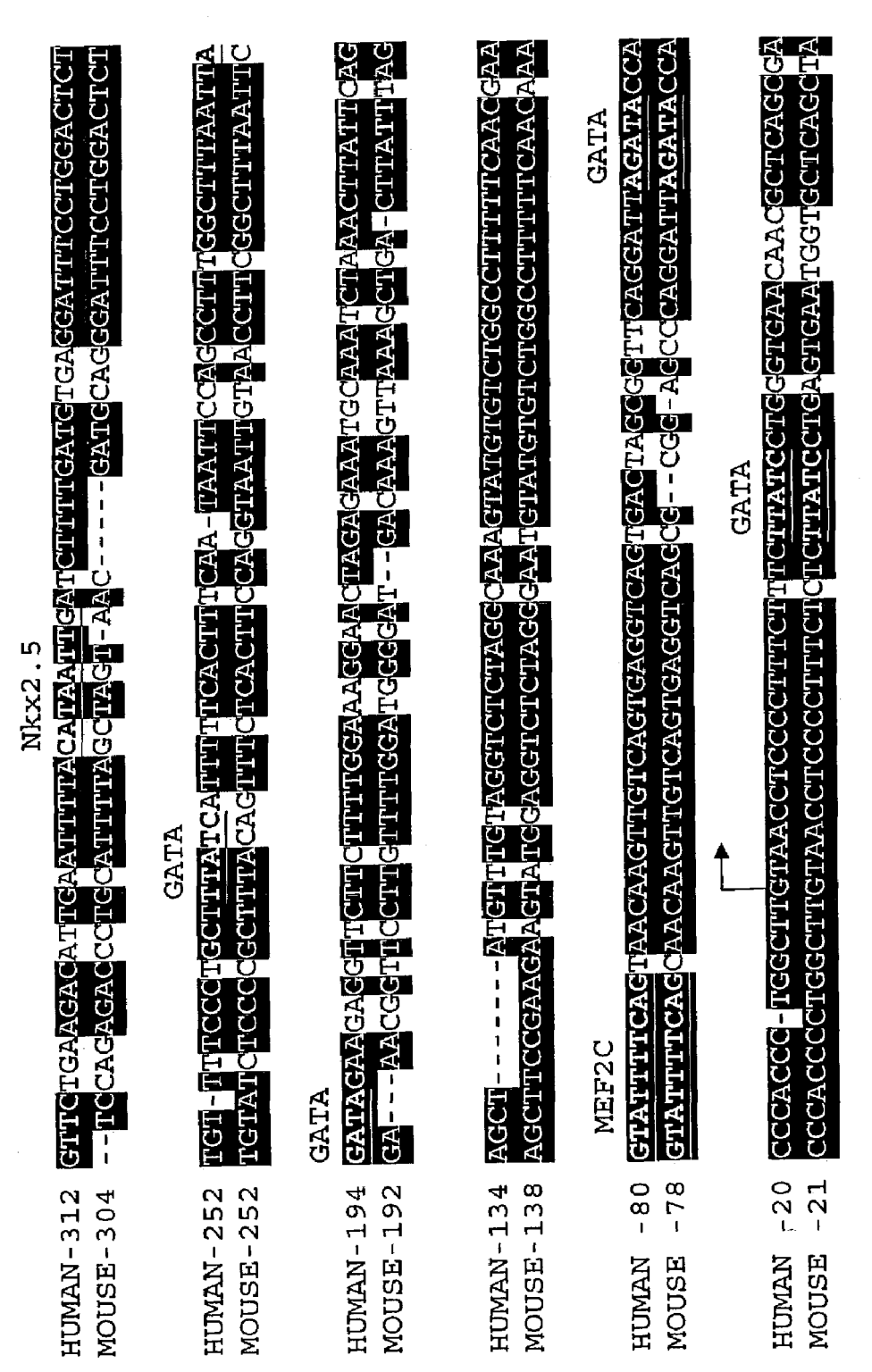

FIG. 6: (A) The human αT-catenin promoter sequence as determined from a human genomic BAC clone (clone 162A20). The sequence-listed comprises 1,237 bp of the upstream sequences, the sequence of exon-1 (bp 1238-1433) and part of intron-1 (bp 1434-1740). Several transcription factor binding sites as predicted by the Matinspector transcription factor binding site search program (Quandt et al., 1995), are indicated in bold and underlined. (B) Alignment of human and mouse αT-catenin promoter sequences, as determined from the human genomic BAC clone 162A20 and mouse genomic BAC clone 164N16. Transcription factor binding sites are indicated. The sequence conservation of the MEF2C site and two GATA-binding sites is striking. The arrow indicates the transcription initiation site.

FIG. 7: Interaction between αT-catenin and β-catenin/plakoglobin in the yeast two-hybrid system. (A) Introduction in the two-hybrid system by cotransformation of the respective fusion constructs. Plasmids used for cotransformation were pGBT9-ATCTN(179-2860), pGBT9-αctl(50-2264), pGBT9-αECTN, pGBT9-αNCTN, pGAD424-ATβctn and pGAD424-Plakoglobin(227-2340), followed by XGAL staining of colonies on SD plates lacking leucine, tryptophan and histidine; pVA3 and pTD1 are control bait and prey plasmids (Clontech): they code for interacting fusion proteins derived of murine p53 and SV40 large T-antigen, respectively. (B) Quantification of interaction strength between β-catenin and either αE- or αT-catenin in the yeast two-hybrid system. β-Galactosidase activity was measured using CPRG as a substrate. Two different yeast strains and corresponding bait plasmids were used: the L40 yeast strain which was cotransformed with either pLexMG-αEctn (1) or pLexMG-αTctn (2) plus in each case pGAD424-βctn, and the Y190 yeast strain cotransformed with either pGBT9-αEctn (3) or pGBKT7-αTctn (4) plus in each case pGAD424-ATβctn. In both systems, the interaction between αT-catenin and β-catenin was found to be about 4 times stronger than the one between αE-catenin and β-catenin. (C) Confirmation of αT-catenin/β-catenin interactions by co-immunoprecipitation (IP) from HEK-293 cells transfected with plasmid pEF6MH-ATCTN(1-2860), encoding Myc-tagged αT-catenin. In the Western blots at the left, which serve as controls for efficient transfection, αT-catenin was detected by monoclonal antibody 892_24D2S and β-catenin by a polyclonal antibody (Sigma). The IP results at the right were obtained either with monoclonal anti-β-catenin antibody (Transduction) or with monoclonal anti-Myc antibody 9E10 (Oncogene, Cambridge, Mass.). SDS-PAGE was followed by Western blotting. A mixture of both antibodies was then used to probe this blot. In mock transfected cells, only β-catenin was detected as expected (data not shown). (D) Confirmation of αT-catenin/β-catenin interactions by co-immunoprecipitation (IP) from mouse tissues. IP from mouse testis and heart was performed with polyclonal antibody #952, specific for αT-catenin, and with a polyclonal antibody specific for β-catenin (Sigma). After Western blotting of total lysates (at the left) and coimmunoprecipitates (at the right), αT-catenin and β-catenin were detected by use of the same antibodies.

Figure 8:
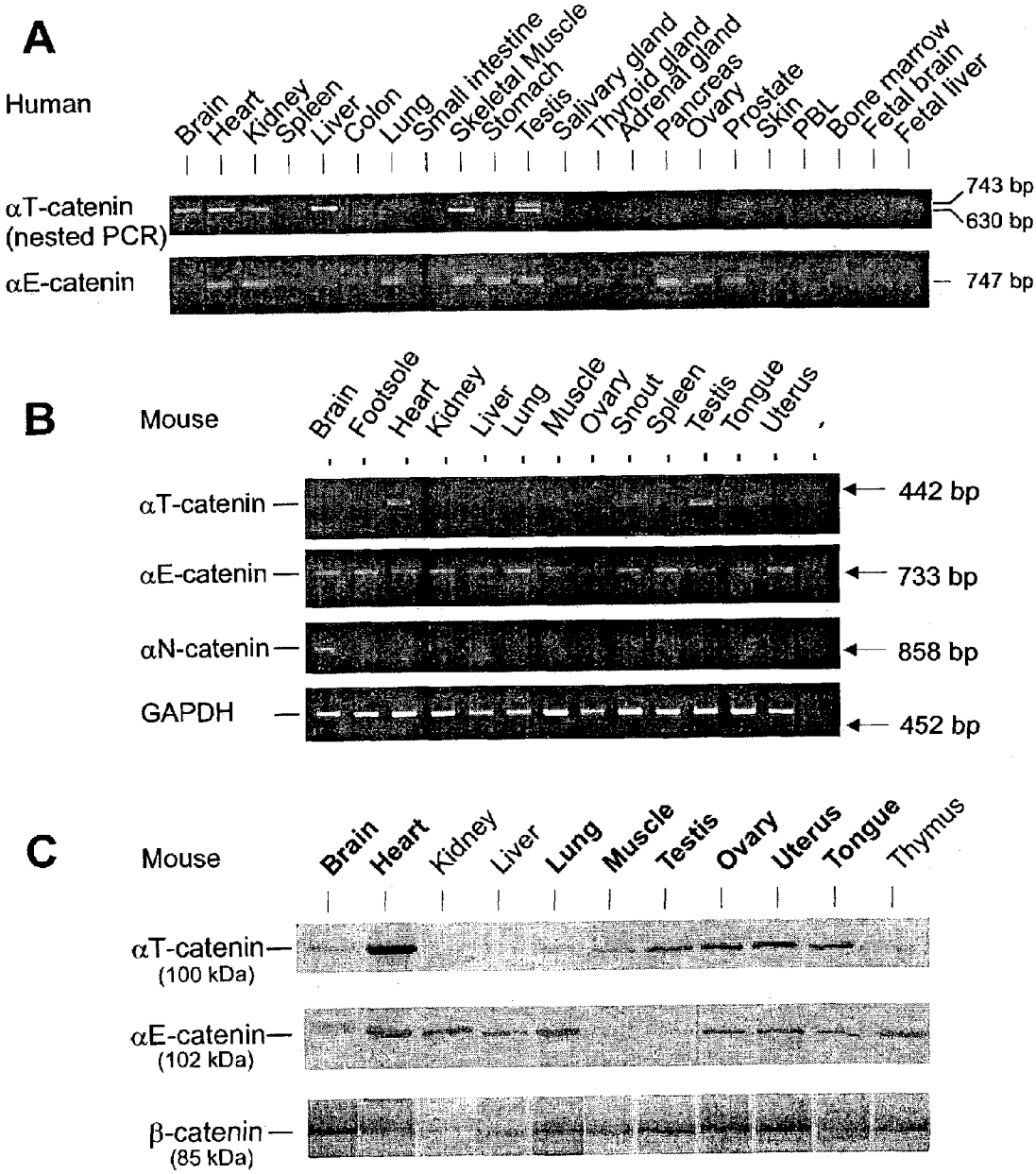

FIG. 8: Tissue-specific expression patterns of αT-catenin. (A) Rapid-scan RT-PCR expression analysis of human αT-catenin and αE-catenin mRNAs. The specific 743-bp product of the first reaction was visible in heart, testis and skeletal muscle (not shown). After nested PCR, this first product of 743 bp is still visible, whereas the nested PCR product of 630 bp is detectable in the same three samples and a few more (brain, kidney, liver, fetal liver). PCR with αE-catenin-specific primers (yielding a 747-bp product) reveals expression in most tissues. PBL, peripheral blood lymphocytes. (B) RT-PCR analysis of αE-catenin, αT-catenin and αN-catenin mRNAs in mouse organs. GAPDH mRNA analysis served as a positive control. (C) Western blot analysis of αT-catenin, αE-catenin and β-catenin protein expression in various mouse organs. For detection of αT-catenin, polyclonal serum #952 was applied. In brain tissue, the 104-kDa band revealed by anti-αE-catenin corresponds to cross-reacting αN2-catenin protein.

FIG. 9: Immunolocalization of αT-catenin in human tissues. (A) Frozen section of human heart stained with 892_24D2S monoclonal antibodies, showing localization of αT-catenin protein at intercalated discs of cardiac myocytes. (B) Enlarged detail of (A). (C) Frozen cross-section of human testis seminiferous tubules stained with 892_24D2S monoclonal antibodies, showing localization of αT-catenin protein in presumptive peritubular myoid cells at the basement membrane of seminiferous tubules. (D) Enlarged view of human testis staining with arrowhead pointing to a peritubular myoid cell.

Figure 10:
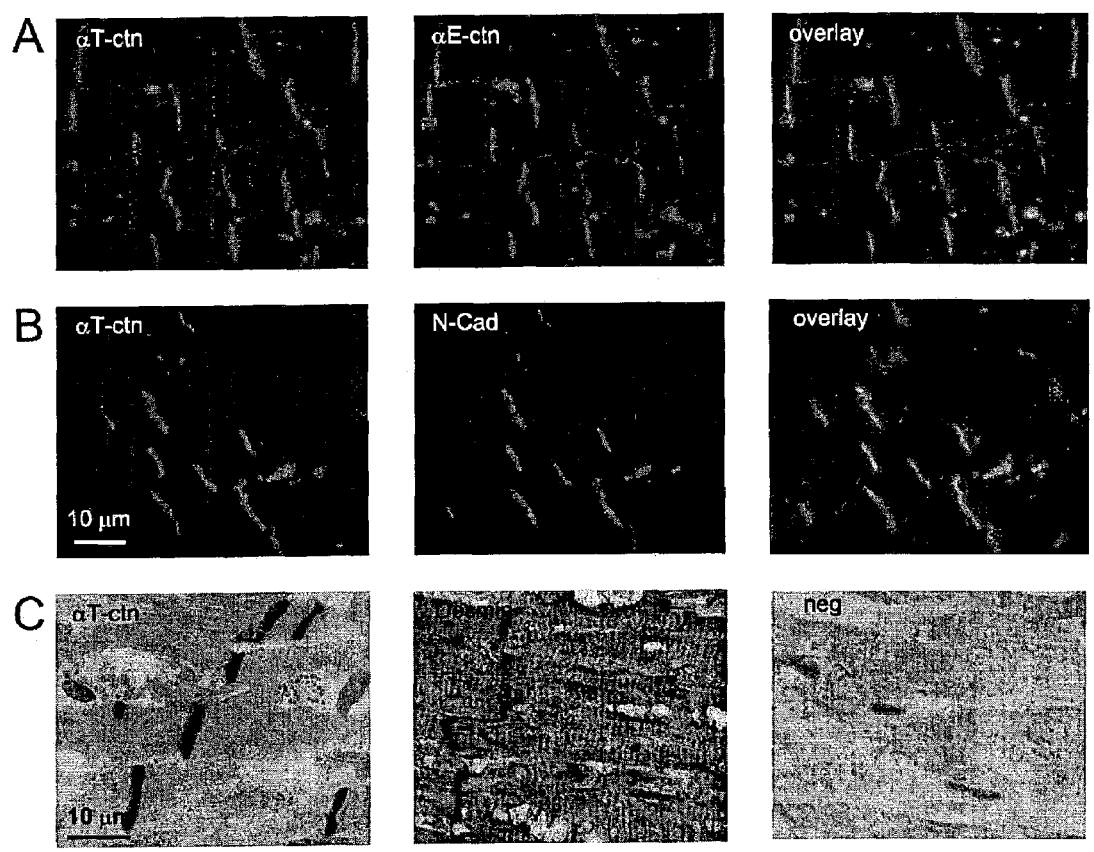

FIG. 10: Immunolocalization of αT-catenin in cryosections of human heart. (A) Double immunofluorescent staining of αT-catenin (monoclonal antibody 892_24D2S) and αE-catenin (polyclonal antibody) shows colocalization of the α-catenin proteins at intercalated discs of cardiomyocytes. (B) Double immunofluorescent staining of αT-catenin (polyclonal antibody #952) and N-cadherin (monoclonal antibody) shows colocalization at intercalated discs of cardiomyocytes. (C) Immunohistochemical staining for αT-catenin (monoclonal antibody 892_24D2) or desmin (monoclonal antibody 33) shows that αT-catenin is localized at the intercalated discs of cardiomyocytes, while desmin is present also at Z-discs. In the negative control (neg), only secondary antibody was used.

Figure 11:
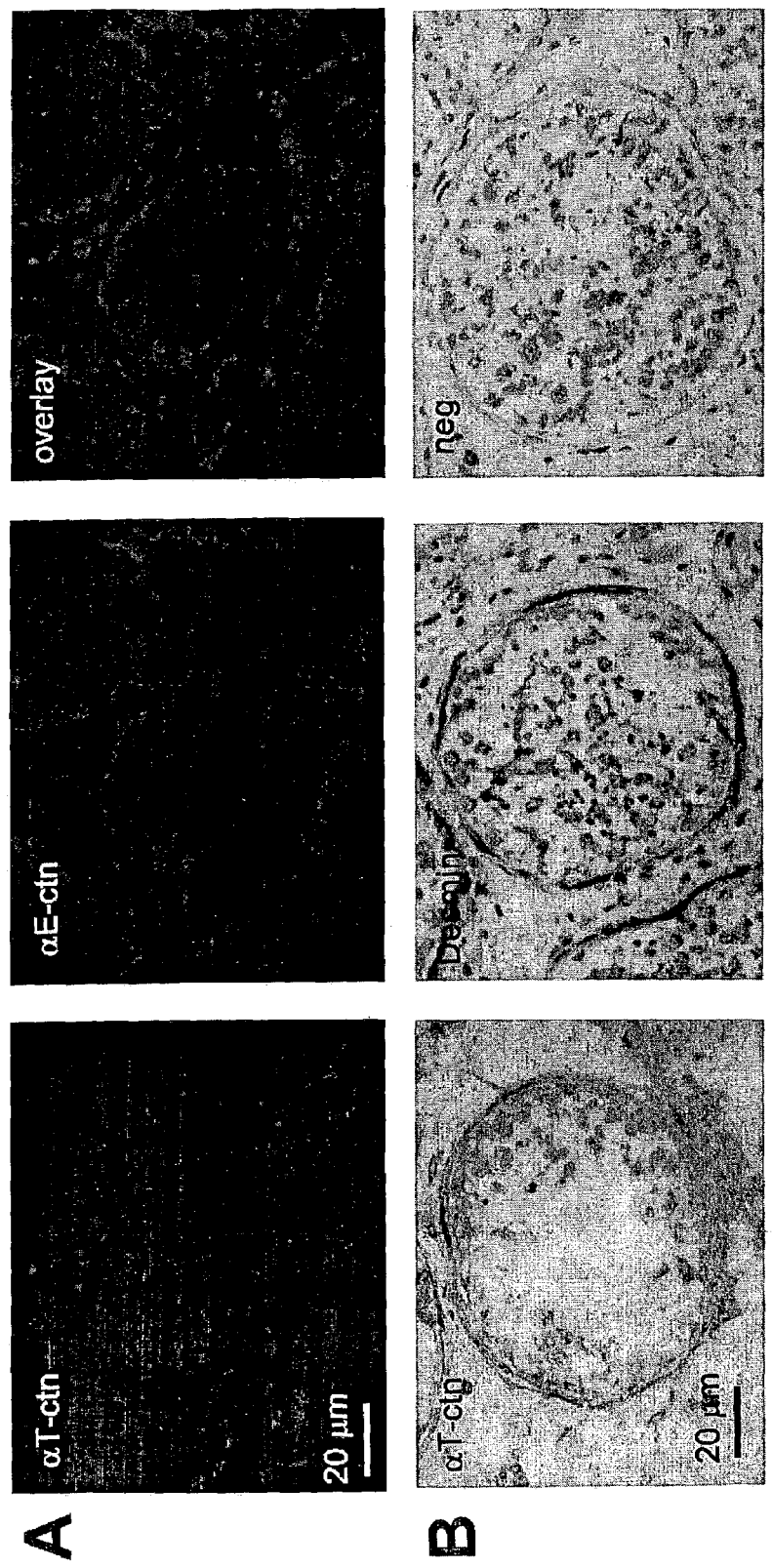

FIG. 11: Immunolocalization of αT-catenin in cryosections of human testis. (A) Double immunofluorescent staining of αT-catenin (monoclonal antibody 892_24D2) and αE-catenin (polyclonal antibody) shows differential localization of these two related proteins. The αT-catenin is present in peritubular cells, clearly separated from αE-catenin, which is present in cells within the seminiferous tubules. (B) Immunohistochemical staining of consecutive sections for αT-catenin (monoclonal antibody 892_24D2) and desmin (monoclonal antibody 33) demonstrates that αT-catenin is localized in desmin-expressing peritubular myoid cells. In the negative control (neg), only secondary antibody was used.

Figure 12:
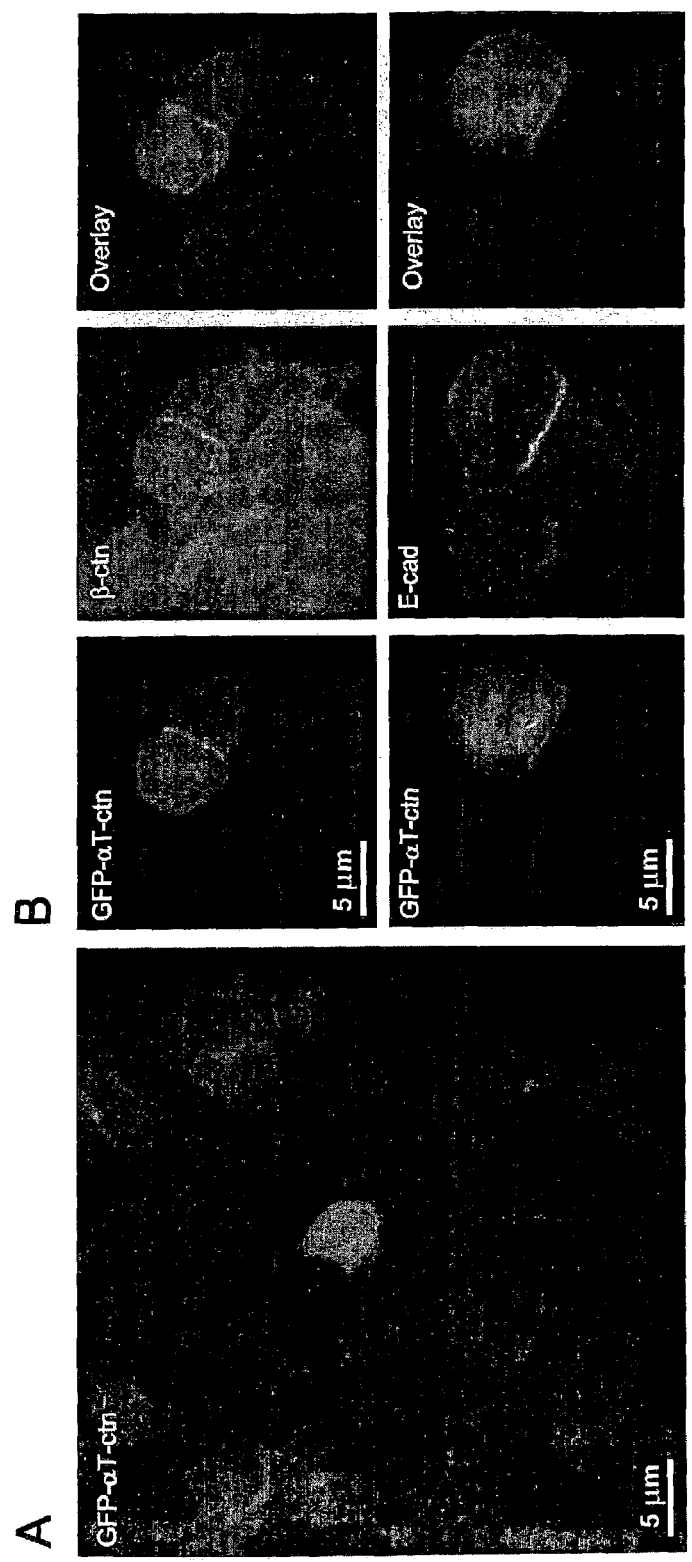

FIG. 12: Transient overexpression of αT-catenin in α-catenin-negative HCT-8/R1 colon carcinoma cells restores cadherin/catenin-mediated cell-cell adhesion. At 10 h after transfection with pE/L-GFP-ATCTN plasmid and simultaneous infection with ΔA36R vaccinia virus, opposing cells expressing GFP-αT-catenin show increased fluorescence at their common cell-cell contacts (A). This results in recruitment of β-catenin and E-cadherin to the same sites (B).

Figure 13:
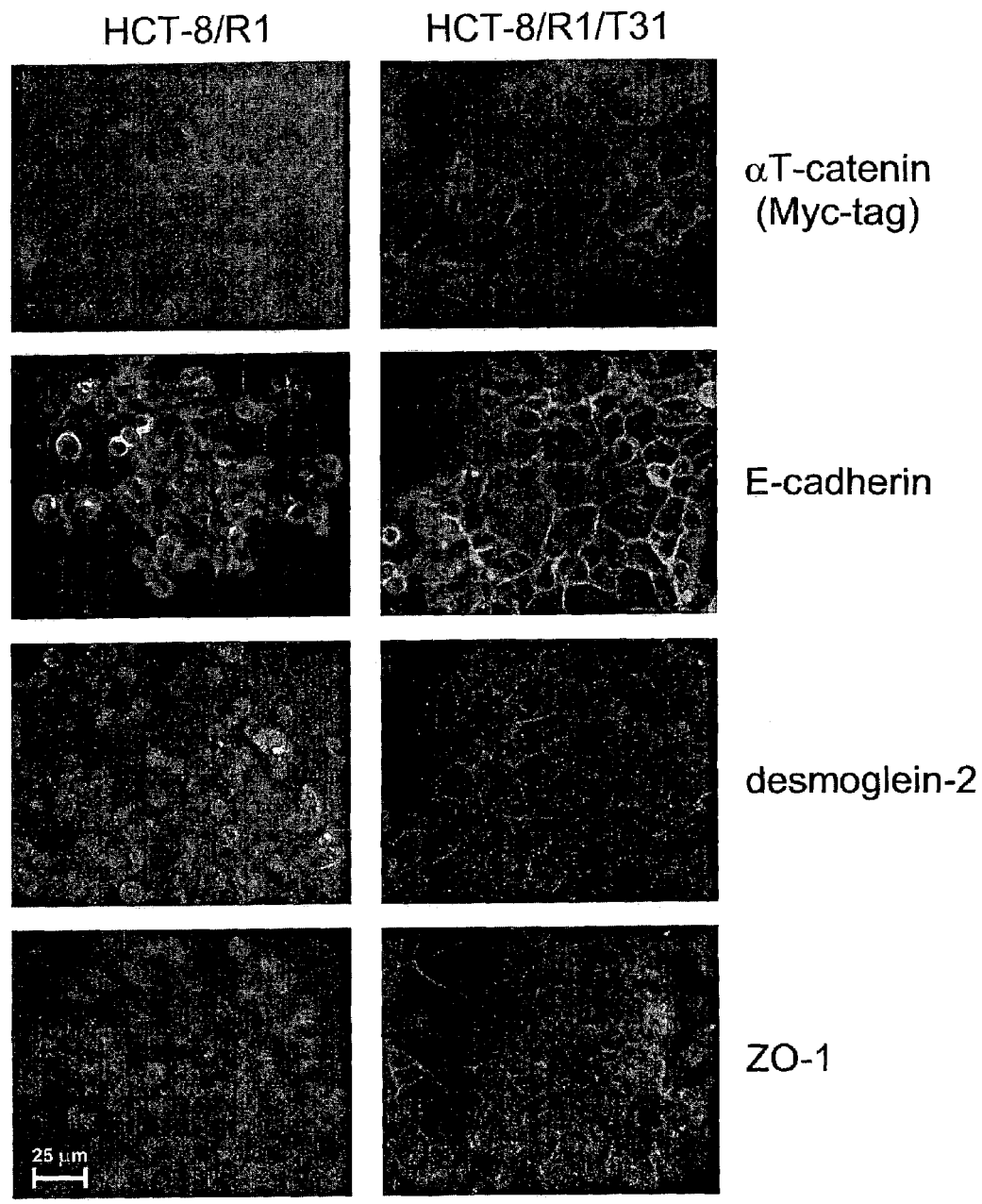

FIG. 13: Relocalization of multiple cell-cell adhesion components in stably transfected colon cancer cells, expressing Myc-tagged αT-catenin. The α-catenin-negative parental HCT-8/R1 cells (left panels) were compared to the cloned transfectant HCT-8/R1/T31 (right panels). Cells were stained for the Myc tag (exogenous αT-catenin), for E-cadherin, desmoglein-2 or ZO-1 antigens.

Figure 14:
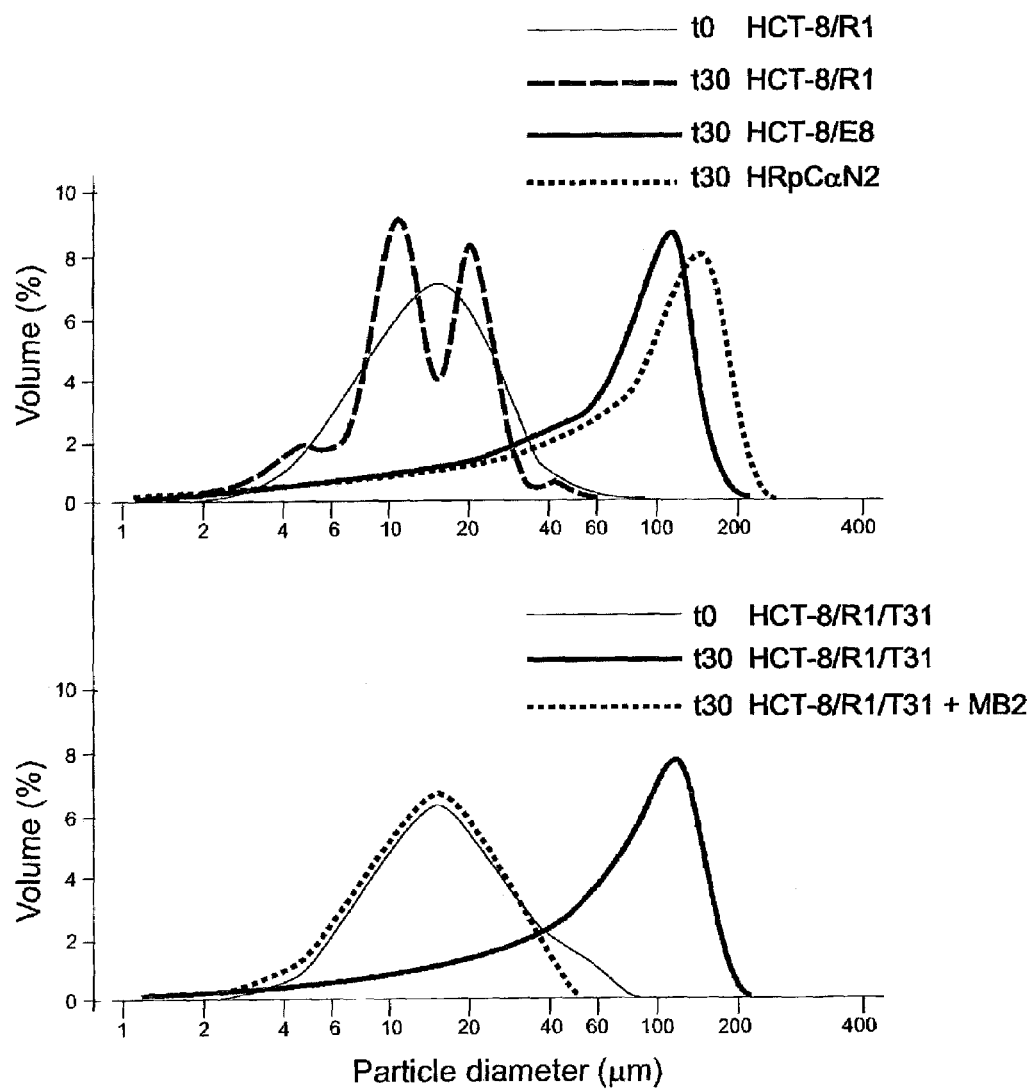

FIG. 14: Fast aggregation of α-catenin-negative HCT-8/R1 colon cancer cells is restored upon stable transfection with αT-catenin cDNA. After preparation of single-cell suspensions, cell aggregation was measured by determination of the volume % distribution in function of the particle diameter at the starting point (t0) and after 30 min (t30). HCT-8/R1, HCT-8/E11R1 and HCT-8/E8 cells were all obtained by subcloning HCT-8 cells, but only HCT-8/E8 cells express endogenous αE-catenin. HRpCαN2 is a cloned transfectant of HCT-8/E11R1 cells expressing exogenous αN-catenin (van Hengel et al., 1997); HCT-8/R1/T31 is a cloned transfectant of HCT-8/R1 cells expressing exogenous αT-catenin. MB2 is a monoclonal E-cadherin blocking antibody.

FIG. 15: Slow aggregation and compaction of HCT-8 colon cancer cells on semi-solid agar. Images of two representative cultures were taken 24 h after seeding single-cell suspensions of the indicated cell lines. No aggregation is seen in cultures of either the untransfected α-catenin-negative HCT-8/R1 cells, or the control transfectant HCT-8/R1/1743 (also α-catenin-negative). Cells expressing either endogenous αE-catenin or exogenous αN-catenin (see, also, legend to FIG. 8) form small aggregates, whereas cells expressing exogenous αT-catenin form compacted large aggregates.

Figure 16:
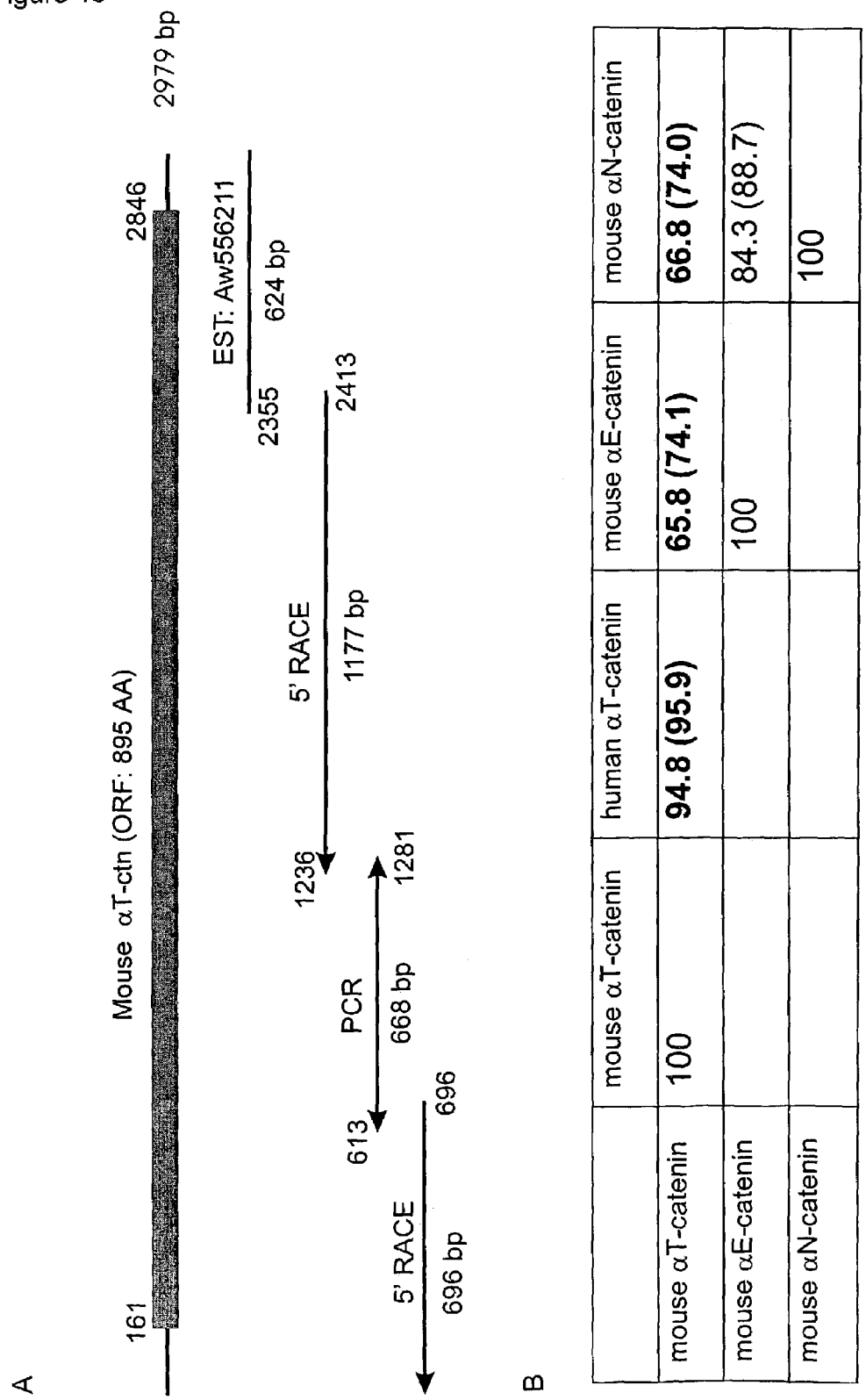

FIG. 16: Isolation of the novel mouse αT-catenin cDNA by consecutive 5'-RACE and RT-PCR experiments. (A) On the basis of one single EST sequence (GenBank Accession No. AW556211), primers for 5'-RACE were designed and used to obtain a product of 1,177 bp. As this fragment was still lacking a suitable start codon, an RT-PCR was performed using primers MCB2335 and MCB2567. This yielded a product of 684 bp of which 668 bp were new sequences. A second 5'-RACE was performed to obtain a 696-bp fragment containing the start codon. By aligning sequences from these clones, a full-length cDNA sequence of 2,979 bp was obtained, containing an open reading frame of 895 amino acid residues (boxed). (B) Percentages of identity (and similarities) between mouse αT-catenin, human αT-catenin and other mouse α-catenins, after alignment of the protein sequences by the CLUSTALW method (Higgins & Sharp, 1989) and distance calculation with GCG software (www.BEN.ac.be). GenBank accession numbers of the used sequences are AF091606 (human αT-catenin), AF344871 (mouse αT-catenin), NM_009818 (mouse αE-catenin) and NM_009819 (mouse αN-catenin).

FIG. 17: The full-length mouse αT-catenin clone pGEMTeasy-maTctn(1-2979) was expressed in an in vitro coupled transcription and translation reaction, using the TNT® Coupled Reticulocyte Lysate System (Promega). The in vitro synthesized proteins were analyzed by Western blotting and compared with endogenous αT-catenin protein in mouse heart and testis. (A) For detection of αT-catenin, polyclonal serum #952 was applied. As a negative control we used the TNT product of human cDNA encoding p120$^{ctn}$ isoform 3B (Keirsebilck et al., 1998). (B) TNT products of human and mouse αT-catenin were compared with endogenous αT-catenin protein in lysates of human and mouse heart. The αT-catenin proteins were analyzed by Western blotting and detected with either the polyclonal serum #952 (at the left) or with the monoclonal antibody 893_32C6S (at the right).

FIG. 18: Amino acid sequence alignment of the human and mouse αT-catenin. The sequences were aligned using the CLUSTALW program (Higgins & Sharp, 1989). Alignments were shaded using the Boxshade server. GenBank accession numbers of the used sequences are AF091606 (human αT-catenin) and AF344871 (mouse αT-catenin). Arrows indicate the amino-terminal β-catenin binding domains (Pokutta and Weis, 2000).

FIG. 19: Amino acid sequence alignment of the mouse α-catenins. The sequences were aligned using the CLUSTALW program (Higgins & Sharp, 1989). Alignments were shaded using the Boxshade server. GenBank accession numbers of the used sequences are NM_009818 (mouse αE-catenin), NM_009819 (mouse αN-catenin) and AF344871 (mouse αT-catenin).

Figure 20:
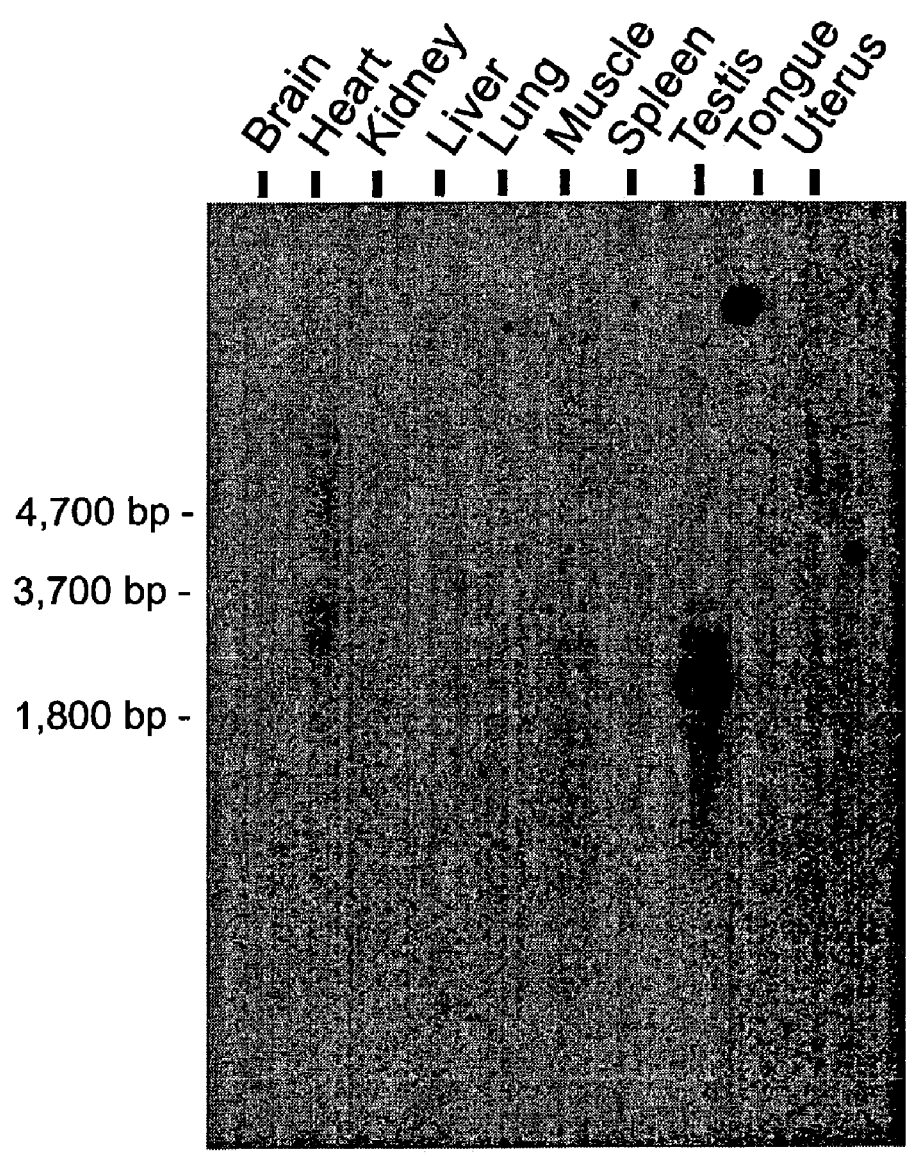

FIG. 20: Northern blot analysis of mouse αT-catenin. RNAs of 10 different mouse tissues were separated by gel electrophoresis, blotted on a membrane and hybridized with a mouse αT-catenin-specific probe, consisting of 296 bp of the 3' end of the mouse αT-catenin cDNA. The sizes of the mRNAs were determined by sequential hybridizations of the Northern blot with a mouse GAPDH probe, with a mouse αE-catenin probe and finally staining of ribosomal RNA with methylene blue.

FIG. 21: Western blot analysis of αT-catenin protein expression in various mouse tissues. (A) Detection of αT-catenin with polyclonal serum #952; (B) Detection of αT-catenin with polyclonal serum #952 after pre-incubation with the specific peptide #893, which blocks detection not only of the 100-kDa band (full-length mouse αT-catenin) but also the 86-kDa band, the 66-kDa band and the 43-kDa band in heart and testis lysates.

Figure 22:
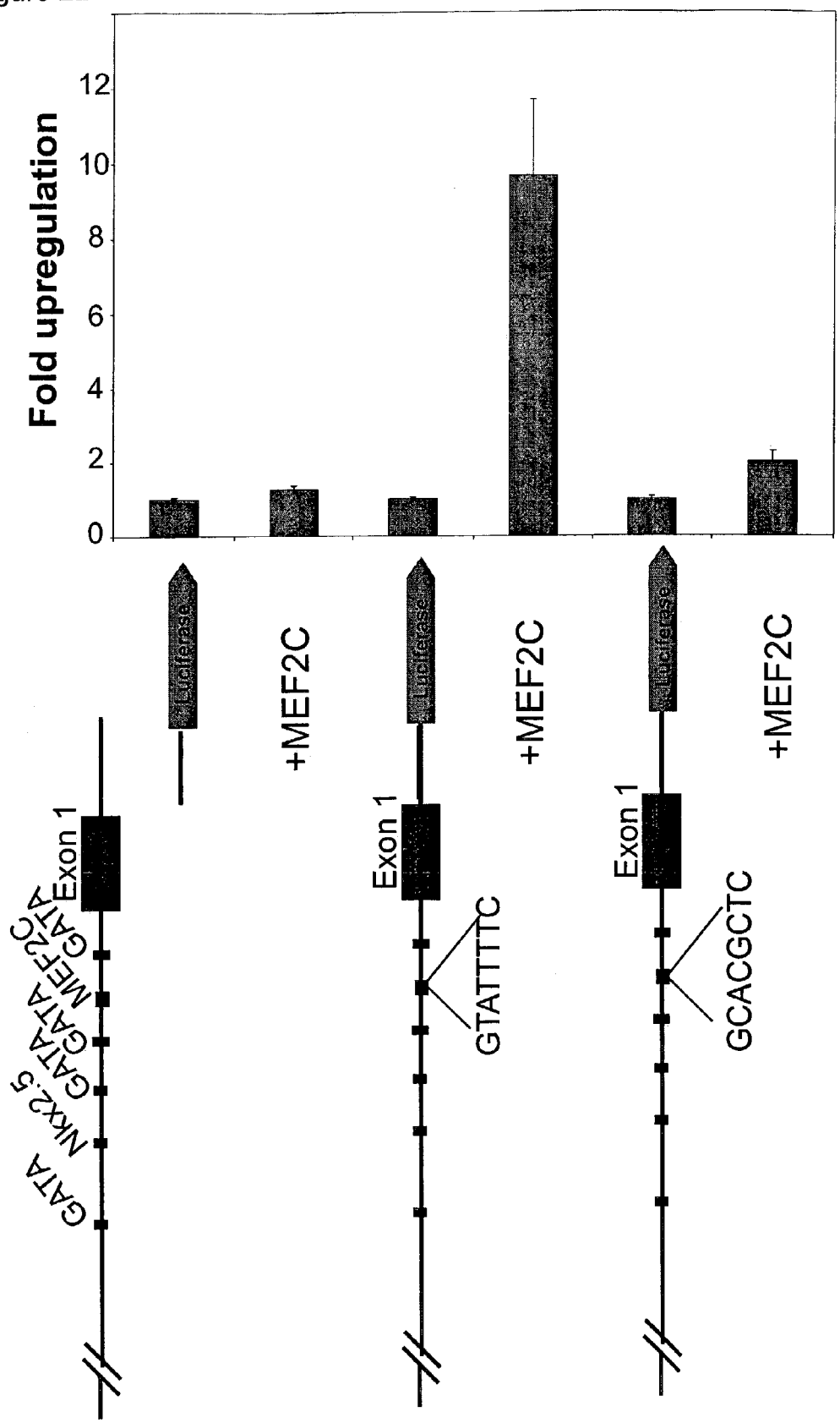

FIG. 22: Influence of MEF2C transcription factor on the αT-catenin promoter activity. AlphaT-catenin promoter luciferase constructs were cotransfected with a MEF2C encoding plasmid in P19 cells (mouse embryonal carcinoma cells). Cells were lysed 48 h after transfection and luciferase activity was measured. A β-galactosidase encoding plasmid was cotransfected to normalize for transfection efficiency. A luciferase construct without αT-catenin promoter serves as negative control and is insensitive to MEF2C. A construct with luciferase under the control of the αT-catenin promoter sequence shows background activity unless cotransfected with MEF2C. This leads to a 10-fold upregulation of the αT-catenin promoter activity. Deletion or mutation of the consensus MEF2C binding site abolishes this effect as illustrated.

DETAILED DESCRIPTION OF THE INVENTION

EXAMPLES

Materials and Methods to the Examples

Cell Cultures

Most of the cell lines used were purchased from the American Cell Type Culture Collection (ATCC, Rockville, Md.). HCT-8/E8, HCT-8/E11R1 and HCT-8/R1 cell lines were obtained by subcloning of the human ileocecal adenocarcinoma cell line HCT-8 (CCL-224), where E stands for epithelioid and R for round-cell variants lacking αE-catenin (VAN Hengel et al., 1997). PC-3 (CRL-1435) is a human prostate carcinoma cell line and HEK-293 (CRL-1573) is a human embryonic kidney fibroblast cell line.

Cloning and cDNA Isolation of Human and Mouse αT-catenin

A human αT-catenin-specific EST clone (IMAGE #728263) was identified by BLAST analysis (Altschul et al., 1990) and requested from the IMAGE consortium UK-HGMP Resource Center (Hinxton, UK). Expression of the corresponding transcript was confirmed by RT-PCR on mRNA from the prostate cancer cell line PC3 with primers MCB967 (5'-TGAGGCAGAAAAAGAAAAGA-3' (SEQ ID NO:87)) and MCB968 (5'-AGTGTGGTTAGGCAGGATT-3' (SEQ ID NO:88)). In order to complete the cDNA sequence we performed two consecutive 5' Marathon™ RACE experiments on a human testis Marathon cDNA library (Clontech, Palo Alto, Calif.). For the first 5' RACE, the gene-specific primer was MCB1027 (5'-AATCTGCCGAGCAAGGACATCCA-3' (SEQ ID NO:90)) and the nested primer was MCB1028 (5'-TCAGGCAGTTGAGTCATCTTAGC-3' (SEQ ID NO:91)). RACE-PCR was performed on a Perkin Elmer 2400 thermal cycler (Perkin Elmer, Foster City, Calif.) following the supplied protocol (touchdown PCR). Obtained RACE fragments were purified from agarose gel on QIAquick™ columns (Qiagen, Chatsworth, Calif.) and cloned in the pGEMT® vector (Promega Corp., Madison, Wis.). The cloned fragment was called pGEMT-ATCTN-RACE1. As the obtained clone appeared to be incomplete, a second 5'-RACE experiment was performed with gene-specific primer MCB1254 (5'-ACCCGTGACGATGTGAGCAACTC-3' (SEQ ID NO:92)) and nested primer MCB1255 (5'-GAGCTGTCTGCGAAGGTCTCTTG-3' (SEQ ID NO:93)). The obtained fragment was cloned in the pGEMT®-easy vector (Promega Corp), and called pGEMTeasy-ATCTN-RACE2.

A mouse αT-catenin-specific expression tag (EST) clone sequence (GenBank Accession No. AW556211) of 624 bp was identified by BLAST analysis (Altschul et al., 1990). In order to complete the mouse cDNA sequence, we performed a 5' RACE reaction (Life Technologies, Paisley, UK) on mouse cDNA. This cDNA was prepared with a gene-specific primer, MCB2461 (5'-CCCCAATGTTTTATGTTAT-3' (SEQ ID NO:114)) from RNA that was isolated with the RNeasy method (Qiagen, Chatsworth, Calif.) from mouse testis and heart tissues. For the 5' RACE reaction, we used primer MCB2481 (5'-CTTGGTGGAGGCAATGTATGAC-3' (SEQ ID NO:118)) and nested primer MCB2482 (5'-TCTGCCGAGCAAGAACATCCAT-3' (SEQ ID NO:119)).

The obtained RACE fragments were purified from agarose gel using the CONCERT™ Rapid Gel Extraction System (Life Technologies) and cloned into the pGEMT®-easy vector (Promega, Madison, Wis.). The resulting plasmid was called pGEMTeasy-maTctn(RACE 1 )cDNA.

As the cloned cDNA was incomplete, we performed a PCR using human primer MCB2335 (5'-CCTCTTGCAA-CATGTGTC-3' (SEQ ID NO:110)) and mouse gene-specific primer MCB2567 (5'-GCGGAGGTCTCTTGTCTTCTT-3' (SEQ ID NO:120)), yielding a product of 684 bp. The obtained fragment was cloned into the pGEMT®-easy vector (Promega), and called pGEMTeasy-maTctn(PCR2567+2335).

As the cloned cDNA was still incomplete we performed another 5' RACE reaction using the GeneRacer™ Kit, version B (Invitrogen, San Diego, Calif.) on RNA isolated from mouse heart tissue. For this 5' RACE reaction, primer MCB2569 (5'-CGCAGTCAGAGAGTTCTTGCTT-3' (SEQ ID NO:121)) was used to prepare gene-specific mouse cDNA. For the touchdown PCR we used primer MCB2711 (5'-CTTCCCGAGCTTCTGGTAGGTTCT-3' (SEQ ID NO:124)). The obtained RACE fragments were purified from agarose gel using the CONCERTT Rapid Gel Extraction system (Life Technologies) and cloned into the pGEMT®-easy vector (Promega). The resulting plasmid was called pGEMTeasy-maTctn(RACE3)cDNA.

On the basis of the consensus mouse αT-catenin sequence, primers MCB2818 (5'-AACGCCTAGAAGC-CATCATC-3' (SEQ ID NO:125)) and MCB2819 (5'-TG-GCAAGAACAATGATGTCA-3' (SEQ ID NO:126)) were designed to amplify the full-length cDNA. The predicted 2979-bp product was obtained by PCR on heart cDNA, using the TaqPlus® Precision PCR System (Stratagene Cloning Systems, La Jolla, Calif.). The PCR-fragment was purified from agarose gel using the CO (Life Technologies) and cloned into the pGEMT®-easy vector (Promega). The resulting plasmid was called pGEMTeasy-maTctn(1-2979). This full-length mouse αT-catenin clone was expressed in an in vitro coupled transcription and translation reaction, using the TNT® Coupled Reticulocyte Lysate System (Promega). The in vitro synthesized proteins were analyzed by Western blotting.

All DNA sequences were obtained by the dideoxy chain termination method (Sanger et al., 1977), using fluorescent dye terminators in a 373ABI automated DNA sequencer (Applied Biosystems, Foster City, Calif.). Sequences were assembled and compared by the DNAstar (DNASTAR Inc, Madison, Wis.), and Staden gap4 software packages (Bonfield et al., 1995). Amino acid similarities alignments were obtained using the CLUSTALW program (Higgins & Sharp, 1989; Thompson et al., 1994) and GCG software. Alignments were shaded using the WWW-BOXSHADE server (http://ulrec3.unil.ch/softward/BOX-form.html).

PAC and BAC Human and Mouse Genomic Library Screening

For the isolation of a human genomic clone of αT-catenin, the PAC genomic library RPCI1 constructed by Ioannou and de Jong (1996), and obtained from HGMP (UK), was screened by PCR with the 3' located primers MCB1260 (5'-GAAAAAGAAAAGATTGCTGAG-3' (SEQ. ID NO:94)) and MCB1261 (5'-CCCTAGTGAAGTCTGT-CATCT-3' (SEQ ID NO:95)), yielding a product of 157 bp. The PCR reaction was optimized on total human genomic DNA and performed with 2.5 mM MgCl$_2$ at an annealing temperature of 56° C. Clone 320B7 (#1487) was found to be specific by DNA sequencing using primers MCB1260 and MCB1261. However, this PAC clone was found to contain only the last exon of the CTNNA3 gene (exon 18 in FIGS. 4 and 5).

A BAC (Bacterial Artificial Chromosome) human genomic library (Genome Systems, St. Louis, Mo.) was screened with primers located in the first protein encoding exon, i.e., primers MCB2099 (5'-TGTCATCTGCCTCT-CAATTTG-3' (SEQ ID NO:104)) and MCB2100 (5'-AT-GCTGCCTTTCTGTTTCTTC-3' (SEQ ID NO:105)), yielding a product of 149 bp at an annealing temperature of 52° C. and 2 mM MgCl$_2$. Clone 162A20 was found to comprise this exon, as confirmed by direct sequencing and fragment subcloning. To clone the αT-catenin promoter region, the BAC162A20 clone was digested with the 6-bp cutters BamHI, BglII, EcoRI, HindIII, MluI, SstI, SalI, XbaI and XhoI. Fragments containing exon 1 of the αT-catenin gene were identified by Southern blot hybridization with a primer located in this first exon, i.e. MCB2099. An 8-kb BamHI fragment was cloned in the pGEM11 vector and positive clones were identified by colony hybridization with primer MCB2099. The promoter region in this clone was sequenced by primer walking using primers MCB2217 (5'-CAGAT-GACAGTGGGGCAGTC-3' (SEQ ID NO:106)), MCB2287 (5'-AACTTGTTACTGAAAATACT-3' (SEQ ID NO:109)), and MCB2350 (5'-CATTACCATTTTTCCGACTT-3' (SEQ ID NO:111)).

A BAC mouse genomic library (Genome Systems) was screened by PCR with primers located in either exon 1 (primers MCB2820 and MCB2837), in exon 2 (primers MCB2840 and MCB2841) and in exon 3 of the mouse αT-catenin gene (primers MCB2838 and MCB2839). Sequences of these primers are:

```
MCB2820:
5'-CCCCTTTCTCTCTTATCCTGAG-3'     (SEQ ID NO:127)

MCB2837:
5'-CTTTCTGATGCTTCCTACAAGTAAA-3'  (SEQ ID NO:128)

MCB2840:
5'-GTCGGCAGAAACGCCAATA-3'        (SEQ ID NO:131)

MCB2841:
5'-GAGGCTCCAGCAGTTTCTCC-3'       (SEQ ID NO:132)

MCB2838:
5'-CCGCAGAATCCTTCCAACA-3'        (SEQ ID NO:129)

MCB2839:
5'-GCTGCCAGCTCTTCCTTTAAA-3'.     (SEQ ID NO:130)
```

Clone 164N16 was found to comprise these first three exons, as confirmed by Southern blot analysis.

Fluorescence In Situ Hybridization (FISH)

PAC clone 320B7 (#1487) was used for fluorescence in situ hybridization (Kievits et al., 1990). PAC DNA was prepared with Kb-Magnum purification columns (Genome Systems, St. Louis, Mo.) and nick-translated using a BioNick kit (Gibco-BRL). Denaturation of labeled probe and human chromosomes, hybridization and fluorescent detection were performed as described previously (van Hengel et al., 1995). The chromosomes were stained with DAPI to reproduce G-banding. The slides were observed using a Zeiss Axiophot fluorescent microscope (Zeiss, Jena, Germany) and images captured with a Photometrics Image Point CCD camera (Photometrics, Munich, Germany). Results were analyzed with the MacProbe software of PSI (Perceptive Scientific International, League City, Tex.). At least 20 metaphase spreads of normal human lymphocytes were analyzed.

Confirmation of Human Chromosomal Localization by PCR-based Hybrid Mapping

Genomic PCR was performed with primers

MCB2056
(5'-GAAATGCCATGGAGCTCTAAC-3' (SEQ ID NO:102)) and

MCB2057
(5'-ATGGGAAGGCAAACCAGTCAC-3' (SEQ ID NO:103)).

These primers correspond to intronic sequences and are flanking an exon, as deduced from the sequence of a genomic clone (GenBank No AQ163827) (Table 1; FIG. 5). A product of 274 bp was expected. As a positive control, genomic DNA from human placenta was used to optimize the annealing temperature of 52° C. and a concentration of 2 mM $MgCl_2$. The PCR was performed on samples of the Genebridge 4 radiation hybrid mapping panel (HGMP-RC, UK), which allows construction of high-resolution contiguous maps of human chromosomes. Analysis was performed on the Web page http://www.hgmp.mrc.ac.uk/cgi-bin/contig/rhmapper.pl.

PCR with the same primer set was also performed on a monochromosomal hybrid mapping panel (NIGMS Human/Rodent Somatic Cell Hybrid Mapping Panel #2, Coriell Cell Repositories, Camden, N.J.). All cell hybrid templates were diluted to a final DNA concentration of 100 ng/μl, using 1 μl as PCR templates.

Cloning of Two Hybrid Prey and Bait Plasmids

After completion of plasmid constructs, as described below, all clones were checked by DNA sequencing. For all PCRs, Pfu polymerase (Stratagene, La Jolla, Calif.) with proofreading activity was used.

αT-catenin

For cloning of the full-length hαT-catenin cDNA in the pGBT9 vector (Clontech), in fusion with the GAL4 binding domain, four consecutive constructs were made. A PCR product of 1,134 bp was synthesized with primers MCB1607 (5'-AGAATTCTCAGCTGAAACACCAAT-CAC-3' (SEQ ID NO:96)) and MCB1609 (5'-AGGATCCT-GCGAAGGTCTCTTGTCT-3' (SEQ ID NO:98)) using the pGEMTeasy-ATCTN-RACE2 clone as a template. This product was restricted with EcoRI plus BamHI and ligated to the EcoRI and BamHI sites of the pGBT9 vector, thus yielding pGBT9-ATCTN(179-949). This construct was opened with PstI, and the PstI insert of 1,111 bp from clone pGEMT-ATCTN-RACE2 was ligated to obtain pGBT9-ATCTN(179-1306). From this construct, the EcoRI-SspI insert of 1,082 bp was isolated and ligated together with fragment SspI-SalI from pGEMTeasy-ATCTN-RACE1 in the pGBT9 vector, restricted with EcoRI-SalI. In this way pGBT9-ATCTN(179-2176) was obtained. In order to have an overlapping 3' clone, a PCR product of 890 bp was synthesized with primers MCB1610 (5'-GGATGATAAT-CAATTTGTGGACATCTC-3' (SEQ ID NO:99)) and MCB 1608 (5'-GGGATCCGTAGATTTGTCTTCCTCTAA-3' (SEQ ID NO:97)). For this PCR, template cDNA was synthesized from RNA prepared with the RNeasy kit (Qiagen) from the PC-3 prostate cancer cell line (American Type Culture Collection, Rockville, Md., U.S.A.). The PCR product was cut with BglII and SalI, and inserted in the BglII-SalI opened construct pGBT9-ATCTN(179-2176) to finally achieve the construct pGBT9-ATCTN(179-2860).

From pGBT9-ATCTN(179-2860), the EcoRI-SacI insert was ligated together with the SacI-NotI fragment from the original EST clone pT3T7-EST728263, in the EcoRI-NotI digested pGBKT7 vector (Clontech). The obtained construct was designated pGBKT7-ATCTN(179-3024). Further, the EcoRI-SalI insert from pGBT9-ATCTN(179-2860) was cloned into the EcoRI-SalI sites of the LexA bait vector pLexMG (pGBT9 in which the GAL4 binding domain has been exchanged with the LexA binding domain by Mathias Gautel, EMBL, Heidelberg). In this way, pLexMG-ATCTN (179-2860) was obtained.

α-catulin

The full-length α-catulin cDNA sequence (GenBank Accession number U97067) was isolated by us in 3 steps (Janssens et al., 1999): The full-length sequence was compiled from 2 EST sequences (clones 36498 and 67201) and one 5'-RACE clone. In order to obtain a clone with the full-length sequence, these 3 clones were assembled in the pGEM11 vector (Clontech). First, the insert of EST clone 67201 was isolated by a SmaI-MunI digest and ligated to the SmaI-MunI opened vector pGEMT-αctlRACE. In that way the construct pGEMT-αctl(1-1369) was obtained. Part of the EST #36498 sequence (1,003 bp) was obtained by a BglII restriction digest, yielding a fragment comprising the complete 3' part of the open reading frame (ORF) but only part of the 3' untranslated region. This fragment was inserted in the plasmid pGEMT-αctl(1-1369) opened with BglII. This resulted in a clone containing the complete open reading frame of α-catulin, i.e. pGEMT-αctl(1-2264).

This clone was used as a template to generate a PCR product with primer MCB725 (5'-TATTAGATATCGC-CTCTCCCGGACCCGCC-3' (SEQ ID NO:86) comprising an EcoRV site) and primer MCB711 (5'-AGGGGGCAGTG-GCTGAAGAAAGAAGTAATC-3'(SEQ ID NO:85)). In a 3-point ligation this PCR product, cut with EcoRV +MunI, was ligated together with a MunI-SalI fragment of pGEMT-αctl(1-2264) into the BamHI(blunted)-SalI restricted pGBT9 two-hybrid vector (Clontech), in frame with the ORF encoding the GAL4 DNA binding domain. The obtained constructed was called pGBT9-αctl(50-2264).

αE-catenin

Screening of a human fetal kidney 5' Stretch cDNA library in vector λDR2 (Clontech, Calif.) resulted in isolation of the pDR2αECTN plasmid, containing full-length αE-catenin cDNA. From this plasmid, Eco47III-SphI and SphI-SalI fragments were ligated in the SmaI-SalI digested pGBT9 vector, yielding pGBT9-αECTN, in which the full-length αE-catenin ORF is fused in frame with the OF encoding the GAL4 DNA binding domain.

From pGBT9-αECTN, the EcoRI-SalI fragment was cloned into the pLexMG vector restricted with EcoRI and SalI. In this way pLexMG-αECTN was obtained in which the full-length αE-catenin ORF is fused in frame with the ORF encoding the LexA DNA binding domain.

αN-catenin

The cDNA for human αN-catenin was kindly provided as plasmid pPN-hANCTN by Dr. C. Petit (Claverie et al., 1993). Nearly full-length αN-catenin was amplified from pPN-hANCTN with primers MCB137 (5'-AC-CCCCCGGGGGCAACTTCACCTATCATTC-3' (SEQ ID NO:83)) containing an XmaI site), and MCB138 (5'-GC-CGCCGCCTTCCTTTTCATTTCCGCTCTT-3'(SEQ ID NO:84)). The PCR fragment was digested with XmaI and BanI and ligated together with a BanI-HindIII fragment of pPN-hANCTN in the XmaI-HindIII digested pAS2 vector (Clontech). Thus the pAS2-αNCTN plasmid was obtained, in which codons 4 to 906 of αN-catenin are fused in frame with the ORF encoding the GAL4 DNA binding domain. From this construct, the XmaI-HindIII insert was transferred to the XmaI-HindIII opened pGBT9 vector, yielding pGBT9-αNCTN.

β-catenin

The full-length β-catenin cDNA was kindly provided as plasmid pBAT-βCAT (from Dr. J. Behrens, Berlin, Germany). The amino terminal fragment 239-717 was obtained as an NcoI-PstI restriction fragment, of which the NcoI cut end was filled in with Pfu polymerase. This fragment was cloned into the SmaI-PstI opened pGAD424 vector, by which the construct pGAD424-ATβctn was obtained.

Plakoglobin

Plasmid pHPGCa2.1 with the full-length human plakoglobin cDNA was kindly provided by Dr. W. Franke. PCR was performed on this plasmid, with primer MCB133 (5'-GGTGAATTCGTCAGCAGCAAGGGCATCAT-3'(SEQ ID NO:81)), containing an EcoRI site) and primer MCB134 (5'-GGTTTGATGCAGGGTCCACAGGCAGTTCT-3' (SEQ ID NO:82)). The obtained PCR product (encoding plakoglobin residues 227-1228) was digested with EcoRI and SacI (residues 227-559) and ligated together with the fragments SacI-BglII (residues 560-1856) and BglII-PstI (residues 1857-2340) from pHPGCa2.1, into the EcoRI-PstI opened pGAD424 vector (Clontech). Thus, the plasmid pGAD424-Plakoglobin(227-2340) was obtained.

Yeast Two-hybrid Transformation

The yeast strain Y190 (Matchmaker, Clontech, CA), which contains GAL4 promoter driven His and β-galactosidase reporters, was used for cotransformation of pGBT9 bait and pGAD424 prey plasmids, comprising the cloned inserts of interest. The yeast strain L40, which contains LexA promoter driven His and β-galactosidase reporters, was used for cotransformation of pLexMG bait with pGAD424 prey plasmids, comprising the cloned inserts of interest.

The yeast cells were grown in YPD medium until a log-phase culture with an $O.D._{600}$ of about 0.8 was obtained, and transformed by the lithium acetate procedure (Gietz et al., 1992). Cotransformants were selected by plating the transformation mix on SD minimal medium plates lacking leucine and tryptophan. After three days, colonies were picked and grown overnight in SD without leucine and tryptophan, but containing 0.07 M potassium phosphate. Replica plates selecting for interaction were made on SD lacking leucine, tryptophan and histidine, but containing 0.07 M potassium phosphate, 40 mM 3-amino-triazol to suppress leaky His expression, and 80 mg/ml X-β-GAL (Duchefa, Haarlem, The Netherlands).

CPRG Yeast Two-hybrid Quantification of β-galactosidase

To assay the strength of interaction between α-catenins and β-catenin, β-galactosidase activity was assayed using chlorophenol red-β-D-galactopyranoside (CPRG, Boehringer Mannheim, Del.) as a substrate, according to the provided protocol (Clontech Yeast Protocols Handbook). Briefly, transformed yeasts are grown until $OD_{600}$ of about 0.6, concentrated in three different dilutions (1.25, 2.5 and 5 times concentrated, respectively) and allowed to develop red color after addition of CPRG substrate (measured at that time point, at $OD_{578}$). One β-galactosidase unit is defined as the amount which hydrolyzes 1 μmol of CPRG to chlorophenol red and D-galactose per minute per cell (Miller et al., 1972). The amount of units is calculated as 10,000× $OD_{578}$/(time×concentration factor×$OD_{600}$).

Cloning of Expression Plasmids

The full-length human αT-catenin cDNA was excised from the construct pGBT9-ATCTN(179-2860) with restriction enzymes EcoRI-SalI and inserted in the EcoRI-SalI digested pEGFPC2 vector (Clontech), in order to obtain an in-frame amino-terminal fusion with the GFP protein. The resulting plasmid was called pEGFPC2-ATCTN(179-2860). The EcoRI-NotI insert from pGBT9-ATCTN(179-2860) was ligated into the EcoRI-NotI digested vector pEF6MycHisA (Invitrogen), providing a C-terminal fusion between αT-catenin and the Myc and His epitopes in the construct pEF6MH-ATCTN(179-2860). In this construct, no in-frame start codon is present at the very 5' side, but there is a start codon present at position 596. The full-length fusion construct, named pEF6MH-ATCTN(1-2860), was obtained by introducing the 5' part of the αT-catenin cDNA from clone pGEMT-RACE2, cut with EcoRI-BstEII, into the EcoRI-BstEII opened vector pEF6MH-ATCTN(179-2860).

Transfection Methods

For vaccinia virus-mediated transient overexpression, α-catenins were cloned in the pE/L-GFP vector (Frischknecht et al., 1999). Cells were transfected with Lipofectin (Life Technologies) and simultaneously co-infected with vaccinia virus strain ΔA36R, which does not make actin tails (Parkinson and Smith, 1994). At 4 to 30 h after transfection, high levels of expression under control of the vaccinia virus early/late promoter (E/L) (Chakrabarti et al., 1997) were obtained of the cloned cDNA, amino-terminally fused to GFP. Human αT-catenin was amplified with Taq+Precision polymerase (Stratagene) using primers containing a 5' NotI site and a 3' EcoRI site (MCB2386, 5'-GGGGGCGGC-CGCGGAGGGTCAGCTGAAACACCAATCACATTG-3'

(SEQ ID NO:112) and MCB2387, 5'-CCCCGAATTCGC-CGTGTGGTTAGGCAGGATTTTGTCATATAG-3' (SEQ ID NO:113)) and cloned into the NotI-EcoRI sites of the pE/L-GFP vector.

For stable transfection of HCT-8/R1 carcinoma cells, $4\times10^6$ cells were electroporated (Easyject; Eurogentec, Seraing, Belgium) with 10 μg of plasmid pEF6MH-ATCTN(179-2860). Cells were plated and cultured in the presence of 6 μg/ml blasticidin (Invitrogen) to select for stable transfectants. Colonies of blasticidin-resistant cells were isolated and tested by immunofluorescence and Western blotting for expression of αT-catenin. One stable clone was isolated and called HCT-8/R1/T31. As a negative control we transfected HCT-8/R1 cells with the empty pEF6MH vector, resulting in stable clones called HCT-8/R1/1743. A clone of HCT-8/E11R1 cells, stably transfected with αN-catenin cDNA and designated HRpCαN2 (van Hengel et al., 1997), was used in comparison. Likewise, HCT-8/E11R1 carcinoma cells were transfected with plasmid pEGFPC2-ATCTN(179-2860). After selection with G418 (800 μg/ml), one stable αT-catenin expressing clone was isolated and called HCT-8/E11R1/T14.

Expression Analysis by RT-PCR

Expression analysis using the human Rapid-Scan panel (OriGene Technologies Inc, Rockville, Md.) was performed on 100-times diluted template, followed by a nested PCR (1/10 of the end volume of the first reaction was used). The end-point determination method used does not allow a reliable determination of expression levels to be deduced from the amount of PCR product visualized on gel. Therefore, visual presence of a signal (even weak) was scored as positive, and complete absence was scored as negative. Primers MCB967 (5'-TGAGGCAGAAAAAGAAAAGA-3' (SEQ ID NO:87)) and MCB968 (5'-AGTGTGGTTAG-GCAGGATT-3'(SEQ ID NO:88)) were used for the first PCR, yielding a product of 743 bp. For nested PCR, primers MCB967 (5'-TGAGGCAGAAAAAGAAAAGA-3'(SEQ ID NO:87)) and MCB1010 (5'-GCTGAGCCTCGTCT-GAC-3'(SEQ ID NO:89)) were combined, yielding a smaller product of 630 bp. Amplified products were checked for specificity by sequence analysis, showing that the double bands observed after nested RT-PCR of heart and testis samples in particular are indeed the larger primary product and the smaller nested product.

As a control, an αE-catenin-specific product of 747 bp was amplified with primers MCB53 (5'-CTTCGGGC-CTCTGGAATTTA-3'(SEQ ID NO:79)) and MCB73 (5'-CGACATCAGGGTGCTGTAGG-3'(SEQ ID NO:80)).

For RT-PCR analysis of mouse tissues, RNA was prepared from different tissues with the RNAeasy method (Qiagen) and cDNA was prepared using a commercial kit (Life Technologies, Ghent, Belgium). For mouse αT-catenin, primers MCB2461 (5'-CCCCAATGTTTTATGTTAT-3' (SEQ ID NO:114)) and MCB2463 (5'-GGGGAGAACT-CATCGTAT-3' (SEQ ID NO:115)) were designed on the sequence of an EST clone (GenBank Accession No. AW556211), resulting in amplification of a 442-bp product. For mouse αE-catenin (GenBank Accession No. NM_009818), a 733-bp product was amplified with primers MCB2636 (5'-GAAGGCCCCTGAGAAGAA-3' (SEQ ID NO:122)) and MCB2637 (5'-CCCGAATAAAGCAACTC-CAT-3' (SEQ ID NO:123)). For mouse αN-catenin (GenBank Accession No. NM_009819), a 858-bp product was amplified with primers MCB2479 (5'-GCCCTGAT-TGAGTTTGATAA-3' (SEQ ID NO:116)) and MCB2480 (5'-CCCAGCTTCATAGTTCTCC-3' (SEQ ID NO:117)). As a control, a 452-bp fragment of mouse GAPDH was amplified with primers MCB2219 (5'-ACCACAGTCCAT-GCCATCAC-3' (SEQ ID NO:107)) and MCB2220 (5'-TCCACCACCCTGTTGCTG TA-3' (SEQ ID NO:108)).

Expression Analysis by Northern Blotting

RNA was prepared from different mouse tissues, using the RNeasy method (Qiagen). For each tissue sample, 25 μg RNA was separated on a 1% agarose gel. RNA was transferred by Northern blotting on a Hybond™-N$^+$ membrane (Amersham Pharmacia Biotech, Rainham, UK).

A mouse αT-catenin-specific probe of 296 bp was generated by PCR with primer MCB2043 (5'-TCGAGGAT-GAAGGCTCTG-3' (SEQ ID NO:100)) and primer MCB2044 (5'-TGTTTAACCCCAATGTTT-3' (SEQ ID NO:101)). The PCR product was labeled with α[$^{32}$P]-dCTP using the Radprime DNA labeling System (Life Technologies). After hybridization according to standard procedures, the blot was washed at high stringency. For detection, a Phosphor Imager cassette (Molecular Dynamics, Sunnyvale, Calif.) was exposed for 4 days and scanned with a Molecular Imager® FX using the Quantity One software (BioRad, Richmond, Calif.).

Antibodies

Peptides corresponding to, respectively, the amino-terminus (MSAETPITLNIDPQDLQ-C (SEQ ID NO:133)) and the carboxy-terminus (C-KIHPLQVMSEFRGRQIY (SEQ ID NO:134)) of the human αT-ctn protein were synthesized and coupled to keyhole-limpet hemocyanin via the additional cysteine residue at either the carboxyterminal or the amino terminal end of the peptides. 200 μg of peptide was injected in each of three rabbits using Titermax (Sigma, St Louis, Mo.) as adjuvant. Boosts were given with intervals of minimum two weeks. Sera were tested by ELISA on the peptide used for injection, using the non-relevant peptide as a negative control. The sera #952 (specific for the carboxyterminal peptide) and #954 (specific for the amino-terminal peptide) were affinity purified on hydroxymercuribenzoate-agarose (Sigma, St Louis, Mo.), coupled to the respective immunizing peptides. Crude and purified sera were tested on lysates of HEK cells transfected with plasmids pEGFPC2-ATCTN(179-2860) and pEF6MH-ATCTN(1-2860), encoding respectively full-length Myc-tagged and GFP-tagged αT-catenin. For Western blotting, a dilution of 1:1,000 was used for the crude polyclonal sera and a dilution of 1:250 for the affinity purified sera. Recognition of αT-catenin was inhibited by incubation of the polyclonal antibody with the antigenic peptide for one hour prior to use. Serum #952, but not serum #954, turned out to cross-react with mouse αT-catenin.

Monoclonal antibodies were generated by injection of the N-terminal peptide (MSAETPITLNIDPQDLQ-C (SEQ ID NO:133)) or the C-terminal peptide (C-KIHPLQVMSEFR-GRQIY (SEQ ID NO:134)) in C57Bl/6 mice. Boosts were given with intervals of 2 weeks, and sera were tested by ELISA until a titer of 1:10,000 without loss of reactivity was obtained after 6 weeks. Hybridomas were generated by fusion of spleen cells with Sp20_Ag14 myeloma cells. Supernatants of hybridoma cell lines were tested by ELISA.

For the N-terminal peptide, up to 72 strongly reacting clones were tested on Western blots for recognition of αT-catenin, fused at its amino terminus to GFP. From the 17 positive hybridomas identified in this way, 4 were also able to recognize native αT-catenin protein in MCF-7 cells transfected with plasmid pEGFPC2-ATCTN(179-2860). A subclone of hybridoma 892_24D2, 892_24D2S (deposited at BCCM under the number LMBP 5537CB), was used for further analysis.

For the C-terminal peptide, 30 out of 96 ELISA-positive clones recognized GFP-αT-catenin by Western Blotting, from which 3 were able to recognize native αT-catenin protein by immunofluorescence. A subclone, called hybridoma 893_32C6S, was deposited at BCCM under the number LMBP 5728CB.

Neither monoclonal antibody was found to cross-react with mouse αT-catenin.

SDS-PAGE and Western Blot Analysis

Protein lysates from various mouse tissues were prepared by isolating the tissues from normal BALB/c mice and mixing them in Laemmli buffer (Laemmli, 1970). Debris was removed by centrifugation and protein concentration was measured by the BioRad DC kit (BioRad, Richmond, Calif.). Lysates from subconfluent cultures of cell lines were also prepared in Laemmli buffer, followed by sonication and centrifugation. Of each protein lysate, 40 μg was diluted with 6× sample buffer (0.35 M Tris-HCl, pH 6.8, 10.28% SDS, 36% glycerol, 5% β-mercaptoethanol, 0.012% bromophenol blue), boiled for 5 min and subjected to separation on 10% polyacrylamide gels. Proteins were transferred onto Immobilon-P membranes (Millipore, Bredford, Mass.) and blocked with 5% nonfat dry milk, 0.1% Tween-20 in Tris-buffered saline buffer (100 mM Tris-HCl, pH 7.4, 1.4 M NaCl) prior to incubation with the primary antibody. Detection was carried out by phosphatase-coupled secondary antibodies (Sigma) and nitroblue tetrazolium/5-bromo-4-chloro-3-indolyl phosphate (NBT/BCIP) as a substrate.

Co-immunoprecipitation was performed on lysates of transfected HEK cells, prepared in PBS containing 1% NP-40 and a protease inhibitor cocktail (Boehringer). Lysate (800 μg) was incubated overnight with 4 μg of the respective antibody, after which 100 μl of 50% protein-G (Amersham Pharmacia Biotech, Rainham, UK) was added to monoclonal antibodies, whereas protein-A Sepharose (Amersham Pharmacia Biotech) was added to polyclonal antibodies. After 2 h of incubation, the Sepharose beads were washed three times with PBS containing 0.1% NP-40, followed by boiling for 5 min in Laemmli buffer, before being subjected to SDS-PAGE and Western blotting. On these Western blots, protein was detected by the ECL detection system using secondary antibodies coupled to horseradish peroxidase (Amersham Pharmacia Biotech).

Tissue Staining

Frozen sections of human heart and testis tissue were treated for 20 min with 0.3% $H_2O_2$ diluted in methanol, then washed in water and PBS, and pretreated for 10 min with goat serum diluted 1:10. The sections were then incubated for 30 min with crude monoclonal 892_24D2S hybridoma supernatans, which was diluted 1:5 in PBS containing 1% bovine serum albumin. The secondary antibody used was biotin-labeled goat-anti-mouse Ig (DAKO, Denmark), which was subsequently linked to the streptavidin-ABC complex coupled to horseradish peroxidase. Detection was carried out by a 5 min incubation with the chromogenic peroxidase substrate diaminobenzidine (Sigma). Cell nuclei were counterstained for 5 min with haematoxylin (Sigma), after which the slides were dehydrated by washing in 70%, 90% and two times 100% ethanol. Finally the slides were cleared in toluol and mounted.

For double immunofluorescent staining, frozen sections were air dried, fixed in acetone at 4° C. for 10 min, washed in PBS and preincubated with 10% goat serum for 10 min. The slides were then incubated for 45 min with mixtures of primary antibodies diluted in PBS: either 1:5 monoclonal antibody 892_24D2S plus 1:500 polyclonal anti-αE-catenin, or 1:500 polyclonal antibody #952 plus 1:500 monoclonal anti-N-cadherin. The secondary goat anti-mouse IgG and goat anti-rabbit IgG antibodies used were labeled with FITC or TRITC (Santa Cruz, Santa Cruz, Calif.), or with Alexa 488 or Alexa 594 (Molecular Probes, Eugene, Oreg.).

Immunocytochemistry of Cell Cultures

Cells were grown on glass coverslips until confluency, rinsed briefly with PBS and fixed with either ice-cold methanol for 1 min, or with 3% paraformaldehyde (Merck, Darmstadt, Germany) for 10 min at room temperature, followed by permeabilization in 0.2% Triton X-100 (Sigma) for 2 min. Cells were then incubated for 30 min with primary antibody diluted in blocking solution (20 mM Tris/HCl pH 7.5, 154 mM NaCl, 2 mM EDTA, 2 mM $MgCl_2$, with 1% BSA and 1% goat serum), washed in PBS, and incubated for 30 min with secondary antibodies diluted in blocking solution. Secondary anti-mouse IgG or anti-rabbit IgG antibodies were coupled to either Alexa 594 or Alexa 488 (Molecular Probes) and used at dilution 1:300. Finally, cells were treated for 10 sec with a 4'-6-diamidine-2-phenylindole-dihydrochloride so DNA, followed by mounting in Vectashield (Vector Laboratories, Burlingame, Calif.) to prevent photobleaching. Samples were examined with a Zeiss Axiophot microscope and images were recorded with a high-performance charge-coupled digital camera (Cohu, San Diego, Calif.) and NIH image software (version 1.62), or with a MicroMAX camera (Princeton, Trenton, N.J.) and MetaMorph software (Image Universal Corporation, New York, N.Y.).

Fast Aggregation Assay

Cell-cell adhesion was numerically evaluated in an aggregation assay as described before (Bracke et al., 1993). In brief, cultures were dissociated into single-cell suspensions under E-cadherin-saving conditions using collagenase. They were incubated under Gyrotory shaking (New Brunswick Scientific, New Brunswick, N.J.) at 80 rpm for 30 min in an isotonic buffer containing either 1 mM EGTA or 1.25 mM $Ca^{2+}$. E-cadherin could be functionally blocked by treatment with MB2 anti-cadherin monoclonal antibody, starting 30 min before aggregation at 4° C. and continued throughout aggregation at 37° C. The volume % distribution in function of the particle diameter was measured by an LS200 particle size analyzer (Coulter Electronics Ltd., Luton, UK), at the start of the incubation at 37° C. (t0) and after 30 min (t30).

Slow Aggregation Assay

Slow aggregation was performed as described (Boterberg et al., 2000). Briefly, single-cell suspensions were seeded onto a semi-solid agar medium. After 24 h, aggregate formation was evaluated subjectively by phase contrast microscopy at 40 times magnification.

Example 1

Isolation of Novel α-catenin cDNAs

By performing BLAST analyses (Altschul et al., 1990) with αE-catenin sequences as a query, human EST sequences with GenBank Accession Nos. AA393647 and AA400832 (both originating from IMAGE clone-#728263) were found to be, similar but not identical to αE- or αN-catenin. By RT-PCR, we confirmed faint expression of this novel transcript in the PC3 prostate carcinoma cell line. Two consecutive 5' RACE experiments provided us with a full-length cDNA sequence (FIG. 1A), which was deposited with GenBank under the Accession No AF091606. The 3024-bp sequence (SEQ ID NO:1) contains a Kozak-consensus start codon (Kozak, 1991) at position 176, preceded by a stop codon at position 137. A stop codon terminating the long open reading frame (ORF) is located at position 2861, and a putative poly-adenylation signal is seen at the 3' untranslated region at 38 bp before the end of the sequence. The ORF encodes a protein of 895 amino acid residues (SEQ ID NO:2), with a predicted molecular weight of 100 kDa and an overall identity to αE-catenin (102 kDa) and αN-catenin (104 kD) of respectively 58 and 56% (FIG. 1B). The overall homology is higher, as similarities were calculated of 74 and 70% with respectively αE- and αN-catenin. This novel protein is therefore to be considered a true α-catenin family member, and was called αT-catenin because its transcript was discovered in testis-derived mRNA. When the three main homology domains, as proposed by Herrenknecht (Herrenknecht et al., 1991), are aligned separately, we noticed that sequence conservation is elevated up to 71.5% identity in the carboxy-terminal domains. In the alignment of the three full-length α-catenin proteins, high sequence conservation in previously described functional domains was observed, but also in other regions (FIG. 2).

5' RACE and RT-PCR experiments provided us with a full-length mouse αT-catenin cDNA sequence of 2979 bp (FIG. 16; SEQ ID NO:4), which we cloned in the pGEMT®-easy vector. The obtained sequence is deposited with GenBank under the Accession No AF344871. This 2979-bp sequence contains a start codon at position 160, preceded by a stop codon at position 114. The stop codon terminating the ORF is located at position 2846. The ORF encodes a protein of 895 amino acid residues (SEQ ID NO:5), with a predicted molecular weight of 100 kDa. Indeed, after in vitro transcription/translation of plasmid pGEMTeasy-maTctn(1-2979), encoding the full-length mouse αT-catenin cDNA, a protein of approximately 100 kDa was detected (FIG. 17A).

The overall identity of the mouse αT-catenin to the human αT-catenin protein (FIGS. 16B and 18) is about 95%, whereas the overall identity to mouse αE- and αN-catenin is about 66% and 67%. Hence, we can conclude that the cloned sequence is the mouse orthologue of human αT-catenin.

Example 2

Analysis of Human and Mouse αT-catenin Genes

By PCR screening, we isolated a human genomic PAC clone, called clone 320B7 (#1487). This clone was used to perform fluorescence in situ hybridization (FISH), which revealed the localization of the αT-catenin gene CTNNA3 on chromosome band 10q21 (FIGS. 3A and 3B). This localization was confirmed by monochromosomal hybrid mapping and by Genebridge4™ PCR screening. The obtained pattern of PCR products indeed pointed to localization on 10q21, close to marker D10S1461 (FIG. 3C). The region 10q21-23 has been identified as a candidate region for autosomal dominant dilated cardiomyopathy (Bowles et al., 1996). However, up to now, there was no indication of a candidate gene in that region. Partial sequencing of PAC clone #1487 revealed that the clone contains only the last exon of CTNNA3 (exon 18 in FIGS. 4 and 5) besides intronic sequences preceding this exon. Upon database mining by BLAST algorithms, it was found that several genomic sequences (listed in Table 1 and 2) comprise boundaries of different exons of the CTNNA3 gene (FIGS. 4 and 5).

In order to obtain a human genomic clone containing the 5' end of CTNNA3, a human BAC library was screened by PCR with 5' located primers. Clone 162A20 indeed contains the upstream genomic region but comprises only exons 1 and 2 with flanking intronic sequences, besides the upstream gene-regulatory 5' sequences of the CTNNA3 gene. Indeed, from this genomic BAC clone about 1.2 kb of αT-catenin promoter region was sequenced (FIG. 6A and SEQ ID NO:3). This promoter sequence was found to bear several putative binding sites for muscle specific transcription factors as predicted by the "Matinspector-Transcription-Factor-binding-site search program" (Quandt et al., 1995). The functional relevance of such sites is suggested by the conservation across species (FIG. 6B) and indeed demonstrated for the MEF2C binding site (FIG. 22).

All genomic data were deposited with GenBank under accession numbers AF282678 to AF282692 and AF391792 to AF391794. Primers were designed on intronic sequences flanking each exon in order to amplify each of the 18 CTNNA3 exons for applications such as analysis of mutations and polymorphisms by SSCP or denaturing HPLC (Table 3). At the amino acid level, most exon-exon boundaries (boxed in FIG. 4) coincide with the boundaries determined for the αE-catenin CTNNA1 gene (Furukawa et al., 1994) and the CTNNAL1 gene (Janssens et al., 1999), pointing towards a common ancestor for all α-catenin genes. Interestingly, divergence in the genomic structure is observed for the CTNNA3 region covering exons 13 to 15. This domain corresponds to a region where the a-catulin gene CTNNAL1 also shows a divergent genomic organization, besides a "gap" in the open reading frame.

In order to obtain a mouse genomic clone containing the 5' end of the Ctnna3 gene, a mouse BAC library was screened by PCR with primers located in the first three exons of the mouse Ctnna3 gene. Genomic clone 164N 16 was found to contain these three exons. Part of the mouse promoter sequence was determined (SEQ ID NO:6).

Example 3

αT-catenin Interacts Stronger with β-catenin than Other α-catenins Do

The colocalization of αT-catenin and β-catenin suggested interaction between these two proteins. We confirmed this interaction in the two-hybrid system, by cotransformation of full-length αT-catenin, αE-catenin, αN-catenin and α-catulin bait fusions with prey fusions containing an amino terminal part of β-catenin and nearly full-length plakoglobin (FIG. 7A). In this way, we confirmed the reported interaction between αE-catenin and β-catenin (Aberle et al., 1994; Funayama et al., 1995; Hulsken et al., 1994; Jou et al., 1995), and between αN-catenin and β-catenin (Sehgal et al., 1997). Interestingly, α-catulin does not interact with β-catenin. On the other hand, we demonstrated the presumptive interaction between αT-catenin and β-catenin, and noticed strong blue staining as compared to other positive interactions (FIG. 7A), suggesting that α-catenins bind to β-catenin with the following decreasing strength: αT-catenin >αN-catenin >αE-catenin.

When the interaction with β-catenin was quantified in the two-hybrid system, by using CPRG as a substrate for β-galactosidase, the values found for interaction with αT-catenin were about four times higher than these found for interaction with αE-catenin (FIG. 7B). This confirms that αT-catenin is able to interact in a stronger way to β-catenin than other α-catenins do. The interaction between αT-catenin and β-catenin could be confirmed by coimmunoprecipitation from lysates of HEK-293 cells overexpressing Myc-tagged αT-catenin (FIG. 7C), and also by coimmunoprecipitation from lysates of mouse heart and testis tissues (FIG. 7D). Thus, the interaction between αT-catenin and β-catenin occurs also in vivo.

Example 4

The αT-catenin Protein is Preferentially Expressed in Heart and Testis Tissues

A human cDNA Rapid Scan panel (OriGene Technologies, Rockville, Md.) was screened by PCR for αT-catenin expression. A first PCR reaction revealed expression in heart and testis tissues only, whereas a second, nested PCR amplified low amounts in some other tissues (brain, kidney, liver, skeletal muscle, fetal liver) (FIG. 8A). In comparison to the ubiquitously expressed αE-catenin (FIG. 8A), the novel αT-catenin shows a very restricted expression pattern. Besides the original testis-derived EST clone (Accession Nos. AA393647 and AA400832), one additional αT-catenin-specific EST sequence, derived from kidney, was identified recently (Accession No AW444927). Weak amplification of the αT-catenin transcript is indeed seen by us in kidney tissue (FIG. 8A).

These findings were confirmed by RT-PCR analysis (FIG. 8B) of several mouse tissues. The brain-specific expression of mouse αN-catenin mRNA is in line with the literature (Hirano et al., 1992).

We generated αT-catenin-specific polyclonal antibodies #952, specific for a carboxyterminal peptide of human αT-catenin with sequence C-KIHPLQVMSEFRGRQIY (SEQ ID NO:134). Using serum #952 on several mouse tissue protein lysates, we observed strong expression of αT-catenin in heart, lower levels in testis but hardly any αT-catenin protein in kidney, ovary, spleen or colon tissue, whereas these same tissues contain αE-catenin and β-catenin protein (FIG. 8C). This confirms the observed tissue-specificity of the αT-catenin mRNA (FIG. 8B) at the protein level. Monoclonal antibody 893_32C6S, generated against the same antigenic peptide as serum #952, is specific for human αT-catenin but does not cross-react with mouse αT-catenin (FIG. 17B).

Northern blot analysis confirmed the strong expression of mouse αT-catenin in heart and testis. Different strong signals, which appear smaller (±2000 nt and ±2500 nt) than the full-length mouse αT-catenin mRNA (2,979 nt) on agarose gel, suggest the expression of alternative transcripts of mouse αT-catenin in both organs (FIG. 20). Also in Western blot analysis, some bands with smaller apparent molecular weights (of about 43 kDa, 66 kDa and 86 kDa) were detected in heart and testis lysates (FIG. 21A). Immunodetection of all these bands is competed out by addition of the αT-catenin-specific immunogenic peptide (FIG. 21B). Importantly, the smallest mRNA transcript is very abundant in testis. Correspondingly, the 66-kDa band on Western blot also appears to be stronger than the full-length mouse αT-catenin protein in lysates of testis. As the probes and antibody used are specific for respectively the 3'-end of the αT-catenin transcript or the C-terminal end of the αT-catenin protein, the alternative variants may be N-terminally truncated and possibly deficient for β-catenin binding.

Example 5

Human αT-catenin Can be Detected in Cardiomyocytes and Testis Tissue

Frozen sections of human heart and testis tissue were stained with the monoclonal 892_24D2S antibodies, shown to be specific for αT-catenin. Human αT-catenin protein can be detected in high amounts at intercalated discs, which are the specific heart cell-cell junctions to which actin microfilaments anchor (FIG. 9A and 9B). In testis, weaker but specific staining can be seen in interstitial elongated cells nearby the basement membrane of seminiferous tubules, which are probably peritubular myoid cells (FIG. 11A and 11B). These results suggest that αT-catenin protein is expressed in specific contractile cells of heart and testis tissues.

In double labeling experiments, it co-localizes with αE-catenin (FIG. 10A) as well as N-cadherin (FIG. 10B). The muscle marker desmin can be detected at both intercalated discs and sarcomeric Z-lines, whereas αT-catenin expression is confined to intercalated discs (FIG. 10C). In human testis, αT-catenin protein was detected mainly in spindle-shaped cells surrounding testicular tubuli (FIG. 11). Interestingly, αT-catenin did not co-localize here with αE-catenin, as the latter showed an abundant intratubular expression pattern (FIG. 11A). The αT-catenin expressing cells in testis correspond to desmin-positive cells, and therefore could be identified as peritubular myoid cells (FIG. 11B). These stainings strongly suggest that αT-catenin expression is confined to specific muscle cell types Example 6

αT-catenin Functionally Restores Cell Aggregation in α-catenin-Negative Cancer Cells To assess whether αT-catenin binding to β-catenin has functional implications for the formation of cell-cell contacts, we carried out rescue experiments by overexpression of αT-catenin in round HCT-8/R1 cells lacking α-catenins (Vermeulen et al., 1995; Vermeulen et al., 1999). Vaccinia virus-mediated expression was used to obtain high transient transfection efficiencies (between 30 and 70%). Cell-cell adhesion was found to be restored if neighboring cells were expressing the ectopic protein that became enriched at the cell-cell contacts, whereas solitary expressing cells remained round with diffuse expression of the ectopic protein (FIG. 12A). Moreover, when GFP-tagged αT-catenin was overexpressed in neighboring cells, its enrichment in cell-cell contacts recruited both β-catenin and E-cadherin to these sites (FIG. 12B). However, when αT-catenin was overexpressed for longer time periods, it tended to form cytoplasmic rod-like aggregates.

In order to quantify the restoration of cell-cell adhesion by αT-catenin expression in HCT-8/R1 cells, these cells were transfected with a plasmid encoding Myc-tagged αT-catenin. A stable transfectant was cloned and called HCT-8/R1/T31. Western blotting with polyclonal antiserum #952 showed high expression of αT-catenin protein in this cell line. Immunofluorescent analysis of HCT-8/R1/T31 cells with anti-Myc antibodies showed that the αT-catenin-Myc protein was localized at restored cell-cell contacts (FIG. 13). Components of the adherens junctions (E-cadherin, β-catenin and plakoglobin) were recruited to such αT-catenin positive sites (illustrated in FIG. 13), but also desmosomes (desmoglein-2) and tight junctions (ZO-1, occludin) showed reassembly (illustrated in FIG. 13).

By using the fast aggregation assay, we were able to show that HCT-8/RI/T31 cells are strongly aggregating in contrast to nonaggregating parental HCT-8/R1 cells (FIG. 14). HCT-8/R1/T31 cells aggregated to similar extent as αE-catenin-positive HCT-8/E8 cells and αN-catenin-transfected HRpCαN2 cells, thus showing that αT-catenin is able to functionally restore aggregation. These findings were confirmed using another transfected cell line, HCT-8/E11R1/T14, stably expressing a GFP-αT-catenin fusion protein.

In a slow aggregation assay, αT-catenin-transfected HCT-8/R1/T31 cells were compacting even better than αE-catenin-positive HCT-8/E8 cells or αN-catenin-transfected HRpCαN2 cells (FIG. 15).

TABLE 1

| CTNNA3 exon # | Corresponding Genomic Clone (Name or GenBank Acc. No.) | BAC size (bp) as far as sequenced | Size (bp) of exon-containing contig | position of exon in contig |
|---|---|---|---|---|
| 1 | BAC 162A20 | >9,000 | 8,000 | 2,500-2,600 |
| 2 | BAC 162A20 | >9,000 | 1,000 | |
|   | AC009037.6 | 30,769 | 30,769 | 7,602-7,499 |
| 3 | AC026394.9 | 180,805 | 54,182 | 25,892-26,084 |
|   | AC027668.2 | 32,000 | 9,167 | 91,612-91,804 |
| 4 | AC026394.9 | 180,805 | 23,941 | 17,471-17,637 |
| 5 | AC026394.9 | 180,805 | 11,415 | 541-660 |
| 6 | AC022534.7 | 185,679 | 185,679 | 56,887-56621 |
|   | AC022401.3 | 172,591 | 172,591 | 163,589-163,323 |
| 7 | AC024602.5 | 175,504 | 175,504 | 48,365-48,559 |
|   | AC022534.7 | 185,679 | 185,679 | 17,533-17,330 |
|   | AQ163827.1 | 396 | 396 | 16-289 |
|   | AC022401.3 | 172,591 | 172,591 | 124,236-124,033 |
| 8 | n.a. | n.a. | n.a. | n.a. |
| 9 | n.a. | n.a. | n.a. | n.a. |
| 10 | AQ351427.1 | 476 | 476 | 151-243 |
|   | AC020642.6 | 145,695 | 145,695 | 110,853-110,945 |
|   | AQ355080.1 | 677 | 677 | 151-243 |
| 11 | AC023847.2 | 80,449 | 8,532 | 7,255-7,411 |
|   | AC027668.3 | 200,268 | 140,908 | 93,854-93,699 |
| 12 | AC016819.4 | 136,685 | 17,473 | 4,170-4,370 |
|   | AC027675.5 | 160,439 | 1,919 | 561-761 |
| 13 | AC027675.5 | 160,439 | 2,474 | 208-359 |
| 14 | AC021888.3 | 174,470 | 7,744 | 6,707-6799 |
|   | AC022017.5 | 183,665 | 141,718 | 46,258-46,350 |
|   | AC022024.2 | 369,279 | 2,919 | 2,863-2,919 |
|   | AL592075 | 173,925 | 7,743 | 6,705-6,797 |
| 15 | AC022017.5 | 183,665 | 141,718 | 80,018-80,400 |
|   | AC022024.2 | 369,279 | 8,442 | 3,097-3,278 |
|   | AP001355.2 | 186,290 | 15,133 | 1,474-1,655 |
|   | AL513126.4 | 163,341 | 77,255 | 61,704-561,522 |
| 16 | AC022024.2 | 369,279 | 2,571 | 549-654 |
|   | AP001355.2 | 186,290 | 11,104 | 1,303-1,408 |
|   | AC022017.5 | 183,665 | 21,147 | 1,709-1,818 |
|   | AL513126.4 | 163,341 | 68,244 | 66,959-66,854 |
| 17 | AP001355.2 | 186,290 | 6,741 | 5,376-5,510 |
|   | AL513126.4 | 163,341 | 68,244 | 44,908-44,774 |
| 18 | AP001355.2 | 186,290 | 46,144 | 31,409-31,852 |
|   | PAC 320B7 | >1,000 | 1,000 | |
|   | AC018979.6 | 356,758 | 3,084 | 2,111-2,557 |

TABLE 2

| EXON | exon size | slice donor | intron size | slice acceptor |
|---|---|---|---|---|
|   |   |   | >0.5 kb axxctgggtgaa | CAACGCTCA-1 |

M

TABLE 2-continued

| EXON | exon size | slice donor | | intron size | slice acceptor | |
|---|---|---|---|---|---|---|
| 1 | 170 bp | AAC-AGA-AAG | gtaagaatcaag | >23.2 kb | tttgtgcagcag | -GC-AGC-ATG- |
| | | 170 | | | | 171 |
| 2 | 104 bp | I  I  Q<br>ATA-ATC-CAG | gtattaatacca | >8.6 kb | ttccaattttag | V  T  T<br>GTT-ACC-ACA- |
| | | 274 | | | | 275 |
| 3 | 193 bp | K  E<br>AAA-GAA-A-- | gtgagtactcca | 67 kb | tgtattttcag | S  E  A<br>-GT-GAA-GCT- |
| | | 467 | | | | 468 |
| 4 | 167 bp | V  S  A<br>GTG-TCA-GCT | gtaagtaaaga. | 17.5 kb | tttcaatttcag | F  Q  R<br>TTT-CAA-AGG- |
| | | 634 | | | | 635 |
| 5 | 120 bp | R  Q  Q<br>CGT-CAG-CAG | gtaggagtcaga. | >100 kb | ttaccttctcag | D  L  K<br>GAC-TTA-AAA- |
| | | 754 | | | | 755 |
| 6 | 264 bp | E  L  E<br>GAG-CTG-GAG | gtaagtcgggag. | 39.5 kb | ttcttctcttag | N  L  I<br>AAT-TTA-ATT- |
| | | 1018 | | | | 1019 |
| 7 | 204 bp | M  N  N<br>ATG-AAC-AAC | gtaagtatagtt. | >50 kb | tcttcctttgcag | A  G  K<br>GCT-GGA-AAA- |
| | | 1222 | | | | 1223 |
| 8 | 81 bp | R  R  Q<br>CGC-AGA-CAG | gtgagggaagag. | 9 kb | atttcttctcag | L  R  K<br>CTC-CGC-AAG- |
| | | 1303 | | | | 1304 |
| 9 | 153 bp | L  V  E<br>CTT-GTA-GAG | gtaagcatgcta. | >150 kb | attgtatttaag | V  A  N<br>GTG-GCA-AAT- |
| | | 1456 | | | | 1457 |
| 10 | 93 bp | C  P  Q<br>TGT-CCA-CAG | gtatgacaacta. | 100 kb | ttatctttatag | I  I  N<br>ATT-ATT-AAT- |
| | | 1549 | | | | 1550 |
| 11 | 157 bp | V  S<br>GTA-TCT-G-- | gtatgtttttat. | >2.5 kb | atttacttaag | E  S  H<br>-AA-AGC-CAT- |
| | | 1706 | | | | 1707 |
| 12 | 201 bp | S  T<br>AGT-ACT-G-- | gtaagtcagttg. | >7.2 kb | ttatttaacag | V  I  P<br>-TA-ATT-CCT- |
| | | 1907 | | | | 1908 |
| 13 | 151 bp | M  I  R<br>ATG-ATT-CG- | gtaagtttgctt. | >6.7 kb | ttcttttatag | T  P<br>--G-ACC-CCA- |
| | | 2058 | | | | 2059 |
| 14 | 94 bp | T  D  R<br>ACT-GAT-AGG | gtatgtcacttc. | 34 kb | cacatgttttag | A  K  M<br>GCT-AAG-ATG- |
| | | 2152 | | | | 2153 |
| 15 | 182 bp | F  T  R<br>TTC-ACT-AG- | gtaattatgtgg | 81 kb | attttttccag | G  K<br>--G-GGC-AAA- |
| | | 2334 | | | | 2335 |
| 16 | 106 bp | A  N  Q<br>GCT-AAT-CAG | gtgagttactta. | 22 kb | atgcatatttag | C  P  D<br>TGC-CCA-GAT- |
| | | 2440 | | | | 2441 |
| 17 | 135 bp | M  S  A<br>ATG-TCA-GCT | gtgagtactgcc. | 46 kb | ttttccctacag | L  D  S<br>TTG-GAC-AGT- |
| | | 2575 | | | | 2576 |
| 18 | 445 bp | ATA-TAT-A-- | tttgggatcatt | >200 kb | | |
| | | 3019 | | | | |

TABLE 3

Overview of CTNNA3 exon-specific PCRs

| Exon | Upper Primer | Lower Primer | [MgCl2] (mM) | Product (bp) | A.T. (° C.) |
|---|---|---|---|---|---|
| 1 | FVR 2513 (SEQ ID NO:43)<br>5' TTGCTTGTAACCTCCCCTTT 3' | FVR 2514 (SEQ ID NO:44)<br>5' GCGTGAAAGCCTACGTTTCT 3' | 2 | 395 | 61 |
| 2 | FVR 2515 (SEQ ID NO:45)<br>5' TAATTTGTTACAGGACCTAAGC 3' | FVR 2516 (SEQ ID NO:46)<br>5' TCTTCATTATTCATTTTTCCCAC 3' | 2 | 407 | 55.8 |
| 3 | FVR 2517 (SEQ ID NO:47)<br>5' TATCCCAGGACTGTGTTCTC 3' | FVR 2518 (SEQ ID NO:48)<br>5' TGGAGCCAAAAACAAAACA 3' | 2 | 353 | 59.6 |
| 4 | FVR 2519 (SEQ ID NO:49)<br>5' TGGGGTTGTATTTTTCAGGTG 3' | FVR 2520 (SEQ ID NO:50)<br>5' GCCAGGTTCAGAGAATGAAAT 3' | 2 | 252 | 56.7 |
| 5 | FVR 2521 (SEQ ID NO:51)<br>5' GGACTGAACAGGCTTCTCAT 3' | FVR 2522 (SEQ ID NO:52)<br>5' GCAGGAAGCCTAAAGTGTTC 3' | 2 | 406 | 59.3 |
| 6 | FVR 2523 (SEQ ID NO:53)<br>5' GTCTTTCTCCCATAACCCATT 3' | FVR 2524 (SEQ ID NO:54)<br>5' CGCCAACATGTGGATCTTCT 3' | 2 | 404 | 59.3 |
| 7 | FVR 2525 (SEQ ID NO:55)<br>5' TGAAATGCCATGGAGCTCTAA 3' | FVR 2526 (SEQ ID NO:56)<br>5' ACGGAAAGTATCTCAGCCTAT 3' | 2 | 326 | 57.8 |
| 8 | FVR 2958 (SEQ ID NO:57)<br>5' CCATTGCTTATGTCGTTTTTTC 3' | FVR 2959 (SEQ ID NO:58)<br>5' TTAGCCCCTATGTTTCTGACT 3' | 2 | 156 | 57.8 |
| 9 | FVR 2960 (SEQ ID NO:59)<br>5' AGAAAAGGAAACACAGTGAACT 3' | FVR 2961 (SEQ ID NO:60)<br>5' TTCTCCTGGACTTTAGTGAGTT 3' | 2 | 259 | 56.5 |
| 10 | FVR 2527 (SEQ ID NO:61)<br>5' TGTTGCTGCATTTCCTTGCTA 3' | FVR 2528 (SEQ ID NO:62)<br>5' GCGAGACCTGGTCTCAAAAA 3' | 2 | 267 | 62.4 |
| 11 | FVR 2529 (SEQ ID NO:63)<br>5' GTGCCCATCACCCAAATAGT 3' | FVR 2530 (SEQ ID NO:64)<br>5' CCATGCCTGTCCCAGTATTA 3' | 2 | 300 | 62.4 |
| 12 | FVR 2531 (SEQ ID NO:65)<br>5' CCATTTCCAATGTGCACTCTA 3' | FVR 2532 (SEQ ID NO:66)<br>5' AATTGTGCAGCTGTTATTGGC 3' | 2 | 350 | 61.0 |
| 13 | FVR 2956 (SEQ ID NO:67)<br>5' ACAAAGAGGACAATCTTCTCC 3' | FVR 2957 (SEQ ID NO:68)<br>5' TCAATGGAAGGAAAAGCAAAC 3' | 2 | 217 | 60.8 |
| 14 | FVR 2533 (SEQ ID NO:69)<br>5' TGGGAGTGAAATTGCTGGGT 3' | FVR 2534 (SEQ ID NO:70)<br>5' TAGAGGCTGCCTAGATTGAC 3' | 2 | 301 | 64.3 |
| 15 | FVR 2535 (SEQ ID NO:71)<br>5' TGCTTTTGACATAGTGGAATGA 3' | FVR 2536 (SEQ ID NO:72)<br>5' TGGCACTTGACACTCAGAGA 3' | 2 | 326 | 56.7 |
| 16 | FVR 2537 (SEQ ID NO:73)<br>5' CCGTTCTTTGGGATGCGAAT 3' | FVR 2538 (SEQ ID NO:74)<br>5' GGCAAAGAGCAATTAGCATGA 3' | 2 | 295 | 56.7 |
| 17 | FVR 2539 (SEQ ID NO:75)<br>5' AAGGTACCTGCCATGTGAATA 3' | FVR 2540 (SEQ ID NO:76)<br>5'AGATTTGGTCATGTAAACAAGG 3' | 2 | 313 | 59.3 |
| 18 | FVR 2541 (SEQ ID NO:77)<br>5' CCACGCTTGGCAATAATTAAC 3' | FVR 2542 (SEQ ID NO:78)<br>5'TGCTGACCATACAGAAATGAC 3' | 2 | 552 | 62.8 |

REFERENCES

Aberle, H., S. Butz, J. Stappert, H. Weissig, R. Kemler, and H. Hoschuetzky. (1994). Assembly of the cadherin catenin complex in vitro with recombinant proteins. *J. Cell Sci.* 107: 3655-3663.

Altschul S. F., Warren G., Miller W., Myers E. W., and Lipman D. J. (1990). Basic local alignment search tool. *Journal of Molecular Biology* 215: 403-410.

Altschul, S. F., Madden, T. L., Schäffer, A. A., Zhang, J., Zhang, Z., Miller, W. and Lipman D. J. (1997). "Gapped BLAST and PSI-BLAST: a new generation of protein database search programs", *Nucleic Acids Res.* 25: 3389-3402.

Bonfield J. K., Smith K. F., and Staden R. (1995). A new DNA sequence assembly program. *Nucleic Acids Research* 23: 4992-4999.

Boterberg, T., K. M. Vennekens, M. Thienpont, M. M. Marcel, and M. E. Bracke. 2000. Internalization of the E-cadherin/catenin complex and scattering of human mammary carcinoma cells: MCF-7/AZ after treatment with conditioned medium from human skin squamous carcinoma cells COLO 16. *Cell Adhes. Commun.* 7: 299-310.

Bowles, K. R., Gajarski, R., Porter, P., Goytia, V., Bachinski, L., Roberts, R., Pignatelli, R. and Towbin, J. A. (1996). Gene mapping of familial autosomal dominant dilated cardiomyopathy to chromosome 10q21-23. *J. Clinic. Invest.* 98: 1355-1360.

Chakrabarti, S., J. R. Sisler, and B. Moss. 1997. Compact, synthetic, vaccinia virus early/late promoter for protein expression. *Biotechniques* 23: 1094-7.

Claverie J. M., Hardelin J. P., Legouis R., Levilliers J., Bougueleret L., Mattei M. G., and Petit C. (1993). Characterization and chromosomal assignment of a human cDNA encoding a protein related to the murine 102-kDa cadherin-associated protein (alpha-catenin). *Genomics* 15: 13-20.

Ewing C. M., Ru N., Morton R. A., Robinson J. C., Wheelock M. J., Johnson K. R., Barrett J. C., and Isaacs W. B. (1995). Chromosome 5 suppresses tumorigenicity of PC3 prostate cancer cells: correlation with re-expression of alpha-catenin and restoration of E-cadherin function. *Cancer Research* 55: 4813-4817.

Frischknecht, F., V. Moreau, S. Rottger, S. Gonfloni, I. Reckmann, G. Superti-Furga, and M. Way. 1999. Actin-based motility of vaccinia virus mimics receptor tyrosine kinase signalling. *Nature* 401: 926-929.

Funayama, N., F. Fagotto, P. McCrea, and B. M. Gumbiner. (1995). Embryonic axis induction by the armadillo repeat domain of beta-catenin: evidence for intracellular signaling. *J. Cell Biol.* 128: 959-968.

Furukawa Y., Nakatsuru S., Nagafuchi A., Tsukita S., Muto T., Nakamura Y., and Horii A. (1994). Structure, expression and chromosome assignment of the human catenin (cadherin-associated protein) alpha-1 gene (CTNNA1). *Cytogenetics and Cell Genetics* 65: 74-78.

Giannini A. L., Vivanco M. D. M., and Kypta R. M. (2000). Analysis of beta-catenin aggregation and localization using GFP fusion proteins: Nuclear import of alpha-catenin by the beta-catenin/Tcf complex. *Experimental Cell Research* 255: 207-220.

Gietz, D., A. St Jean, R. A. Woods, and R. H. Schiestl. (1992). Improved method for high efficiency transformation of intact yeast cells. *Nucleic Acids Res.* 20: 1425.

Hazan R. B., Kang L., Roe S., Borgen P. I., and Rimm D. L. (1997). Vinculin is associated with the E-cadherin adhesion complex. *Journal of Biological Chemistry* 272: 32448-32453.

Herrenknecht K., Ozawa M., Eckerskorn C., Lottspeich F., Lenter M., and Kemler R. (1991). The uvomorulin-anchorage protein alpha-catenin is a vinculin homologue. *Proceedings of the National Academy of Sciences of the United States of America* 88: 9156-9160.

Higgins D. G., and Sharp P. M. (1989). Fast and sensitive multiple sequence alignments on a microcomputer. *Computer Applications in the Biosciences* 5: 151-153.

Hirano S., Kimoto N., Shimoyama Y., Hirohashi S., and Takeichi M. (1992). Identification of a neural alpha-catenin as a key regulator of cadherin function and multicellular organization. *Cell* 70: 293-301.

Huber O., Krohn M., and Kemler R. (1997). A specific domain in alpha-catenin mediates binding to beta-catenin or plakoglobin. *Journal of Cell Science* 110: 1759-1765.

Hülsken, J., W. Birchmeier, and J. Behrens. (1994). E-cadherin and APC compete for the interaction with beta-catenin and the cytoskeleton. *J. Cell Biol.* 127: 2061-2069.

Ioannou, P. A., de Jong, P. J. (1996). Construction of bacterial artificial chromosome libraries using the modified P1 (PAC) system. In: Current protocols in human genetics, Dracopoli Ed., John Wiley and Sons, New York.

Janssens B., Staes K., and van Roy F. (1999). Human alpha-catulin, a novel alpha-catenin-like molecule with conserved genomic structure, but deviating alternative splicing. *Biochimica et Biophysica Acta—Gene Structure and Expression* 1447: 341-347.

Johnson R. P., and Craig S. W. (1995). F-actin binding site masked by the intramolecular association of vinculin head and tail domains. *Nature (London)* 373: 261-264.

Jou, T. S., D. B. Stewart, J. Stappert, W. J. Nelson, and J. A. Marrs. (1995). Genetic and biochemical dissection of protein linkages in the cadherin-catenin complex. *Proc. Natl. Acad. Sci. U.S.A.* 92: 5067-5071.

Keirsebilck, A., Bonné, S., Staes, K., van Hengel, J., Nollet, F., Reynolds, A., and van Roy, F. (1998). Molecular cloning of the human p120$^{ctn}$ catenin gene (CTNND1): Expression of multiple alternatively spliced isoforms. *Genomics* 50: 129-146.

Kievits T., Dauwerse J. G., Wiegant J., Devilee P., Breuning M. H., Cornelisse C. J., Van Ommen G. J., and Pearson D. L. (1990). Rapid subchromosomal localization of cosmids by non-radioactive in situ hybridization. *Cytogenetics and Cell Genetics* 53: 134-136.

Kozak M. (1991). Structural features in eukaryotic messenger RNAs that modulate the initiation of translation. *Journal of Biological Chemistry* 266: 19867-19870.

Laemmli, U. K. 1970. Cleavage of structural proteins during the assembly of the head of bacteriophage T4. *Nature* 227: 680-685

Miller J H, 1972. Experiments in Molecular Genetics (Cold spring Harhbor Laboratory, Cold Spring Harbor, N.Y.).

Mount S. M. (1982). A catalogue of splice junction sequences. *Nucleic Acids Research* 10: 459-472.

Nieset J. E., Redfield A. R., Jin F., Knudsen K. A., Johnson K. R., and Wheelock M. J. (1997). Characterization of the interactions of alpha-catenin with alpha-actinin and beta-catenin/plakoglobin. *Journal of Cell Science* 110: 1013-1022.

Parkinson, J. E., and G. L. Smith. 1994. Vaccinia virus gene A36R encodes a M(r) 43-50 K protein on the surface of extracellular enveloped virus. *Virology* 204: 376-90.

Pokutta S., and Weis W. I. (2000). Structure of the dimerization and beta-catenin-binding region of alpha-catenin. *Molecular Cell* 5: 533-543.

Quandt K., Frech K., Karas H., Wingender E., and Werner T. (1995) MatInd and Matinspector—New fast and versatile tools for detection of consensus matches in nucleotide sequence data. *Nucleic Acid Research* 23:4878-4884.

Rudiger M. (1998). Vinculin and alpha-catenin: shared and unique functions in adherens junctions. *Bioessays* 20: 733-740.

Sanger F., Nicklen S., and Coulson A. (1977). DNA sequencing with chain-terminating inhibitors. *Proceedings of the National Academy of Sciences of the United States of America* 74: 5463.

Sehgal, R. N. M., B. M. Gumbiner, and L. F. Reichardt. 1997. Antagonism of cell adhesion by an alpha-catenin mutant, and of the Wnt-signaling pathway by alpha-catenin in Xenopus embryos. *J. Cell Biol.* 139: 1033-1046.

Thompson J. D., Higgins D. G., and Gibson T. J. (1994). CLUSTAL W: improving the sensitivity of progressive multiple sequence alignment through sequence weighting, position-specific gap penalties and weight matrix choice. *Nucleic Acids Research* 22: 4673-4680.

van Hengel J., Gohon L., Bruyneel E., Vermeulen S., Cornelissen M., Mareel M., and van Roy F. (1997). Protein kinase C activation upregulates intercellular adhesion of alpha-catenin-negative human colon cancer cell variants via induction of desmosomes. *Journal of Cell Biology* 137: 1103-1116.

van Hengel J., Nollet F., Berx G., van Roy N., Speleman F., and van Roy F. (1995). Assignment of the human b-catenin gene (CTNNB1) to 3p22-p21.3 by fluorescence in situ hybridization. *Cytogenetics and Cell Genetics* 70: 68-70.

Watabe M., Nagafuchi A., Tsukita S., and Takeichi M. (1994). Induction of polarized cell-cell association and retardation of growth by activation of the E-cadherin catenin adhesion system in a dispersed carcinoma line. *Journal of Cell Biology* 127: 247-256.

Watabe-Uchida M., Uchida N., Imamura Y., Nagafuchi A., Fujimoto K., Uemura T., Vermeulen S., van Roy F., Adamson E. D., and Takeichi M. (1998). Alpha-Catenin-vinculin interaction functions to organize the apical junctional complex in epithelial cells. *Journal of Cell Biology* 142: 847-857.

Zhang J. S., Nelson M., Wang L., Liu W. G., Qian C. P., Shridhar V., Urrutia R., and Smith D. I. (1998). Identification and chromosomal localization of CTNNAL1, a novel protein homologous to alpha-catenin. *Genomics* 54: 149-154.

What is claimed is:

1. An isolated nucleic acid sequence encoding a polypeptide comprising the sequence presented in SEQ ID NO:2.

2. The nucleic acid sequence of claim 1, wherein said nucleic acid comprises the sequence presented in SEQ ID NO:1.

3. The nucleic acid sequence according to claim 2 further comprising a promoter region.

4. The nucleic acid sequence of claim 3, wherein said promoter region comprises the sequence presented in SEQ ID NO:3.

5. A composition for treating cadherin-catenin related diseases, said composition comprising: the nucleic acid of claim 1 in a pharmaceutically acceptable form.

6. The composition of claim 5, wherein the cadherin-catenin related disease is selected from the group consisting of cancer, cardiomyopathy, dilated cardiomyopathy, male infertility, and mixtures thereof.

7. The isolated nucleic acid sequence according to claim 1 further comprising a promoter region.

8. An isolated or recombinant nucleic acid sequence comprising the sequence of SEQ ID NO:3 fused to a nucleic acid sequence encoding a polypeptide comprising the sequence of SEQ ID NO:2.

9. An isolated nucleic acid sequence encoding a polypeptide comprising the sequence presented in SEQ ID NO:2.

10. An isolated or recombinant nucleic acid sequence useful for expressing a polypeptide, said isolated or recombinant nucleic acid sequence comprising:
   a first nucleic acid sequence consituting a promoter for encoding a polypeptide comprising the sequence presented in SEQ ID NO:2.

11. The isolated or recombinant nucleic acid sequence of claim 10, further comprising a second nucleic acid sequence, operatively positioned with respect to said first nucleic acid sequence, constituting a means for promoting expression of said first nucleic acid sequence.

* * * * *

UNITED STATES PATENT AND TRADEMARK OFFICE
CERTIFICATE OF CORRECTION

PATENT NO. : 7,341,866 B2  
APPLICATION NO. : 10/345092  
DATED : March 11, 2008  
INVENTOR(S) : Frans Van Roy et al.

Page 1 of 2

It is certified that error appears in the above-identified patent and that said Letters Patent is hereby corrected as shown below:

On the title page:
In ITEM (12) United States Patent  change "Roy et al." to --Van Roy et al.--

In ITEM (63) Related U.S. Application Data  after "filed on Jun. 28, 2001." change the period to a comma --,-- and insert --which claims priority to Provisional application No. 60/218,309, filed on July 14, 2000.--

| | | |
|---|---|---|
| COLUMN 2, | LINE 37, | change "expressed selected" to --expressed in selected-- |
| COLUMN 5, | LINE 7, | delete "wa" and after "bp" and before "amino acid" insert --was obtained, containing an open reading frame of 895-- |
| COLUMN 5, | LINE 30, | change "Huber et a/." to --Huber et al.-- |
| COLUMN 11, | LINE 26, | change "CONCERTT" to --CONCERT™-- |
| COLUMN 19, | LINE 39, | change "(Millipore, Bredford, Mass.)" to --(Millipore, Bedford, Mass.)-- |
| COLUMN 20, | LINE 44, | change "so" to --solution-- and before "DNA," insert --(DAPI; RocheDiagnostics, Mannheim, Germany) to mark nuclear-- |
| COLUMN 23, | LINE 1, | change "Genomic clone 164N 16" to --Genomic clone 164N16-- |
| COLUMN 32, | LINE 28, | change "Harhbor Laboratory," to --Harbor Laboratory,-- |

UNITED STATES PATENT AND TRADEMARK OFFICE
CERTIFICATE OF CORRECTION

PATENT NO. : 7,341,866 B2
APPLICATION NO. : 10/345092
DATED : March 11, 2008
INVENTOR(S) : Frans Van Roy et al.

It is certified that error appears in the above-identified patent and that said Letters Patent is hereby corrected as shown below:

CLAIM 9, COLUMN 100, LINE 53, change "comprising" to --consisting of--
CLAIM 10, COLUMN 100, LINE 57, change "consituting" to --constituting--

Signed and Sealed this

Seventh Day of July, 2009

JOHN DOLL
*Acting Director of the United States Patent and Trademark Office*

SEQUENCE LISTING

```
<160> NUMBER OF SEQ ID NOS: 134

<210> SEQ ID NO 1
<211> LENGTH: 3024
<212> TYPE: DNA
<213> ORGANISM: Homo sapiens
<220> FEATURE:
<221> NAME/KEY: CDS
<222> LOCATION: (176)..(2863)

<400> SEQUENCE: 1
caacgctcag cgaaattgac tgccccactg tcatctgcct ctcaatttgg tactctgtaa      60
ctctgtgacc accaagaagc cttttccgt cccccacaaa gctcttttg gaaaattccc      120 tacgggagct gaattttaag cccatttact ttataggaag aaacagaaag gcagc atg     178
                                                                Met
                                                                  1 tca gct gaa aca cca atc aca ttg aat atc gat cct cag gat ctg cag      226
Ser Ala Glu Thr Pro Ile Thr Leu Asn Ile Asp Pro Gln Asp Leu Gln
              5                  10                  15 gtc caa aca ttc acc gtg gag aag cta ctg gag cct ctc ata atc cag      274
Val Gln Thr Phe Thr Val Glu Lys Leu Leu Glu Pro Leu Ile Ile Gln
         20                  25                  30 gtt acc aca ctt gta aac tgt ccc cag aac cct tcc agc agg aaa aaa      322
Val Thr Thr Leu Val Asn Cys Pro Gln Asn Pro Ser Ser Arg Lys Lys
     35                  40                  45 gga cgt tcg aaa aga gcc agt gtc ctt cta gct tct gtg gag gaa gca      370
Gly Arg Ser Lys Arg Ala Ser Val Leu Leu Ala Ser Val Glu Glu Ala
 50                  55                  60                  65 act tgg aat tta tta gac aag gga gag aag att gcc cag gaa gct aca      418
Thr Trp Asn Leu Leu Asp Lys Gly Glu Lys Ile Ala Gln Glu Ala Thr
                 70                  75                  80 gtt tta aag gat gag ctt acg gct tca ctt gag gaa gtt cgc aaa gaa      466
Val Leu Lys Asp Glu Leu Thr Ala Ser Leu Glu Glu Val Arg Lys Glu
             85                  90                  95 agt gaa gct ctg aaa gta tca gct gag aga ttt aca gat gac ccc tgt      514
Ser Glu Ala Leu Lys Val Ser Ala Glu Arg Phe Thr Asp Asp Pro Cys
        100                 105                 110 ttt ctc cca aaa agg gag gct gtg gtt caa gct gcc cgt gcc ttg ctg      562
Phe Leu Pro Lys Arg Glu Ala Val Val Gln Ala Ala Arg Ala Leu Leu
    115                 120                 125 gct gcg gtg acg aga ctc ctt atc ctt gcg gac atg att gat gtc atg      610
Ala Ala Val Thr Arg Leu Leu Ile Leu Ala Asp Met Ile Asp Val Met
130                 135                 140                 145 tgc ctc ttg caa cat gtg tca gct ttt caa agg aca ttt gag act ctc      658
Cys Leu Leu Gln His Val Ser Ala Phe Gln Arg Thr Phe Glu Thr Leu
                150                 155                 160
```

-continued

| | |
|---|---|
| aaa aat gtt gcc aac aaa tct gac ctc cag aaa acc tac cag aag ctt<br>Lys Asn Val Ala Asn Lys Ser Asp Leu Gln Lys Thr Tyr Gln Lys Leu<br>             165                   170                   175 | 706 |
| gga aag gag ctg gaa aat ttg gat tat tta gcc ttc aaa cgt cag cag<br>Gly Lys Glu Leu Glu Asn Leu Asp Tyr Leu Ala Phe Lys Arg Gln Gln<br>180                   185                   190 | 754 |
| gac tta aaa tct cca aat cag aga gat gaa att gca gga gcc cga gct<br>Asp Leu Lys Ser Pro Asn Gln Arg Asp Glu Ile Ala Gly Ala Arg Ala<br>195                   200                   205 | 802 |
| tca ctg aag gag aac tct ccc ctc ttg cat tca att tgt tca gct tgt<br>Ser Leu Lys Glu Asn Ser Pro Leu Leu His Ser Ile Cys Ser Ala Cys<br>210                   215                   220               225 | 850 |
| ttg gag cat tct gat gtt gct tcc ctc aaa gca agc aag gac aca gtt<br>Leu Glu His Ser Asp Val Ala Ser Leu Lys Ala Ser Lys Asp Thr Val<br>                   230                   235                   240 | 898 |
| tgt gaa gaa att cag aat gct ctc aat gta att tca aat gct tca caa<br>Cys Glu Glu Ile Gln Asn Ala Leu Asn Val Ile Ser Asn Ala Ser Gln<br>                   245                   250                   255 | 946 |
| ggg atc cag aat atg aca acc cca cca gaa cct cag gca gca acc ctg<br>Gly Ile Gln Asn Met Thr Thr Pro Pro Glu Pro Gln Ala Ala Thr Leu<br>             260                   265                   270 | 994 |
| gga agt gcc ctt gat gag ctg gag aat tta att gtc ctg aat cca ctc<br>Gly Ser Ala Leu Asp Glu Leu Glu Asn Leu Ile Val Leu Asn Pro Leu<br>275                   280                   285 | 1042 |
| aca gta act gag gag gaa ata cga cca tca cta gag aaa cgc ctt gaa<br>Thr Val Thr Glu Glu Glu Ile Arg Pro Ser Leu Glu Lys Arg Leu Glu<br>290                   295                   300                   305 | 1090 |
| gcc att atc agt ggg gct gct ctg ctg gcg gat tct tca tgt acg agg<br>Ala Ile Ile Ser Gly Ala Ala Leu Leu Ala Asp Ser Ser Cys Thr Arg<br>                   310                   315                   320 | 1138 |
| gac tta cac cga gag cgg att atc gca gaa tgc aac gcc att cgc cag<br>Asp Leu His Arg Glu Arg Ile Ile Ala Glu Cys Asn Ala Ile Arg Gln<br>             325                   330                   335 | 1186 |
| gct ctt cag gat ctg ctt tca gag tac atg aac aac gct gga aaa aaa<br>Ala Leu Gln Asp Leu Leu Ser Glu Tyr Met Asn Asn Ala Gly Lys Lys<br>                   340                   345                   350 | 1234 |
| gaa agg agt aat acc ctg aat att gct tta gac aac atg tgt aag aag<br>Glu Arg Ser Asn Thr Leu Asn Ile Ala Leu Asp Asn Met Cys Lys Lys<br>355                   360                   365 | 1282 |
| aca aga gac ctt cgc aga cag ctc cgc aag gct att ata gat cat gtg<br>Thr Arg Asp Leu Arg Arg Gln Leu Arg Lys Ala Ile Ile Asp His Val<br>370                   375                   380                   385 | 1330 |
| tca gac tct ttc ctg gat acg aca gtc cct ctt ttg gtt ctc att gaa<br>Ser Asp Ser Phe Leu Asp Thr Thr Val Pro Leu Leu Val Leu Ile Glu<br>                   390                   395                   400 | 1378 |
| gct gct aag aat ggc cgg gaa aag gaa ata aaa gaa tat gct gcg ata<br>Ala Ala Lys Asn Gly Arg Glu Lys Glu Ile Lys Glu Tyr Ala Ala Ile<br>                   405                   410                   415 | 1426 |
| ttt cat gaa cac acc agc agg ctt gta gag gtg gca aat ctt gct tgt<br>Phe His Glu His Thr Ser Arg Leu Val Glu Val Ala Asn Leu Ala Cys<br>             420                   425                   430 | 1474 |
| tcc atg tca aca aat gaa gat gga att aaa att gtc aaa att gca gcc<br>Ser Met Ser Thr Asn Glu Asp Gly Ile Lys Ile Val Lys Ile Ala Ala<br>435                   440                   445 | 1522 |
| aat cat ttg gaa acc ttg tgt cca cag att att aat gct gca ctt gct<br>Asn His Leu Glu Thr Leu Cys Pro Gln Ile Ile Asn Ala Ala Leu Ala<br>450                   455                   460               465 | 1570 |
| ttg gct gca aga ccc aaa agt caa gcg gtc aaa aac acc atg gaa atg<br>Leu Ala Ala Arg Pro Lys Ser Gln Ala Val Lys Asn Thr Met Glu Met<br>                   470                   475                   480 | 1618 |

```
tac aag cgt aca tgg gag aat cat ata cat gtc ctc act gaa gcc gta      1666
Tyr Lys Arg Thr Trp Glu Asn His Ile His Val Leu Thr Glu Ala Val
            485                 490                 495 gat gac att aca agc att gat gac ttc ctt gct gta tct gaa agc cat      1714
Asp Asp Ile Thr Ser Ile Asp Asp Phe Leu Ala Val Ser Glu Ser His
        500                 505                 510 atc ttg gaa gat gtc aac aag tgt atc ata gcc tta aga gac cag gat      1762
Ile Leu Glu Asp Val Asn Lys Cys Ile Ile Ala Leu Arg Asp Gln Asp
    515                 520                 525 gct gat aat tta gac cgt gct gcg ggt gct atc aga ggc cgg gca gca      1810
Ala Asp Asn Leu Asp Arg Ala Ala Gly Ala Ile Arg Gly Arg Ala Ala
530                 535                 540                 545 aga gtt gct cac atc gtc acg ggt gaa atg gac agt tac gag cca ggg      1858
Arg Val Ala His Ile Val Thr Gly Glu Met Asp Ser Tyr Glu Pro Gly
                550                 555                 560 gct tac acg gaa ggt gta atg aga aat gtt aac ttc ctt aca agt act      1906
Ala Tyr Thr Glu Gly Val Met Arg Asn Val Asn Phe Leu Thr Ser Thr
            565                 570                 575 gta att cct gaa ttt gta aca caa gtg aat gtt gcc ttg gaa gcc tta      1954
Val Ile Pro Glu Phe Val Thr Gln Val Asn Val Ala Leu Glu Ala Leu
        580                 585                 590 agc aaa agc tca ttg aat gtg ttg gat gat aat caa ttt gtg gac atc      2002
Ser Lys Ser Ser Leu Asn Val Leu Asp Asp Asn Gln Phe Val Asp Ile
    595                 600                 605 tca aag aag atc tat gat aca att cat gat atc aga tgt tca gtc atg      2050
Ser Lys Lys Ile Tyr Asp Thr Ile His Asp Ile Arg Cys Ser Val Met
610                 615                 620                 625 atg att cgg acc cca gag gaa ctg gag gat gtt tct gac ctt gaa gag      2098
Met Ile Arg Thr Pro Glu Glu Leu Glu Asp Val Ser Asp Leu Glu Glu
                630                 635                 640 gaa cac gag gtc cgc agt cac acc agc att cag acc gaa ggg aaa act      2146
Glu His Glu Val Arg Ser His Thr Ser Ile Gln Thr Glu Gly Lys Thr
            645                 650                 655 gat agg gct aag atg act caa ctg cct gag gca gaa aaa gaa aag att      2194
Asp Arg Ala Lys Met Thr Gln Leu Pro Glu Ala Glu Lys Glu Lys Ile
        660                 665                 670 gct gag caa gtt gct gat ttc aag aaa gta aag agt aag ctg gat gct      2242
Ala Glu Gln Val Ala Asp Phe Lys Lys Val Lys Ser Lys Leu Asp Ala
    675                 680                 685 gag att gag ata tgg gat gat aca agc aac gac atc att gtt ctg gcc      2290
Glu Ile Glu Ile Trp Asp Asp Thr Ser Asn Asp Ile Ile Val Leu Ala
690                 695                 700                 705 aag aac atg tgt atg atc atg atg gag atg aca gac ttc act agg ggc      2338
Lys Asn Met Cys Met Ile Met Met Glu Met Thr Asp Phe Thr Arg Gly
                710                 715                 720 aaa gga cca cta aag cat aca act gat gtg atc tat gca gcg aaa atg      2386
Lys Gly Pro Leu Lys His Thr Thr Asp Val Ile Tyr Ala Ala Lys Met
            725                 730                 735 ata tca gaa tca gga tca agg atg gat gtc ctt gct cgg cag att gct      2434
Ile Ser Glu Ser Gly Ser Arg Met Asp Val Leu Ala Arg Gln Ile Ala
        740                 745                 750 aat cag tgc cca gat cca tct tgt aaa cag gac ttg ttg gcc tac ctg      2482
Asn Gln Cys Pro Asp Pro Ser Cys Lys Gln Asp Leu Leu Ala Tyr Leu
    755                 760                 765 gaa cag att aag ttc tac tcc cac caa ctg aaa atc tgc agt caa gtt      2530
Glu Gln Ile Lys Phe Tyr Ser His Gln Leu Lys Ile Cys Ser Gln Val
770                 775                 780                 785 aaa gct gag atc cag aac ctg gga gga gag ctc atc atg tca gct ttg      2578
Lys Ala Glu Ile Gln Asn Leu Gly Gly Glu Leu Ile Met Ser Ala Leu
```

-continued

```
                    790                 795                 800
gac agt gtc aca tcc ctg atc caa gca gcc aaa aat tta atg aat gct      2626
Asp Ser Val Thr Ser Leu Ile Gln Ala Ala Lys Asn Leu Met Asn Ala
            805                 810                 815 gta gtg caa aca gtg aaa atg tct tac att gcc tca acc aag atc atc      2674
Val Val Gln Thr Val Lys Met Ser Tyr Ile Ala Ser Thr Lys Ile Ile
        820                 825                 830 cga atc cag agt cct gct ggg ccc cgg cac cca gtt gtg atg tgg aga      2722
Arg Ile Gln Ser Pro Ala Gly Pro Arg His Pro Val Val Met Trp Arg
    835                 840                 845 atg aag gct cct gca aaa aaa ccc ttg att aaa aga gag aag cca gag      2770
Met Lys Ala Pro Ala Lys Lys Pro Leu Ile Lys Arg Glu Lys Pro Glu
850                 855                 860                 865 gaa acg tgt gca gct gtc aga cga ggc tca gca aag aaa aaa atc cat      2818
Glu Thr Cys Ala Ala Val Arg Arg Gly Ser Ala Lys Lys Lys Ile His
                870                 875                 880 cca ttg caa gtc atg agt gaa ttt aga gga aga caa atc tac tga          2863
Pro Leu Gln Val Met Ser Glu Phe Arg Gly Arg Gln Ile Tyr
            885                 890                 895 aaccactatt ctacatatag tgcctatatg acaaaatcct gcctaaccac actgctttat    2923
tttacactta agaagttctg taatttcact aagttttggt gtttaactca caaataacat    2983
aaaatattgg gcgctaaatc aacaaaagca atatataaaa a                        3024

<210> SEQ ID NO 2
<211> LENGTH: 895
<212> TYPE: PRT
<213> ORGANISM: Homo sapiens

<400> SEQUENCE: 2

Met Ser Ala Glu Thr Pro Ile Thr Leu Asn Ile Asp Pro Gln Asp Leu
 1               5                  10                  15

Gln Val Gln Thr Phe Thr Val Glu Lys Leu Leu Glu Pro Leu Ile Ile
            20                  25                  30

Gln Val Thr Thr Leu Val Asn Cys Pro Gln Asn Pro Ser Ser Arg Lys
        35                  40                  45

Lys Gly Arg Ser Lys Arg Ala Ser Val Leu Leu Ala Ser Val Glu Glu
    50                  55                  60

Ala Thr Trp Asn Leu Leu Asp Lys Gly Glu Lys Ile Ala Gln Glu Ala
65                  70                  75                  80

Thr Val Leu Lys Asp Glu Leu Thr Ala Ser Leu Glu Glu Val Arg Lys
                85                  90                  95

Glu Ser Glu Ala Leu Lys Val Ser Ala Glu Arg Phe Thr Asp Asp Pro
            100                 105                 110

Cys Phe Leu Pro Lys Arg Glu Ala Val Gln Ala Ala Arg Ala Leu
        115                 120                 125

Leu Ala Val Thr Arg Leu Leu Ile Leu Ala Asp Met Ile Asp Val
    130                 135                 140

Met Cys Leu Leu Gln His Val Ser Ala Phe Gln Arg Thr Phe Glu Thr
145                 150                 155                 160

Leu Lys Asn Val Ala Asn Lys Ser Asp Leu Gln Lys Thr Tyr Gln Lys
                165                 170                 175

Leu Gly Lys Glu Leu Glu Asn Leu Asp Tyr Leu Ala Phe Lys Arg Gln
            180                 185                 190

Gln Asp Leu Lys Ser Pro Asn Gln Arg Asp Glu Ile Ala Gly Ala Arg
        195                 200                 205
```

-continued

```
Ala Ser Leu Lys Glu Asn Ser Pro Leu Leu His Ser Ile Cys Ser Ala
        210                 215                 220

Cys Leu Glu His Ser Asp Val Ala Ser Leu Lys Ala Ser Lys Asp Thr
225                 230                 235                 240

Val Cys Glu Glu Ile Gln Asn Ala Leu Asn Val Ile Ser Asn Ala Ser
                245                 250                 255

Gln Gly Ile Gln Asn Met Thr Thr Pro Pro Glu Pro Gln Ala Ala Thr
            260                 265                 270

Leu Gly Ser Ala Leu Asp Glu Leu Glu Asn Leu Ile Val Leu Asn Pro
        275                 280                 285

Leu Thr Val Thr Glu Glu Ile Arg Pro Ser Leu Glu Lys Arg Leu
290                 295                 300

Glu Ala Ile Ile Ser Gly Ala Ala Leu Leu Ala Asp Ser Ser Cys Thr
305                 310                 315                 320

Arg Asp Leu His Arg Glu Arg Ile Ile Ala Glu Cys Asn Ala Ile Arg
                325                 330                 335

Gln Ala Leu Gln Asp Leu Leu Ser Glu Tyr Met Asn Asn Ala Gly Lys
            340                 345                 350

Lys Glu Arg Ser Asn Thr Leu Asn Ile Ala Leu Asp Asn Met Cys Lys
        355                 360                 365

Lys Thr Arg Asp Leu Arg Arg Gln Leu Arg Lys Ala Ile Ile Asp His
    370                 375                 380

Val Ser Asp Ser Phe Leu Asp Thr Thr Val Pro Leu Leu Val Leu Ile
385                 390                 395                 400

Glu Ala Ala Lys Asn Gly Arg Glu Lys Glu Ile Lys Glu Tyr Ala Ala
                405                 410                 415

Ile Phe His Glu His Thr Ser Arg Leu Val Glu Val Ala Asn Leu Ala
            420                 425                 430

Cys Ser Met Ser Thr Asn Glu Asp Gly Ile Lys Ile Val Lys Ile Ala
        435                 440                 445

Ala Asn His Leu Glu Thr Leu Cys Pro Gln Ile Ile Asn Ala Ala Leu
    450                 455                 460

Ala Leu Ala Ala Arg Pro Lys Ser Gln Ala Val Lys Asn Thr Met Glu
465                 470                 475                 480

Met Tyr Lys Arg Thr Trp Glu Asn His Ile His Val Leu Thr Glu Ala
                485                 490                 495

Val Asp Asp Ile Thr Ser Ile Asp Asp Phe Leu Ala Val Ser Glu Ser
            500                 505                 510

His Ile Leu Glu Asp Val Asn Lys Cys Ile Ile Ala Leu Arg Asp Gln
        515                 520                 525

Asp Ala Asp Asn Leu Asp Arg Ala Ala Gly Ala Ile Arg Gly Arg Ala
    530                 535                 540

Ala Arg Val Ala His Ile Val Thr Gly Glu Met Asp Ser Tyr Glu Pro
545                 550                 555                 560

Gly Ala Tyr Thr Glu Gly Val Met Arg Asn Val Asn Phe Leu Thr Ser
                565                 570                 575

Thr Val Ile Pro Glu Phe Val Thr Gln Val Asn Val Ala Leu Glu Ala
            580                 585                 590

Leu Ser Lys Ser Ser Leu Asn Val Leu Asp Asp Asn Gln Phe Val Asp
        595                 600                 605

Ile Ser Lys Lys Ile Tyr Asp Thr Ile His Asp Ile Arg Cys Ser Val
    610                 615                 620

Met Met Ile Arg Thr Pro Glu Glu Leu Glu Asp Val Ser Asp Leu Glu
```

```
                625                 630                 635                 640

Glu Glu His Glu Val Arg Ser His Thr Ser Ile Gln Thr Glu Gly Lys
                    645                 650                 655

Thr Asp Arg Ala Lys Met Thr Gln Leu Pro Glu Ala Glu Lys Glu Lys
            660                 665                 670

Ile Ala Glu Gln Val Ala Asp Phe Lys Lys Val Lys Ser Lys Leu Asp
        675                 680                 685

Ala Glu Ile Glu Ile Trp Asp Asp Thr Ser Asn Asp Ile Ile Val Leu
    690                 695                 700

Ala Lys Asn Met Cys Met Ile Met Met Glu Met Thr Asp Phe Thr Arg
705                 710                 715                 720

Gly Lys Gly Pro Leu Lys His Thr Thr Asp Val Ile Tyr Ala Ala Lys
                725                 730                 735

Met Ile Ser Glu Ser Gly Ser Arg Met Asp Val Leu Ala Arg Gln Ile
            740                 745                 750

Ala Asn Gln Cys Pro Asp Pro Ser Cys Lys Gln Asp Leu Leu Ala Tyr
        755                 760                 765

Leu Glu Gln Ile Lys Phe Tyr Ser His Gln Leu Lys Ile Cys Ser Gln
    770                 775                 780

Val Lys Ala Glu Ile Gln Asn Leu Gly Gly Glu Leu Ile Met Ser Ala
785                 790                 795                 800

Leu Asp Ser Val Thr Ser Leu Ile Gln Ala Ala Lys Asn Leu Met Asn
                805                 810                 815

Ala Val Val Gln Thr Val Lys Met Ser Tyr Ile Ala Ser Thr Lys Ile
            820                 825                 830

Ile Arg Ile Gln Ser Pro Ala Gly Pro Arg His Pro Val Val Met Trp
        835                 840                 845

Arg Met Lys Ala Pro Ala Lys Lys Pro Leu Ile Lys Arg Glu Lys Pro
    850                 855                 860

Glu Glu Thr Cys Ala Ala Val Arg Arg Gly Ser Ala Lys Lys Lys Ile
865                 870                 875                 880

His Pro Leu Gln Val Met Ser Glu Phe Arg Gly Arg Gln Ile Tyr
                885                 890                 895

<210> SEQ ID NO 3
<211> LENGTH: 3412
<212> TYPE: DNA
<213> ORGANISM: Homo sapiens
<220> FEATURE:
<223> OTHER INFORMATION: promoter sequence alpha-Tcatenin

<400> SEQUENCE: 3
ggatccagca cacaagagag attagccttt ggtaagagca agaggacttc ttgcatttta    60
ataggaggga gggtagagaa gatgaggctc ggtgttagtg ggtttataga tttgatgatg   120
gaaagatgtg aaacatcttc cagatggctt ctgttcttct tagtgaggca ggagagttgg   180
ttagctgcta ataataagga tggttgggaa gggagagtga gaaacatttt tttttttgt    240 attaatagta cataagacct tcaaatcagg ggcagattca tttagattca cctaaaatac   300
ctgacaaggt gccagaagta tttatcacat atttttgaaa aaatggtttt taattatcac   360
aaacagggat tattcctagc tttaaatctc attttagaaa ggtattatgg ctgttcagaa   420
aattacatat ttttaaagcc cgaacctgaa attgccagta ttttgagata ttatggacag   480
atgaaatgga ctcatggttc atgcaaaagt gattttcatt ctataaggga ttttattgac   540
aagaagaaac tactccattc tgactaaaga acatattgca ccctggagga tttatttcc    600
```

```
aagagaggct actgacaggg atagaattat cttcttttg gaggcctccc ttctctcctg     660
taatcttcta gctggcgcct aacacagggc tctgcatcaa ggggcttctc aatacatcca     720
attgaatgac tttgtttggg gccggtcctg atgcccagaa cgaaaaaact tacttttgat     780
tacctcggga gaattgctag taatggccct gatttattct ctctcttttt tctctctttt     840
ttttttcccc agctcttcta ccctcaatgt ttgattgctt gcaagaggca tgtgagccaa     900
aattttaaag tttgcaaagt ataaagaaag gaaacaagta aatagggaag gagaataaat     960
actgaacaag actgggcaag gtgacaagaa agaactactg tgaaaatctg gaagagggcc    1020
aggatgcaaa atgcaggggc tgtgtagttt acaggaacta tttagcctcc agcatgcctc    1080
agcgatcaca cagagaaagg cagatttctc tgcttttgtc tcctacccta tagttagcta    1140
tggaaatttg acataggtga tatatgtttt ctgtcagcaa actgatacaa atacagagga    1200
ccatggggcc tgtgatcaac aaatccaacg tgatttgaat tgctaggagg ggacctcttg    1260
tggctatagt gggaaatact tcagctaaat actaccttgg aggctgcaga tattttatg    1320 aaggaattaa aaaaaaaccc actataaaag ctctttaaaa ttacatttca gatatttata    1380
atatttaatt gttttgataa caccaaattc tgtaagaagg ttttatctgt attgcatctc    1440
tgaagagttc agtgtaattt aaagctcttc agcttttatc catttaattc acatatcctc    1500
tgaaaagcaa atgaaaagaa taagagttct catctacatt ttgtaggtgg aaaggagagg    1560
tacagggcag gtaagtaact tattgtggtt tcacagcagg acaagctagg cttatgatag    1620
aatttggata tctcatcttg ggctcaattc aacagtcctg gtttggaaaa cattcattat    1680
taaagctcta aaacaaaacc tgctattttg caagtgtcaa gtgatttctt tattcaagaa    1740
aagatggatt gagagacata aaacttactc tttgtttcac tgtgaaaaga tgctattcct    1800
agattctcca gggggaaaaa gctgctttaa aaaaatctgg ggaggatagc atgttagcaa    1860
ctaagaatct ttagataaat atattgtcaa ttatgcccat tttaaaggta gctacataaa    1920
aatacagttg ttttgaaggc tatcctgaaa atcatataaa atgaactcct ttcatagttg    1980
attctctgac agttcccaga ccctgccttt cctcttggct ccctgaaatt tgtgctaaga    2040
gtatctggag agccaataaa taaatgcttt cttttattt tgaattcagc cttttaagaa    2100
caggactgcc aaaactcaaa caagtagttc atattttagt tagcacctct tgttttagaa    2160
gctattagaa gaaagtcgga aaaatggtaa tgtccaagga aatgccacag aagttcgagt    2220
gggatgtcaa ggaattgatg aaatgataaa gattgtttca gtggatgtga agatattgag    2280
ggagaagata tcaaaaaaaa gggaaaagga aatgtgaaaa agaatagtca tagagagaaa    2340
aaataaattt tggtggagaa gacttttttt tttggtggct taaatttaat aatgggttaa    2400
cctattgagt ttttggtaaa tcttcagttt agattcttta ctgataatga tgtggttcct    2460
cataaatact ggaaggagag agtgtgatgc ttggtacaag ggatgagaca ggtaatattt    2520
cagaagaaga aaaatacgat ctcagatgtg acacatggcc ttgatgccat catctctagg    2580
gttctgaaga cattgaattt tacataattg atcttttgat gtgaggattt cctggactct    2640
tgttttccct gctttatcat ttttcacttt caataattcc agcctttggc tttaattaga    2700
tagaagaggt tcttcttttg gaaaggaact agagaaatgc aaatctaaac ttattcagag    2760
ctatgtttgt aggtctctag gcaaagtatg tgtctggcct ttttcaacga agtatttca    2820 gtaacaagtt gtcagtgagg tcagtgacta gcggttcagg attagatacc acccaccctg    2880
gcttgtaacc tcccctttct ttcttatcct gggtgaacaa cgctcagcga aattgactgc    2940
```

```
cccactgtca tctgcctctc aatttggtac tctgtaactc tgtgaccacc aagaagcctt    3000
tttccgtccc ccacaaagct ctttttggaa aattccctac gggagctgaa ttttaagccc    3060
atttacttta taggaagaaa cagaaaggta agaatcaagt ttgtaaagag aagagctgaa    3120
cttcagcgaa ttctcatttc tgcattgaat tcctgtgtct tagttataat cataggttta    3180
aaatttgggg ttttcttctg aactgaggaa gatcacatta ttgtatgaaa taggaatgtt    3240
ttgactagtt atgagaaacg taggctttca cgctaatttt aaagttataa ataactttcg    3300
aactattgcc aggggaagct ggtagccaag gtcgtgcttt gcattcagag agtttctggc    3360
tataaaaagc cgattggata ctgtgcagga aagataaga tatggcctgg at             3412
```

<210> SEQ ID NO 4
<211> LENGTH: 2979
<212> TYPE: DNA
<213> ORGANISM: Mus musculus
<220> FEATURE:
<221> NAME/KEY: CDS
<222> LOCATION: (160)..(2847)

<400> SEQUENCE: 4

```
cccctttctc tcttatcctg agtgaatggt gctcagctaa agggactgcc ccaccagctc    60
tgtctctttc ctcccaccct tcgagctctc tttggaaaaa ttccctccaa aagctgaacc    120
caaagctcat ttacttgtag gaagcatcag aaaggcaac atg tcg gca gaa acg      174
                                              Met Ser Ala Glu Thr
                                                1               5 cca ata acc ctg aat atg gac act cag gat ctg cag atc caa acg ttc     222
Pro Ile Thr Leu Asn Met Asp Thr Gln Asp Leu Gln Ile Gln Thr Phe
            10                  15                  20 act gtg gag aaa ctg ctg gag cct ctg ata atc cag gtt act acc ctg     270
Thr Val Glu Lys Leu Leu Glu Pro Leu Ile Ile Gln Val Thr Thr Leu
        25                  30                  35 gtg aat tgt ccg cag aat cct tcc aac agg aag aaa gga cgt tca aag     318
Val Asn Cys Pro Gln Asn Pro Ser Asn Arg Lys Lys Gly Arg Ser Lys
    40                  45                  50 aga gcc aga gtt ctt cta gct tcc gtg gag gaa gca act tgg aat ttg     366
Arg Ala Arg Val Leu Leu Ala Ser Val Glu Glu Ala Thr Trp Asn Leu
55                  60                  65 tta gac aag ggg gag atg att gct aag gaa gcc acg gtt tta aag gaa     414
Leu Asp Lys Gly Glu Met Ile Ala Lys Glu Ala Thr Val Leu Lys Glu
70                  75                  80                  85 gag ctg gca gct gca ctc cag gaa gtt cga aaa gag agc aaa gct ctg     462
Glu Leu Ala Ala Ala Leu Gln Glu Val Arg Lys Glu Ser Lys Ala Leu
                90                  95                 100 aag gta tca gct gag aga ttt aca gac gac ccc tgt tac ctc ccg aaa     510
Lys Val Ser Ala Glu Arg Phe Thr Asp Asp Pro Cys Tyr Leu Pro Lys
            105                 110                 115 agg gag gcc gtg gtt caa gcc gcc cgc gcc ctg ttg gca gca gtt aca     558
Arg Glu Ala Val Val Gln Ala Ala Arg Ala Leu Leu Ala Ala Val Thr
        120                 125                 130 aga ctc ctt gtt ctt gcc gac atg att gat gtc atg tgc ctc ttg cag     606
Arg Leu Leu Val Leu Ala Asp Met Ile Asp Val Met Cys Leu Leu Gln
    135                 140                 145 cat gtg tca tct ttc caa aga aca ttc gag tct ctc aaa aat gtt tcc     654
His Val Ser Ser Phe Gln Arg Thr Phe Glu Ser Leu Lys Asn Val Ser
150                 155                 160                 165 aac aag tcc gac ctc cag aga acc tac cag aag ctc ggg aag gag ctg     702
Asn Lys Ser Asp Leu Gln Arg Thr Tyr Gln Lys Leu Gly Lys Glu Leu
                170                 175                 180
```

```
gaa agc ctg gat tat ttg gcc ttc aaa cgc cag cag gac cta aaa tct    750
Glu Ser Leu Asp Tyr Leu Ala Phe Lys Arg Gln Gln Asp Leu Lys Ser
        185                 190                 195 cca agc cag agg gat gaa att gca ggg gcc cgg gcc acc ttg aag gag    798
Pro Ser Gln Arg Asp Glu Ile Ala Gly Ala Arg Ala Thr Leu Lys Glu
    200                 205                 210 aac tcc cca ctc ctg cat tct att tgt tca gca tgc ttg gaa cat tcc    846
Asn Ser Pro Leu Leu His Ser Ile Cys Ser Ala Cys Leu Glu His Ser
215                 220                 225 gat gtt gct tcg ctc aaa gcc agt aag gac acc gtc tgt gaa gag atc    894
Asp Val Ala Ser Leu Lys Ala Ser Lys Asp Thr Val Cys Glu Glu Ile
230                 235                 240                 245 cag aac gct ctt gat gta att tca aat gct tcc caa ggc atc cag aat    942
Gln Asn Ala Leu Asp Val Ile Ser Asn Ala Ser Gln Gly Ile Gln Asn
            250                 255                 260 gcg cca gcg ccc cct gaa cct cag gca gca aca ctg gga agt gct ttt    990
Ala Pro Ala Pro Pro Glu Pro Gln Ala Ala Thr Leu Gly Ser Ala Phe
            265                 270                 275 gat gag ctg gag aac tta att gtc ctg aac cca ctc aca gtg aca gag   1038
Asp Glu Leu Glu Asn Leu Ile Val Leu Asn Pro Leu Thr Val Thr Glu
        280                 285                 290 gaa gat gta aga cca tca cta gag aaa cgc cta gaa gcc atc atc agt   1086
Glu Asp Val Arg Pro Ser Leu Glu Lys Arg Leu Glu Ala Ile Ile Ser
    295                 300                 305 ggg gcc gca ctg ttg gcc gac tcg tcc tgc acc agg gac ctc cac cgg   1134
Gly Ala Ala Leu Leu Ala Asp Ser Ser Cys Thr Arg Asp Leu His Arg
310                 315                 320                 325 gag cgg att atc gcc gag tgc aat gcc atc cgc cag gct ctc cag gac   1182
Glu Arg Ile Ile Ala Glu Cys Asn Ala Ile Arg Gln Ala Leu Gln Asp
            330                 335                 340 ctg ctg acg gag tac atg agt aat act gga aaa aca gaa agg agt aat   1230
Leu Leu Thr Glu Tyr Met Ser Asn Thr Gly Lys Thr Glu Arg Ser Asn
            345                 350                 355 acc ctg aat act gcc att gtc aac atg agc aag aag aca aga gac ctc   1278
Thr Leu Asn Thr Ala Ile Val Asn Met Ser Lys Lys Thr Arg Asp Leu
        360                 365                 370 cgc aga cag ctc cgc aaa gct atc ata gat cac ata tca gat tct ttc   1326
Arg Arg Gln Leu Arg Lys Ala Ile Ile Asp His Ile Ser Asp Ser Phe
    375                 380                 385 ttg gat aca aca gtt cca ctc ctg gtc ctc att gaa gct gcg aag aat   1374
Leu Asp Thr Thr Val Pro Leu Leu Val Leu Ile Glu Ala Ala Lys Asn
390                 395                 400                 405 ggc cga gtc aag gaa atc aaa gac tat gct gcc ata ttt cat gag cac   1422
Gly Arg Val Lys Glu Ile Lys Asp Tyr Ala Ala Ile Phe His Glu His
            410                 415                 420 act ggc agg ctc gtg gag gtg gca aat ctg gct tgt tcc atg tca acg   1470
Thr Gly Arg Leu Val Glu Val Ala Asn Leu Ala Cys Ser Met Ser Thr
            425                 430                 435 aat gaa gat ggg att aaa atc gtc aga att gca gcc aat cac ctg gag   1518
Asn Glu Asp Gly Ile Lys Ile Val Arg Ile Ala Ala Asn His Leu Glu
        440                 445                 450 acc ctg tgt cca cag atc ata aat gct gca ctt gct ttg gca tca aga   1566
Thr Leu Cys Pro Gln Ile Ile Asn Ala Ala Leu Ala Leu Ala Ser Arg
    455                 460                 465 ccc aag agt caa gtg gtc aaa aac acc atg gaa atg tac aag cgc aca   1614
Pro Lys Ser Gln Val Val Lys Asn Thr Met Glu Met Tyr Lys Arg Thr
470                 475                 480                 485 tgg gaa cac tac atc cac gtc ctc act gaa gct gta gat gac atc acc   1662
Trp Glu His Tyr Ile His Val Leu Thr Glu Ala Val Asp Asp Ile Thr
            490                 495                 500
```

|     |     |     |     |     |     |     |     |     |     |     |     |     |     |     |     |      |
|---|---|---|---|---|---|---|---|---|---|---|---|---|---|---|---|---|
| agc | att | gac | gac | ttt | ctg | gct | gta | tct | gaa | agc | cac | atc | ctg | gaa | gat | 1710 |
| Ser | Ile | Asp | Asp | Phe | Leu | Ala | Val | Ser | Glu | Ser | His | Ile | Leu | Glu | Asp |      |
|     |     | 505 |     |     |     |     | 510 |     |     |     |     | 515 |     |     |     |      |
| gtc | aac | aaa | tgc | att | ata | gcc | ttg | aga | gat | cag | gac | gct | gat | aat | tta | 1758 |
| Val | Asn | Lys | Cys | Ile | Ile | Ala | Leu | Arg | Asp | Gln | Asp | Ala | Asp | Asn | Leu |      |
|     | 520 |     |     |     |     | 525 |     |     |     |     | 530 |     |     |     |     |      |
| gac | cga | gct | gcc | ggt | gcc | atc | aga | gga | cgg | gcc | gca | aga | gta | gct | cac | 1806 |
| Asp | Arg | Ala | Ala | Gly | Ala | Ile | Arg | Gly | Arg | Ala | Ala | Arg | Val | Ala | His |      |
| 535 |     |     |     |     | 540 |     |     |     |     | 545 |     |     |     |     |     |      |
| atc | gtt | gcg | ggt | gaa | atg | gat | agt | tac | gaa | ccc | ggc | gct | tac | acc | gaa | 1854 |
| Ile | Val | Ala | Gly | Glu | Met | Asp | Ser | Tyr | Glu | Pro | Gly | Ala | Tyr | Thr | Glu |      |
| 550 |     |     |     |     | 555 |     |     |     |     | 560 |     |     |     |     | 565 |      |
| ggt | gtg | atg | aga | aat | gtc | aac | ttc | ctt | aca | agc | act | gtg | atc | ccg | gag | 1902 |
| Gly | Val | Met | Arg | Asn | Val | Asn | Phe | Leu | Thr | Ser | Thr | Val | Ile | Pro | Glu |      |
|     |     |     |     | 570 |     |     |     |     | 575 |     |     |     |     | 580 |     |      |
| ttc | gtg | aca | caa | gtg | aat | gtg | gcc | cta | gat | gct | tta | agc | aag | aac | tct | 1950 |
| Phe | Val | Thr | Gln | Val | Asn | Val | Ala | Leu | Asp | Ala | Leu | Ser | Lys | Asn | Ser |      |
|     |     |     | 585 |     |     |     |     | 590 |     |     |     |     | 595 |     |     |      |
| ctg | act | gcg | ctt | gat | gat | aat | cag | ttt | gtg | gac | atc | tcc | aag | aag | atc | 1998 |
| Leu | Thr | Ala | Leu | Asp | Asp | Asn | Gln | Phe | Val | Asp | Ile | Ser | Lys | Lys | Ile |      |
|     |     |     |     | 600 |     |     |     |     | 605 |     |     |     |     | 610 |     |      |
| tat | gac | aca | atc | cat | gat | atc | agg | tgt | tcg | gtc | atg | atg | att | cgg | aca | 2046 |
| Tyr | Asp | Thr | Ile | His | Asp | Ile | Arg | Cys | Ser | Val | Met | Met | Ile | Arg | Thr |      |
|     |     |     | 615 |     |     |     |     | 620 |     |     |     |     | 625 |     |     |      |
| cca | gag | gaa | cta | gag | gat | gtt | tct | gac | ctt | gaa | gat | gac | cat | gag | gtc | 2094 |
| Pro | Glu | Glu | Leu | Glu | Asp | Val | Ser | Asp | Leu | Glu | Asp | Asp | His | Glu | Val |      |
| 630 |     |     |     |     | 635 |     |     |     |     | 640 |     |     |     |     | 645 |      |
| cgt | agc | cac | acc | agc | att | cag | aca | gaa | ggg | aaa | act | gat | cgg | gcc | aag | 2142 |
| Arg | Ser | His | Thr | Ser | Ile | Gln | Thr | Glu | Gly | Lys | Thr | Asp | Arg | Ala | Lys |      |
|     |     |     |     | 650 |     |     |     |     | 655 |     |     |     |     | 660 |     |      |
| atg | act | caa | ctg | cct | gag | gca | gaa | aag | gaa | aag | att | gct | gag | caa | gtc | 2190 |
| Met | Thr | Gln | Leu | Pro | Glu | Ala | Glu | Lys | Glu | Lys | Ile | Ala | Glu | Gln | Val |      |
|     |     |     |     | 665 |     |     |     |     | 670 |     |     |     |     | 675 |     |      |
| gcc | gac | ttc | aag | aag | gtg | aag | agc | aag | ctg | gac | gct | gag | att | gag | ata | 2238 |
| Ala | Asp | Phe | Lys | Lys | Val | Lys | Ser | Lys | Leu | Asp | Ala | Glu | Ile | Glu | Ile |      |
|     |     |     | 680 |     |     |     |     | 685 |     |     |     |     | 690 |     |     |      |
| tgg | gat | gac | aca | agc | aat | gac | atc | att | gtt | ctt | gcc | aag | aag | atg | tgc | 2286 |
| Trp | Asp | Asp | Thr | Ser | Asn | Asp | Ile | Ile | Val | Leu | Ala | Lys | Lys | Met | Cys |      |
|     | 695 |     |     |     |     | 700 |     |     |     |     | 705 |     |     |     |     |      |
| atg | atc | atg | atg | gag | atg | acc | gac | ttc | acg | agg | ggg | aaa | gga | cca | cta | 2334 |
| Met | Ile | Met | Met | Glu | Met | Thr | Asp | Phe | Thr | Arg | Gly | Lys | Gly | Pro | Leu |      |
| 710 |     |     |     |     | 715 |     |     |     |     | 720 |     |     |     |     | 725 |      |
| aag | cat | acc | act | gat | gta | atc | tat | gca | gct | aaa | atg | ata | tca | gag | tca | 2382 |
| Lys | His | Thr | Thr | Asp | Val | Ile | Tyr | Ala | Ala | Lys | Met | Ile | Ser | Glu | Ser |      |
|     |     |     |     | 730 |     |     |     |     | 735 |     |     |     |     | 740 |     |      |
| gga | tca | agg | atg | gat | gtt | ctt | gct | cgg | cag | att | gct | aac | cag | tgt | cca | 2430 |
| Gly | Ser | Arg | Met | Asp | Val | Leu | Ala | Arg | Gln | Ile | Ala | Asn | Gln | Cys | Pro |      |
|     |     |     | 745 |     |     |     |     | 750 |     |     |     |     | 755 |     |     |      |
| gat | cca | ccg | tgc | aaa | cag | gac | ttg | ctg | gct | tac | ctg | gaa | cag | att | aaa | 2478 |
| Asp | Pro | Pro | Cys | Lys | Gln | Asp | Leu | Leu | Ala | Tyr | Leu | Glu | Gln | Ile | Lys |      |
|     |     | 760 |     |     |     |     | 765 |     |     |     |     | 770 |     |     |     |      |
| ttc | tac | tcc | cac | cag | ctg | aaa | atc | tgc | agt | caa | gtt | aaa | gca | gag | atc | 2526 |
| Phe | Tyr | Ser | His | Gln | Leu | Lys | Ile | Cys | Ser | Gln | Val | Lys | Ala | Glu | Ile |      |
|     | 775 |     |     |     |     | 780 |     |     |     |     | 785 |     |     |     |     |      |
| caa | aat | ctg | ggg | gga | gaa | ctc | atc | gta | tca | gct | ttg | gac | agt | gtc | acc | 2574 |
| Gln | Asn | Leu | Gly | Gly | Glu | Leu | Ile | Val | Ser | Ala | Leu | Asp | Ser | Val | Thr |      |
| 790 |     |     |     |     | 795 |     |     |     |     | 800 |     |     |     |     | 805 |      |
| tcc | ctg | atc | cag | gca | gcc | aag | aat | tta | atg | aat | gct | gta | gtg | caa | aca | 2622 |
| Ser | Leu | Ile | Gln | Ala | Ala | Lys | Asn | Leu | Met | Asn | Ala | Val | Val | Gln | Thr |      |

```
                    810              815              820
gtg aaa atg tca tac att gcc tcc acc aag atc atc cgc atc cag agt      2670
Val Lys Met Ser Tyr Ile Ala Ser Thr Lys Ile Ile Arg Ile Gln Ser
            825              830              835 tct gca gga ccc cgg cac cca gta gtc atg tgg agg atg aag gct ccg      2718
Ser Ala Gly Pro Arg His Pro Val Val Met Trp Arg Met Lys Ala Pro
            840              845              850 gct aag aag ccc ttg att aaa aga gag aag cca gaa gaa aca tgg gca      2766
Ala Lys Lys Pro Leu Ile Lys Arg Glu Lys Pro Glu Glu Thr Trp Ala
            855              860              865 gct gcc aga aga ggc tct gcc aag aaa aag atc cac cca gtt caa gtc      2814
Ala Ala Arg Arg Gly Ser Ala Lys Lys Lys Ile His Pro Val Gln Val
870              875              880              885 atg agt gaa ttc aga ggg aga caa gtc tac tga ataccctcat ccactctagt   2867
Met Ser Glu Phe Arg Gly Arg Gln Val Tyr
                890              895 gcccatttct acaccccagg ctaaccacac tgctttattt catggttcat tggttcttta    2927
atttcaccaa gtttcagagt taagctcaca aataacataa aacattgggg tt           2979

<210> SEQ ID NO 5
<211> LENGTH: 895
<212> TYPE: PRT
<213> ORGANISM: Mus musculus

<400> SEQUENCE: 5

Met Ser Ala Glu Thr Pro Ile Thr Leu Asn Met Asp Thr Gln Asp Leu
1               5                   10                  15

Gln Ile Gln Thr Phe Thr Val Glu Lys Leu Leu Glu Pro Leu Ile Ile
            20                  25                  30

Gln Val Thr Thr Leu Val Asn Cys Pro Gln Asn Pro Ser Asn Arg Lys
        35                  40                  45

Lys Gly Arg Ser Lys Arg Ala Arg Val Leu Leu Ala Ser Val Glu Glu
    50                  55                  60

Ala Thr Trp Asn Leu Leu Asp Lys Gly Glu Met Ile Ala Lys Glu Ala
65                  70                  75                  80

Thr Val Leu Lys Glu Glu Leu Ala Ala Ala Leu Gln Glu Val Arg Lys
                85                  90                  95

Glu Ser Lys Ala Leu Lys Val Ser Ala Glu Arg Phe Thr Asp Asp Pro
            100                 105                 110

Cys Tyr Leu Pro Lys Arg Glu Ala Val Val Gln Ala Ala Arg Ala Leu
        115                 120                 125

Leu Ala Ala Val Thr Arg Leu Leu Val Leu Ala Asp Met Ile Asp Val
    130                 135                 140

Met Cys Leu Leu Gln His Val Ser Ser Phe Gln Arg Thr Phe Glu Ser
145                 150                 155                 160

Leu Lys Asn Val Ser Asn Lys Ser Asp Leu Gln Arg Thr Tyr Gln Lys
                165                 170                 175

Leu Gly Lys Glu Leu Glu Ser Leu Asp Tyr Leu Ala Phe Lys Arg Gln
            180                 185                 190

Gln Asp Leu Lys Ser Pro Ser Gln Arg Asp Glu Ile Ala Gly Ala Arg
        195                 200                 205

Ala Thr Leu Lys Glu Asn Ser Pro Leu Leu His Ser Ile Cys Ser Ala
    210                 215                 220

Cys Leu Glu His Ser Asp Val Ala Ser Leu Lys Ala Ser Lys Asp Thr
225                 230                 235                 240
```

-continued

```
Val Cys Glu Glu Ile Gln Asn Ala Leu Asp Val Ile Ser Asn Ala Ser
                245                 250                 255
Gln Gly Ile Gln Asn Ala Pro Ala Pro Pro Glu Pro Gln Ala Ala Thr
            260                 265                 270
Leu Gly Ser Ala Phe Asp Glu Leu Glu Asn Leu Ile Val Leu Asn Pro
            275                 280                 285
Leu Thr Val Thr Glu Glu Asp Val Arg Pro Ser Leu Glu Lys Arg Leu
        290                 295                 300
Glu Ala Ile Ile Ser Gly Ala Ala Leu Leu Ala Asp Ser Ser Cys Thr
305                 310                 315                 320
Arg Asp Leu His Arg Glu Arg Ile Ile Ala Glu Cys Asn Ala Ile Arg
                325                 330                 335
Gln Ala Leu Gln Asp Leu Leu Thr Glu Tyr Met Ser Asn Thr Gly Lys
            340                 345                 350
Thr Glu Arg Ser Asn Thr Leu Asn Thr Ala Ile Val Asn Met Ser Lys
        355                 360                 365
Lys Thr Arg Asp Leu Arg Arg Gln Leu Arg Lys Ala Ile Ile Asp His
    370                 375                 380
Ile Ser Asp Ser Phe Leu Asp Thr Thr Val Pro Leu Leu Val Leu Ile
385                 390                 395                 400
Glu Ala Ala Lys Asn Gly Arg Val Lys Glu Ile Lys Asp Tyr Ala Ala
                405                 410                 415
Ile Phe His Glu His Thr Gly Arg Leu Val Glu Val Ala Asn Leu Ala
            420                 425                 430
Cys Ser Met Ser Thr Asn Glu Asp Gly Ile Lys Ile Val Arg Ile Ala
        435                 440                 445
Ala Asn His Leu Glu Thr Leu Cys Pro Gln Ile Ile Asn Ala Ala Leu
    450                 455                 460
Ala Leu Ala Ser Arg Pro Lys Ser Gln Val Val Lys Asn Thr Met Glu
465                 470                 475                 480
Met Tyr Lys Arg Thr Trp Glu His Tyr Ile His Val Leu Thr Glu Ala
                485                 490                 495
Val Asp Asp Ile Thr Ser Ile Asp Asp Phe Leu Ala Val Ser Glu Ser
            500                 505                 510
His Ile Leu Glu Asp Val Asn Lys Cys Ile Ile Ala Leu Arg Asp Gln
        515                 520                 525
Asp Ala Asp Asn Leu Asp Arg Ala Ala Gly Ala Ile Arg Gly Arg Ala
    530                 535                 540
Ala Arg Val Ala His Ile Val Ala Gly Glu Met Asp Ser Tyr Glu Pro
545                 550                 555                 560
Gly Ala Tyr Thr Glu Gly Val Met Arg Asn Val Asn Phe Leu Thr Ser
                565                 570                 575
Thr Val Ile Pro Glu Phe Val Thr Gln Val Asn Val Ala Leu Asp Ala
            580                 585                 590
Leu Ser Lys Asn Ser Leu Thr Ala Leu Asp Asp Asn Gln Phe Val Asp
        595                 600                 605
Ile Ser Lys Lys Ile Tyr Asp Thr Ile His Asp Ile Arg Cys Ser Val
    610                 615                 620
Met Met Ile Arg Thr Pro Glu Glu Leu Glu Asp Val Ser Asp Leu Glu
625                 630                 635                 640
Asp Asp His Glu Val Arg Ser His Thr Ser Ile Gln Thr Glu Gly Lys
                645                 650                 655
Thr Asp Arg Ala Lys Met Thr Gln Leu Pro Glu Ala Glu Lys Glu Lys
```

-continued

```
                    660                 665                 670
Ile Ala Glu Gln Val Ala Asp Phe Lys Lys Val Lys Ser Lys Leu Asp
                675                 680                 685
Ala Glu Ile Glu Ile Trp Asp Asp Thr Ser Asn Asp Ile Ile Val Leu
    690                 695                 700
Ala Lys Lys Met Cys Met Ile Met Glu Met Thr Asp Phe Thr Arg
705                 710                 715                 720
Gly Lys Gly Pro Leu Lys His Thr Thr Asp Val Ile Tyr Ala Ala Lys
                725                 730                 735
Met Ile Ser Glu Ser Gly Ser Arg Met Asp Val Leu Ala Arg Gln Ile
            740                 745                 750
Ala Asn Gln Cys Pro Asp Pro Cys Lys Gln Asp Leu Leu Ala Tyr
            755                 760                 765
Leu Glu Gln Ile Lys Phe Tyr Ser His Gln Leu Lys Ile Cys Ser Gln
        770                 775                 780
Val Lys Ala Glu Ile Gln Asn Leu Gly Gly Glu Leu Ile Val Ser Ala
785                 790                 795                 800
Leu Asp Ser Val Thr Ser Leu Ile Gln Ala Ala Lys Asn Leu Met Asn
                805                 810                 815
Ala Val Val Gln Thr Val Lys Met Ser Tyr Ile Ala Ser Thr Lys Ile
                820                 825                 830
Ile Arg Ile Gln Ser Ser Ala Gly Pro Arg His Pro Val Val Met Trp
835                 840                 845
Arg Met Lys Ala Pro Ala Lys Lys Pro Leu Ile Lys Arg Glu Lys Pro
850                 855                 860
Glu Glu Thr Trp Ala Ala Ala Arg Arg Gly Ser Ala Lys Lys Lys Ile
865                 870                 875                 880
His Pro Val Gln Val Met Ser Glu Phe Arg Gly Arg Gln Val Tyr
                885                 890                 895
```

<210> SEQ ID NO 6
<211> LENGTH: 566
<212> TYPE: DNA
<213> ORGANISM: Mus musculus
<220> FEATURE:
<221> NAME/KEY: promoter
<222> LOCATION: 1...566
<223> OTHER INFORMATION: promoter sequence alpha-Tcatenin

<400> SEQUENCE: 6

```
acacggcgat atgtatcatc gccctgtggt ggnaatctgg tagcgttgtg acagtgtgag    60
acggtaagat ttcggcagaa aaaacgatct cagatgtgac ccatgactcc agagaccctg   120
cattttagct agtaacgatg cagggatttc ctggactctt gtatctcccc gctttacagt   180
ttctcacttc caggtaattg taaccttcgg ctttaattcg aaacggttcc ttgttttgga   240
tgggatgac aaagttaaag ctgacttatt tagagcttcc gaagaagtat ggaggtctct   300
agggaatgta tgtgtctggc ctttttcaac aaagtatttt cagcaacaag ttgtcagtga   360
ggtcagcgcg gagcccagga ttagatacca cccaccctg gcttgtaacc tccccttct   420
ctcttatcct gagtgaatgg tgctcagcta aagggactgc cccaccagct ctgtctcttt   480
cctcccaccc ttcgagctct ctttggaaaa attccctcca aagctgaac ccaaagctca   540
tttacttgta ggaagcatca gaaagg                                       566
```

<210> SEQ ID NO 7
<211> LENGTH: 21

```
<212> TYPE: DNA
<213> ORGANISM: Homo sapiens
<220> FEATURE:
<221> NAME/KEY: misc_feature
<222> LOCATION: 1...21
<223> OTHER INFORMATION: splice acceptor 0

<400> SEQUENCE: 7
annctggGtg aacaacgctc a                                           21

<210> SEQ ID NO 8
<211> LENGTH: 21
<212> TYPE: DNA
<213> ORGANISM: Homo sapiens
<220> FEATURE:
<223> OTHER INFORMATION: splice donor 1

<400> SEQUENCE: 8
aacagaaagg taagaatcaa g                                           21

<210> SEQ ID NO 9
<211> LENGTH: 20
<212> TYPE: DNA
<213> ORGANISM: Homo sapiens
<220> FEATURE:
<223> OTHER INFORMATION: splice acceptor 1

<400> SEQUENCE: 9
tttgtgcagc aggcagcatg                                             20

<210> SEQ ID NO 10
<211> LENGTH: 21
<212> TYPE: DNA
<213> ORGANISM: Homo sapiens
<220> FEATURE:
<223> OTHER INFORMATION: splice donor 2

<400> SEQUENCE: 10
ataatccagg tattaatacc a                                           21

<210> SEQ ID NO 11
<211> LENGTH: 21
<212> TYPE: DNA
<213> ORGANISM: Homo sapiens
<220> FEATURE:
<223> OTHER INFORMATION: splice acceptor 2

<400> SEQUENCE: 11
ttccaatttt aggttaccac a                                           21

<210> SEQ ID NO 12
<211> LENGTH: 19
<212> TYPE: DNA
<213> ORGANISM: Homo sapiens
<220> FEATURE:
<223> OTHER INFORMATION: splice donor 3

<400> SEQUENCE: 12
aaagaaagtg agtactcca                                              19

<210> SEQ ID NO 13
<211> LENGTH: 20
<212> TYPE: DNA
<213> ORGANISM: Homo sapiens
<220> FEATURE:
<223> OTHER INFORMATION: splice acceptor 3
```

```
<400> SEQUENCE: 13 tgtattttc aggtgaagct                                                    20

<210> SEQ ID NO 14
<211> LENGTH: 20
<212> TYPE: DNA
<213> ORGANISM: Homo sapiens
<220> FEATURE:
<223> OTHER INFORMATION: splice donor 4

<400> SEQUENCE: 14
gtgtcagctg taagtaaaga                                                   20

<210> SEQ ID NO 15
<211> LENGTH: 21
<212> TYPE: DNA
<213> ORGANISM: Homo sapiens
<220> FEATURE:
<223> OTHER INFORMATION: splice acceptor 4

<400> SEQUENCE: 15
tttcaatttc agtttcaaag g                                                 21

<210> SEQ ID NO 16
<211> LENGTH: 21
<212> TYPE: DNA
<213> ORGANISM: Homo sapiens
<220> FEATURE:
<223> OTHER INFORMATION: splice donor 5

<400> SEQUENCE: 16
cgtcagcagg taggagtcag a                                                 21

<210> SEQ ID NO 17
<211> LENGTH: 21
<212> TYPE: DNA
<213> ORGANISM: Homo sapiens
<220> FEATURE:
<223> OTHER INFORMATION: splice acceptor 5

<400> SEQUENCE: 17
ttaccttctc aggacttaaa a                                                 21

<210> SEQ ID NO 18
<211> LENGTH: 21
<212> TYPE: DNA
<213> ORGANISM: Homo sapiens
<220> FEATURE:
<223> OTHER INFORMATION: splice donor 6

<400> SEQUENCE: 18
gagctggagg taagtcggga g                                                 21

<210> SEQ ID NO 19
<211> LENGTH: 21
<212> TYPE: DNA
<213> ORGANISM: Homo sapiens
<220> FEATURE:
<223> OTHER INFORMATION: splice acceptor 6

<400> SEQUENCE: 19
ttcttctctt agaatttaat t                                                 21

<210> SEQ ID NO 20
<211> LENGTH: 21
```

```
<212> TYPE: DNA
<213> ORGANISM: Homo sapiens
<220> FEATURE:
<223> OTHER INFORMATION: splice donor 7

<400> SEQUENCE: 20
atgaacaacg taagtatagt t                                              21

<210> SEQ ID NO 21
<211> LENGTH: 22
<212> TYPE: DNA
<213> ORGANISM: Homo sapiens
<220> FEATURE:
<223> OTHER INFORMATION: splice acceptor 7

<400> SEQUENCE: 21
tcttcctttg caggctggaa aa                                             22

<210> SEQ ID NO 22
<211> LENGTH: 21
<212> TYPE: DNA
<213> ORGANISM: Homo sapiens
<220> FEATURE:
<223> OTHER INFORMATION: splice donor 8

<400> SEQUENCE: 22
cgcagacagg tgagggaaga g                                              21

<210> SEQ ID NO 23
<211> LENGTH: 21
<212> TYPE: DNA
<213> ORGANISM: Homo sapiens
<220> FEATURE:
<223> OTHER INFORMATION: splice acceptor 8

<400> SEQUENCE: 23
atttcttctc agctccgcaa g                                              21

<210> SEQ ID NO 24
<211> LENGTH: 21
<212> TYPE: DNA
<213> ORGANISM: Homo sapiens
<220> FEATURE:
<223> OTHER INFORMATION: splice donor 9

<400> SEQUENCE: 24
cttgtagagg taagcatgct a                                              21

<210> SEQ ID NO 25
<211> LENGTH: 21
<212> TYPE: DNA
<213> ORGANISM: Homo sapiens
<220> FEATURE:
<223> OTHER INFORMATION: splice acceptor 9

<400> SEQUENCE: 25 attgtatttta aggtggcaaa t                                             21

<210> SEQ ID NO 26
<211> LENGTH: 21
<212> TYPE: DNA
<213> ORGANISM: Homo sapiens
<220> FEATURE:
<223> OTHER INFORMATION: splice donor 10

<400> SEQUENCE: 26
```

```
tgtccacagg tatgacaact a                                              21
```

<210> SEQ ID NO 27
<211> LENGTH: 21
<212> TYPE: DNA
<213> ORGANISM: Homo sapiens
<220> FEATURE:
<223> OTHER INFORMATION: splice acceptor 10

<400> SEQUENCE: 27

```
ttatctttat agattattaa t                                              21
```

<210> SEQ ID NO 28
<211> LENGTH: 19
<212> TYPE: DNA
<213> ORGANISM: Homo sapiens
<220> FEATURE:
<223> OTHER INFORMATION: splice donor 11

<400> SEQUENCE: 28

```
gtatctggta tgttttat                                                  19
```

<210> SEQ ID NO 29
<211> LENGTH: 20
<212> TYPE: DNA
<213> ORGANISM: Homo sapiens
<220> FEATURE:
<223> OTHER INFORMATION: splice acceptor 11

<400> SEQUENCE: 29

```
atttacttac agaaagccat                                                20
```

<210> SEQ ID NO 30
<211> LENGTH: 19
<212> TYPE: DNA
<213> ORGANISM: Homo sapiens
<220> FEATURE:
<223> OTHER INFORMATION: splice donor 12

<400> SEQUENCE: 30

```
agtactggta agtcagttg                                                 19
```

<210> SEQ ID NO 31
<211> LENGTH: 20
<212> TYPE: DNA
<213> ORGANISM: Homo sapiens
<220> FEATURE:
<223> OTHER INFORMATION: splice acceptor 12

<400> SEQUENCE: 31

```
ttattttaac agtaattcct                                                20
```

<210> SEQ ID NO 32
<211> LENGTH: 20
<212> TYPE: DNA
<213> ORGANISM: Homo sapiens
<220> FEATURE:
<223> OTHER INFORMATION: splice donor 13

<400> SEQUENCE: 32

```
atgattcggt aagtttgctt                                                20
```

<210> SEQ ID NO 33
<211> LENGTH: 19
<212> TYPE: DNA
<213> ORGANISM: Homo sapiens

```
<220> FEATURE:
<223> OTHER INFORMATION: splice acceptor 13

<400> SEQUENCE: 33 ttcttttttat aggacccca                                                19

<210> SEQ ID NO 34
<211> LENGTH: 21
<212> TYPE: DNA
<213> ORGANISM: Homo sapiens
<220> FEATURE:
<223> OTHER INFORMATION: splice donor 14

<400> SEQUENCE: 34
actgataggg tatgtcactt c                                              21

<210> SEQ ID NO 35
<211> LENGTH: 21
<212> TYPE: DNA
<213> ORGANISM: Homo sapiens
<220> FEATURE:
<223> OTHER INFORMATION: splice acceptor 14

<400> SEQUENCE: 35
cacatgtttt aggctaagat g                                              21

<210> SEQ ID NO 36
<211> LENGTH: 20
<212> TYPE: DNA
<213> ORGANISM: Homo sapiens
<220> FEATURE:
<223> OTHER INFORMATION: splice donor 15

<400> SEQUENCE: 36
ttcactaggt aattatgtgg                                                20

<210> SEQ ID NO 37
<211> LENGTH: 19
<212> TYPE: DNA
<213> ORGANISM: Homo sapiens
<220> FEATURE:
<223> OTHER INFORMATION: splice acceptor 15

<400> SEQUENCE: 37 attttttttcc agggggcaaa                                               19

<210> SEQ ID NO 38
<211> LENGTH: 21
<212> TYPE: DNA
<213> ORGANISM: Homo sapiens
<220> FEATURE:
<223> OTHER INFORMATION: splice donor 16

<400> SEQUENCE: 38
gctaatcagg tgagttactt a                                              21

<210> SEQ ID NO 39
<211> LENGTH: 21
<212> TYPE: DNA
<213> ORGANISM: Homo sapiens
<220> FEATURE:
<223> OTHER INFORMATION: splice acceptor 16

<400> SEQUENCE: 39
atgcatattt agtgcccaga t                                              21
```

```
<210> SEQ ID NO 40
<211> LENGTH: 21
<212> TYPE: DNA
<213> ORGANISM: Homo sapiens
<220> FEATURE:
<223> OTHER INFORMATION: splice donor 17

<400> SEQUENCE: 40
atgtcagctg tgagtactgc c                                              21

<210> SEQ ID NO 41
<211> LENGTH: 21
<212> TYPE: DNA
<213> ORGANISM: Homo sapiens
<220> FEATURE:
<223> OTHER INFORMATION: splice acceptor 17

<400> SEQUENCE: 41
ttttccctac agttggacag t                                              21

<210> SEQ ID NO 42
<211> LENGTH: 19
<212> TYPE: DNA
<213> ORGANISM: Homo sapiens
<220> FEATURE:
<223> OTHER INFORMATION: splice donor 18

<400> SEQUENCE: 42
atatatattt gggatcatt                                                 19

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: upper
      primer FVR2513

<400> SEQUENCE: 43
ttgcttgtaa cctcccnttt                                                20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: lower
      primer FVR2514

<400> SEQUENCE: 44
gcgtgaaagc ctacgtttct                                                20

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: upper
      primer FVR2515

<400> SEQUENCE: 45
taatttgtta caggacctaa gc                                             22

<210> SEQ ID NO 46
<211> LENGTH: 23
<212> TYPE: DNA
```

-continued

```
<213> ORGANISM: Artificial Sequence
<220> FEATURE:
<223> OTHER INFORMATION: Description of Artificial Sequence: lower
      primer FVR2516

<400> SEQUENCE: 46
tcttcattat tcattttcc cac                                              23

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: upper
      primer FVR2517

<400> SEQUENCE: 47
tatcccagga ctgtgttctc                                                 20

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: loower
      primer FVR2518

<400> SEQUENCE: 48
tggagccaaa aacaaaaca                                                  19

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: upper
      primer FVR2519

<400> SEQUENCE: 49
tggggttgta tttttcaggt g                                               21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: lower
      primer FVR2520

<400> SEQUENCE: 50
gccaggttca gagaatgaaa t                                               21

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: upper
      primer FVR2521

<400> SEQUENCE: 51
ggactgaaca ggcttctcat                                                 20

<210> SEQ ID NO 52
<211> LENGTH: 20
<212> TYPE: DNA
<213> ORGANISM: Artificial Sequence
```

```
<220> FEATURE:
<223> OTHER INFORMATION: Description of Artificial Sequence: lower
      primer FVR2522

<400> SEQUENCE: 52
gcaggaagcc taaagtgttc                                              20

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: upper
      primer FVR2523

<400> SEQUENCE: 53
gtctttctcc cataacccat t                                            21

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: lower
      primer FVR2524

<400> SEQUENCE: 54
cgccaacatg tggatcttct                                              20

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: upper
      primer FVR2525

<400> SEQUENCE: 55
tgaaatgcca tggagctcta a                                            21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: lower
      primer FVR2526

<400> SEQUENCE: 56
acggaaagta tctcagccta t                                            21

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: upper
      primer FVR2958

<400> SEQUENCE: 57
ccattgctta tgtcgttttt tc                                           22

<210> SEQ ID NO 58
<211> LENGTH: 21
<212> TYPE: DNA
<213> ORGANISM: Artificial Sequence
<220> FEATURE:
```

```
<223> OTHER INFORMATION: Description of Artificial Sequence: lower
      primer FVR2959

<400> SEQUENCE: 58 ttagcccta tgtttctgac t                                              21

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: upper
      primer FVR2960

<400> SEQUENCE: 59
agaaaaggaa acacagtgaa ct                                            22

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: lower
      primer FVR2961

<400> SEQUENCE: 60
ttctcctgga ctttagtgag tt                                            22

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: upper
      primer FVR2527

<400> SEQUENCE: 61
tgttgctgca tttccttgct a                                             21

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: lower
      primer FVR2528

<400> SEQUENCE: 62
gcgagacctg gtctcaaaaa                                               20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: upper
      primer FVR2529

<400> SEQUENCE: 63
gtgcccatca cccaaatagt                                               20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: lower
```

```
      primer FVR2530

<400> SEQUENCE: 64
ccatgcctgt cccagtatta                                              20

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: upper
      primer FVR2531

<400> SEQUENCE: 65
ccatttccaa tgtgcactct a                                            21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: lower
      primer FVR2532

<400> SEQUENCE: 66
aattgtgcag ctgttattgg c                                            21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: upper
      primer FVR2956

<400> SEQUENCE: 67
acaaagagga caatcttctc c                                            21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: lower
      primer FVR2957

<400> SEQUENCE: 68
tcaatggaag gaaaagcaaa c                                            21

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: upper
      primer FVR2533

<400> SEQUENCE: 69
tgggagtgaa attgctgggt                                              20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: lower
      primer FVR2534
```

```
<400> SEQUENCE: 70
tagaggctgc ctagattgac                                              20

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: upper
      primer FVR2535

<400> SEQUENCE: 71
tgcttttgac atagtggaat ga                                           22

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: lower
      primer FVR2536

<400> SEQUENCE: 72
tggcacttga cactcagaga                                              20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: upper
      primer FVR2537

<400> SEQUENCE: 73
ccgttctttg ggatgcgaat                                              20

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: lower
      primer FVR2538

<400> SEQUENCE: 74
ggcaaagagc aattagcatg a                                            21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: upper
      primer FVR2539

<400> SEQUENCE: 75
aaggtacctg ccatgtgaat a                                            21

<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence: lower
      primer FVR2540
```

-continued

<400> SEQUENCE: 76
agatttggtc atgtaaacaa gg                                          22

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: upper
      primer FVR2541

<400> SEQUENCE: 77
ccacgcttgg caataattaa c                                           21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: lower
      primer FVR2542

<400> SEQUENCE: 78
tgctgaccat acagaaatga c                                           21

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: primer
      MCB53

<400> SEQUENCE: 79
cttcgggcct ctggaattta                                             20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: primer
      MCB73

<400> SEQUENCE: 80
cgacatcagg gtgctgtagg                                             20

<210> SEQ ID NO 81
<211> LENGTH: 29
<212> TYPE: DNA
<213> ORGANISM: Artificial Sequence
<220> FEATURE:
<223> OTHER INFORMATION: Description of Artificial Sequence: primer
      MCB133

<400> SEQUENCE: 81
ggtgaattcg tcagcagcaa gggcatcat                                   29

<210> SEQ ID NO 82
<211> LENGTH: 29
<212> TYPE: DNA
<213> ORGANISM: Artificial Sequence
<220> FEATURE:
<223> OTHER INFORMATION: Description of Artificial Sequence: primer
      MCB134

<400> SEQUENCE: 82
ggtttgatgc agggtccaca ggcagttct                                             29

<210> SEQ ID NO 83
<211> LENGTH: 30
<212> TYPE: DNA
<213> ORGANISM: Artificial Sequence
<220> FEATURE:
<223> OTHER INFORMATION: Description of Artificial Sequence: primer
      MCB137

<400> SEQUENCE: 83
acccccgggg ggcaacttca cctatcattc                                            30

<210> SEQ ID NO 84
<211> LENGTH: 30
<212> TYPE: DNA
<213> ORGANISM: Artificial Sequence
<220> FEATURE:
<223> OTHER INFORMATION: Description of Artificial Sequence: primer
      MCB138

<400> SEQUENCE: 84
gccgccgcct tccttttcat ttccgctctt                                            30

<210> SEQ ID NO 85
<211> LENGTH: 30
<212> TYPE: DNA
<213> ORGANISM: Artificial Sequence
<220> FEATURE:
<223> OTHER INFORMATION: Description of Artificial Sequence: primer
      MCB711

<400> SEQUENCE: 85 aggggggcagt ggctgaagaa agaagtaatc                                           30

<210> SEQ ID NO 86
<211> LENGTH: 29
<212> TYPE: DNA
<213> ORGANISM: Artificial Sequence
<220> FEATURE:
<223> OTHER INFORMATION: Description of Artificial Sequence: primer
      MCB725

<400> SEQUENCE: 86
tattagatat cgcctctccc ggacccgcc                                             29

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: primer
      MCB967

<400> SEQUENCE: 87
tgaggcagaa aaagaaaaga                                                       20

<210> SEQ ID NO 88
<211> LENGTH: 19
<212> TYPE: DNA
<213> ORGANISM: Artificial Sequence
<220> FEATURE:
<223> OTHER INFORMATION: Description of Artificial Sequence: primer
      MCB968

<400> SEQUENCE: 88
agtgtggtta ggcaggatt                                                19

<210> SEQ ID NO 89
<211> LENGTH: 17
<212> TYPE: DNA
<213> ORGANISM: Artificial Sequence
<220> FEATURE:
<223> OTHER INFORMATION: Description of Artificial Sequence: primer
      MCB1010

<400> SEQUENCE: 89
gctgagcctc gtctgac                                                  17

<210> SEQ ID NO 90
<211> LENGTH: 23
<212> TYPE: DNA
<213> ORGANISM: Artificial Sequence
<220> FEATURE:
<223> OTHER INFORMATION: Description of Artificial Sequence: primer
      MCB1027

<400> SEQUENCE: 90
aatctgccga gcaaggacat cca                                           23

<210> SEQ ID NO 91
<211> LENGTH: 23
<212> TYPE: DNA
<213> ORGANISM: Artificial Sequence
<220> FEATURE:
<223> OTHER INFORMATION: Description of Artificial Sequence: primer
      MCB1028

<400> SEQUENCE: 91
tcaggcagtt gagtcatctt agc                                           23

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: primer
      MCB1254

<400> SEQUENCE: 92
acccgtgacg atgtgagcaa ctc                                           23

<210> SEQ ID NO 93
<211> LENGTH: 23
<212> TYPE: DNA
<213> ORGANISM: Artificial Sequence
<220> FEATURE:
<223> OTHER INFORMATION: Description of Artificial Sequence: primer
      MCB1255

<400> SEQUENCE: 93
gagctgtctg cgaaggtctc ttg                                           23

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: primer
      MCB1260

<400> SEQUENCE: 94 gaaaagaaa agattgctga g                                              21

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: primer MCB1261

<400> SEQUENCE: 95
ccctagtgaa gtctgtcatc t                                     21

<210> SEQ ID NO 96
<211> LENGTH: 27
<212> TYPE: DNA
<213> ORGANISM: Artificial Sequence
<220> FEATURE:
<223> OTHER INFORMATION: Description of Artificial Sequence: primer MCB1607

<400> SEQUENCE: 96
agaattctca gctgaaacac caatcac                               27

<210> SEQ ID NO 97
<211> LENGTH: 27
<212> TYPE: DNA
<213> ORGANISM: Artificial Sequence
<220> FEATURE:
<223> OTHER INFORMATION: Description of Artificial Sequence: primer MCB1608

<400> SEQUENCE: 97
gggatccgta gatttgtctt cctctaa                               27

<210> SEQ ID NO 98
<211> LENGTH: 25
<212> TYPE: DNA
<213> ORGANISM: Artificial Sequence
<220> FEATURE:
<223> OTHER INFORMATION: Description of Artificial Sequence: primer MCB1609

<400> SEQUENCE: 98
aggatcctgc gaaggtctct tgtct                                 25

<210> SEQ ID NO 99
<211> LENGTH: 27
<212> TYPE: DNA
<213> ORGANISM: Artificial Sequence
<220> FEATURE:
<223> OTHER INFORMATION: Description of Artificial Sequence: primer MCB1610

<400> SEQUENCE: 99
ggatgataat caatttgtgg acatctc                               27

<210> SEQ ID NO 100
<211> LENGTH: 18
<212> TYPE: DNA
<213> ORGANISM: Artificial Sequence
<220> FEATURE:
<223> OTHER INFORMATION: Description of Artificial Sequence: primer MCB2043

<400> SEQUENCE: 100
tcgaggatga aggctctg                                         18

```
<210> SEQ ID NO 101
<211> LENGTH: 18
<212> TYPE: DNA
<213> ORGANISM: Artificial Sequence
<220> FEATURE:
<223> OTHER INFORMATION: Description of Artificial Sequence: primer
      MCB2044

<400> SEQUENCE: 101
tgtttaaccc caatgttt                                                    18

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: primer
      MCB2056

<400> SEQUENCE: 102
gaaatgccat ggagctctaa c                                                21

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: primer
      MCB2057

<400> SEQUENCE: 103
atgggaaggc aaaccagtca c                                                21

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: primer
      MCB2099

<400> SEQUENCE: 104
tgtcatctgc ctctcaattt g                                                21

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: primer
      MCB2100

<400> SEQUENCE: 105
atgctgcctt tctgtttctt c                                                21

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: primer
      MCB2217

<400> SEQUENCE: 106
cagatgacag tggggcagtc                                                  20
```

```
<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: primer
      MCB2219

<400> SEQUENCE: 107
accacagtcc atgccatcac                                                    20

<210> SEQ ID NO 108
<211> LENGTH: 18
<212> TYPE: DNA
<213> ORGANISM: Artificial Sequence
<220> FEATURE:
<223> OTHER INFORMATION: Description of Artificial Sequence: primer
      MCB2220

<400> SEQUENCE: 108
tccaccaccc tgttgctg                                                      18

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: primer
      MCB2287

<400> SEQUENCE: 109
aacttgttac tgaaaatact                                                    20

<210> SEQ ID NO 110
<211> LENGTH: 18
<212> TYPE: DNA
<213> ORGANISM: Artificial Sequence
<220> FEATURE:
<223> OTHER INFORMATION: Description of Artificial Sequence: primer
      MCB2335

<400> SEQUENCE: 110
cctcttgcaa catgtgtc                                                      18

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: primer
      MCB2350

<400> SEQUENCE: 111
cattaccatt tttccgactt                                                    20

<210> SEQ ID NO 112
<211> LENGTH: 42
<212> TYPE: DNA
<213> ORGANISM: Artificial Sequence
<220> FEATURE:
<223> OTHER INFORMATION: Description of Artificial Sequence: primer
      MCB2386

<400> SEQUENCE: 112
gggggcggcc gcggagggtc agctgaaaca ccaatcacat tg                           42

<210> SEQ ID NO 113
```

<211> LENGTH: 42
<212> TYPE: DNA
<213> ORGANISM: Artificial Sequence
<220> FEATURE:
<223> OTHER INFORMATION: Description of Artificial Sequence: primer
      MCB2387

<400> SEQUENCE: 113
ccccgaattc gccgtgtggt taggcaggat tttgtcatat ag        42

<210> SEQ ID NO 114
<211> LENGTH: 19
<212> TYPE: DNA
<213> ORGANISM: Artificial Sequence
<220> FEATURE:
<223> OTHER INFORMATION: Description of Artificial Sequence: primer
      MCB2461

<400> SEQUENCE: 114
ccccaatgtt ttatgttat        19

<210> SEQ ID NO 115
<211> LENGTH: 18
<212> TYPE: DNA
<213> ORGANISM: Artificial Sequence
<220> FEATURE:
<223> OTHER INFORMATION: Description of Artificial Sequence: primer
      MCB2463

<400> SEQUENCE: 115
ggggagaact catcgtat        18

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: primer
      MCB2479

<400> SEQUENCE: 116
gccctgattg agtttgataa        20

<210> SEQ ID NO 117
<211> LENGTH: 19
<212> TYPE: DNA
<213> ORGANISM: Artificial Sequence
<220> FEATURE:
<223> OTHER INFORMATION: Description of Artificial Sequence: primer
      MCB2480

<400> SEQUENCE: 117
cccagcttca tagttctcc        19

<210> SEQ ID NO 118
<211> LENGTH: 22
<212> TYPE: DNA
<213> ORGANISM: Artificial Sequence
<220> FEATURE:
<223> OTHER INFORMATION: Description of Artificial Sequence: primer
      MCB2481

<400> SEQUENCE: 118
cttggtggag gcaatgtatg ac        22

<210> SEQ ID NO 119
<211> LENGTH: 22

```
<212> TYPE: DNA
<213> ORGANISM: Artificial Sequence
<220> FEATURE:
<223> OTHER INFORMATION: Description of Artificial Sequence: primer
      MCB2482

<400> SEQUENCE: 119
tctgccgagc aagaacatcc at                                              22

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: primer
      MCB2567

<400> SEQUENCE: 120
gcggaggtct cttgtcttct t                                               21

<210> SEQ ID NO 121
<211> LENGTH: 22
<212> TYPE: DNA
<213> ORGANISM: Artificial Sequence
<220> FEATURE:
<223> OTHER INFORMATION: Description of Artificial Sequence: primer
      MCB2569

<400> SEQUENCE: 121
cgcagtcaga gagttcttgc tt                                              22

<210> SEQ ID NO 122
<211> LENGTH: 18
<212> TYPE: DNA
<213> ORGANISM: Artificial Sequence
<220> FEATURE:
<223> OTHER INFORMATION: Description of Artificial Sequence: primer
      MCB2636

<400> SEQUENCE: 122
gaaggcccct gagaagaa                                                   18

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: primer
      MCB2637

<400> SEQUENCE: 123
cccgaataaa gcaactccat                                                 20

<210> SEQ ID NO 124
<211> LENGTH: 24
<212> TYPE: DNA
<213> ORGANISM: Artificial Sequence
<220> FEATURE:
<223> OTHER INFORMATION: Description of Artificial Sequence: primer
      MCB2711

<400> SEQUENCE: 124
cttcccgagc ttctggtagg ttct                                            24

<210> SEQ ID NO 125
<211> LENGTH: 20
<212> TYPE: DNA
```

```
<213> ORGANISM: Artificial Sequence
<220> FEATURE:
<223> OTHER INFORMATION: Description of Artificial Sequence: primer
      MCB2818

<400> SEQUENCE: 125
aacgcctaga agccatcatc                                              20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: primer
      MCB2819

<400> SEQUENCE: 126
tggcaagaac aatgatgtca                                              20

<210> SEQ ID NO 127
<211> LENGTH: 22
<212> TYPE: DNA
<213> ORGANISM: Artificial Sequence
<220> FEATURE:
<223> OTHER INFORMATION: Description of Artificial Sequence: primer
      MCB2820

<400> SEQUENCE: 127
cccctttctc tcttatcctg ag                                           22

<210> SEQ ID NO 128
<211> LENGTH: 25
<212> TYPE: DNA
<213> ORGANISM: Artificial Sequence
<220> FEATURE:
<223> OTHER INFORMATION: Description of Artificial Sequence: primer
      MCB2837

<400> SEQUENCE: 128
ctttctgatg cttcctacaa gtaaa                                        25

<210> SEQ ID NO 129
<211> LENGTH: 19
<212> TYPE: DNA
<213> ORGANISM: Artificial Sequence
<220> FEATURE:
<223> OTHER INFORMATION: Description of Artificial Sequence: primer
      MCB2838

<400> SEQUENCE: 129
ccgcagaatc cttccaaca                                               19

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: primer
      MCB2839

<400> SEQUENCE: 130
gctgccagct cttcctttaa a                                            21

<210> SEQ ID NO 131
<211> LENGTH: 19
<212> TYPE: DNA
<213> ORGANISM: Artificial Sequence
```

```
<220> FEATURE:
<223> OTHER INFORMATION: Description of Artificial Sequence: primer
      MCB2840

<400> SEQUENCE: 131
gtcggcagaa acgccaata                                                    19

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: primer
      MCB2841

<400> SEQUENCE: 132
gaggctccag cagtttctcc                                                   20

<210> SEQ ID NO 133
<211> LENGTH: 17
<212> TYPE: PRT
<213> ORGANISM: Artificial Sequence
<220> FEATURE:
<223> OTHER INFORMATION: Description of Artificial Sequence: amino-
      terminus of human alpha-Tcatenin

<400> SEQUENCE: 133

Met Ser Ala Glu Thr Pro Ile Thr Leu Asn Ile Asp Pro Gln Asp Leu
  1               5                  10                  15

Gln

<210> SEQ ID NO 134
<211> LENGTH: 17
<212> TYPE: PRT
<213> ORGANISM: Artificial Sequence
<220> FEATURE:
<223> OTHER INFORMATION: Description of Artificial Sequence:
      carboxy-terminus of alpha-Tcatenin

<400> SEQUENCE: 134

Tyr Ile Gln Arg Gly Arg Phe Glu Ser Met Val Gln Leu Pro His Ile
  1               5                  10                  15

Lys
```